(12) United States Patent
Takematsu et al.

(10) Patent No.: US 6,337,417 B1
(45) Date of Patent: Jan. 8, 2002

(54) N-PHENYLTETRAHYDROPHTHALAMIC ACID DERIVATIVES, METHODS OF PRODUCING SAME, AND HERBICIDES CONTAINING SAME AS EFFECTIVE COMPONENTS

(75) Inventors: Tetsuo Takematsu, Utsunomiya; Takeo Komata; Takashi Kume, both of Kawagoe; Yumiko Kohda, Kawaguchi; Kiyoshi Suzuki, Utsunomiya; Matsue Kawamura, Kawagoe; Yukio Ikeda, Kawachi; Kaoru Mori, Higashimatsuyama, all of (JP)

(73) Assignee: Central Glass Co., Ltd., Ube (JP)

( * ) Notice: Subject to any disclaimer, the term of this patent is extended or adjusted under 35 U.S.C. 154(b) by 0 days.

(21) Appl. No.: 09/097,010

(22) Filed: Jun. 15, 1998

Related U.S. Application Data

(62) Division of application No. 08/676,148, filed as application No. PCT/JP95/00044 on Jan. 19, 1995, now Pat. No. 5,801,122.

(30) Foreign Application Priority Data

Jan. 19, 1994 (JP) .............................................. 6-004205
Jan. 19, 1994 (JP) .............................................. 6-004206
Jan. 19, 1994 (JP) .............................................. 6-004207

(51) Int. Cl.$^7$ ........................ A01N 43/10; A01N 43/36; C07D 333/22; C07C 321/00
(52) U.S. Cl. ............................ 560/17; 560/45; 504/260; 504/289; 504/315; 546/316; 546/326; 546/329; 546/335; 549/72; 549/77; 549/80
(58) Field of Search .................. 560/17, 45; 504/260, 504/289, 315; 546/316, 326, 329, 335; 549/72, 77, 80

(56) References Cited

U.S. PATENT DOCUMENTS 4,613,675 A * 9/1986 Lee ............................ 558/170
5,068,365 A * 11/1991 Tokunaga et al. ........... 549/496
5,292,922 A * 3/1994 Takematsu et al. ........... 560/47
5,468,719 A * 11/1995 Takematsu et al. ......... 504/224
5,481,022 A * 1/1996 Takematsu et al. ........... 560/45
5,506,190 A * 4/1996 Hirai et al. .................. 504/224

FOREIGN PATENT DOCUMENTS

JP 48-44425 * 6/1973
JP 5-230034 * 9/1993

* cited by examiner

Primary Examiner—Peter O'Sullivan
(74) Attorney, Agent, or Firm—Crowell & Moring LLP

(57) ABSTRACT

The invention provides N-phenyltetrahydrophthalamic acid derivatives represented by the general formula [I], methods of producing the same, herbicides containing the same as the effective components, imidoylchloride derivatives as the intermediate products and methods of producing the same,

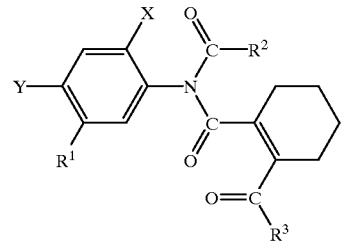

wherein X and Y each individually represent hydrogen atoms or halogen atoms, $R^1$ represents a lower alkoxycarbonylalkylthio group, $R^2$ represents a lower alkyl group, a halogenated lower alkyl group or a substituted or unsubstituted phenyl group, and $R^3$ represents a lower alkoxy group, a lower alkenyloxy group, a lower alkynyloxy group, or a lower alkoxyalkoxy group. The herbicides of the present invention, which are very useful, can be widely applied to upland, paddy field, orchard, turf, forest, non-crop land, etc., and are not harmful to crops.

4 Claims, No Drawings

N-PHENYLTETRAHYDROPHTHALAMIC ACID DERIVATIVES, METHODS OF PRODUCING SAME, AND HERBICIDES CONTAINING SAME AS EFFECTIVE COMPONENTS

This application is a division of application Ser. No. 08/676,148, filed Jul. 15, 1996 now U.S. Pat. No. 5,801,122, which is a national stage of PCT/J95/00044 filed Jan. 19, 1995.

TECHNOLOGICAL FIELD

This invention relates to herbicides, and more particularly to N-phenyltetrahydrophthalamic acid derivatives which are novel compounds, to methods of producing the same, and to herbicides containing the same as the effective components, and to imidoylchloride derivatives as the intermediate products, and to methods of producing the same. N-phenyltetrahydrophthalamic acid derivatives of the present invention exhibit excellent herbicidal activity. The derivatives are useful as herbicides which can be widely applied to upland, paddy field, orchard, pasture, turf, forest, non-crop land, etc. The derivatives are not harmful to crops.

BACKGROUND TECHNOLOGY

Hitherto, herbicidal activity of tetrahydrophthalamic acid derivatives is well known. For example, N-(4'-chlorophenyl)-3, 4, 5, 6-tetrahydrophthalamic acid methyl ester is known, as is disclosed in JP-A-48-44425.

However, the conventional tetrahydrophthalamic acid derivatives are not necessarily sufficient in herbicidal activity or are substantially limited in herbicidal spectrum against weeds. Furthermore, these derivatives are insufficient in selectivity between crops and weeds, thereby inducing problems of safety for crops.

It is an object of the present invention to solve the aforementioned problems, and to provide novel compounds which are excellent in herbicidal activity but not harmful to crops, methods of producing the same and herbicides containing the same as the effective components, and the intermediate products and method of producing the same.

DISCLOSURE OF THE INVNTION

The inventors have found and already proposed that novel tetrahydrophthalamic acid derivatives each having a specific substituent acyl group bonded to an amide nitrogen atom are very excellent in herbicidal activity, selectivity and herbicidal spectrum (International Application PCT/JP91/01109). In view of this, the inventors have intensely studied and as a result have completed the present invention as follows.

That is, the present invention provides N-phenyltetrahydrophthalamic acid derivatives represented by the general formula [I], methods of producing the same, and herbicides containing the same as the effective components:

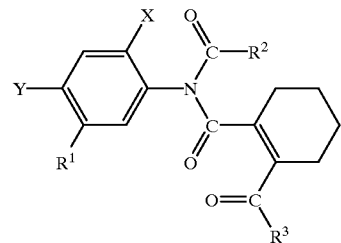

wherein X and Y each individually represent hydrogen atoms or halogen atoms, $R^1$ represents a lower alkoxycarbonylalkylthio group, $R^2$ represents a lower alkyl group, a halogenated lower alkyl group or a substituted or unsubstituted phenyl group, and $R^3$ represents a lower alkoxy group, a lower alkenyloxy group, a lower alkynyloxy group, or a lower alkoxyalkoxy group.

Furthermore, the present invention provides N-phenyltetrahydrophthalamic acid derivatives represented by the general formula [II], methods of producing the same, and herbicides containing the same as the effective components:

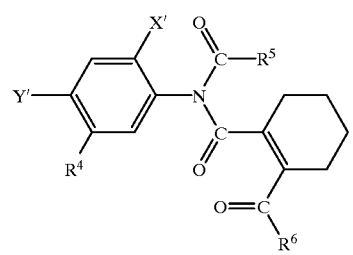

wherein X' and Y' each individually represent hydrogen atoms or halogen atoms, $R^4$ represents a hydrogen atom, a lower alkoxy group, a lower alkenyloxy group, a lower alkynyloxy group, cycloalkyloxy group, a lower alkoxycarbonyl group, a lower alkoxycarbonylalkoxy group or a lower alkoxycarbonylalkylthio group, $R^5$ represents:

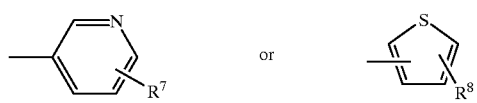

wherein $R^7$ represents a hydrogen atom, a halogen atom, a lower alkyl group or a lower alkoxycarbonyl group, and $R^8$ represents a hydrogen atom, a halogen atom or a lower alkyl group, and $R^6$ represents a lower alkoxy group, a lower alkenyloxy group, a lower alkynyloxy group, a cycloalkyloxy group or a lower alkoxyalkoxy group.

Still furthermore, the present invention provides imidoylchloride derivatives represented by the general formula [III] and method of producing the same:

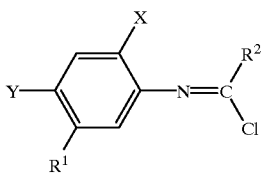

wherein X and Y each individually represent hydrogen atoms or halogen atoms, $R^1$ represents a lower alkoxycarbonylalkylthio group, and $R^2$ represents a lower alkyl group, a halogenated lower alkyl group or a substituted or unsubstituted phenyl group.

Furthermore, the present invention provides imidoylchloride derivatives represented by the general formula [IV] and method of producing the same:

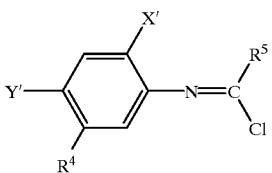

wherein X' and Y' each individually represent hydrogen atoms or halogen atoms, $R^4$ represents a hydrogen atom, a lower alkoxy group, a lower alkenyloxy group, a lower alkynyloxy group, cycloalkyloxy group, a lower alkoxycarbonyl group, a lower alkoxycarbonylalkoxy group or a lower alkoxycarbonylalkylthio group, $R^5$ represents:

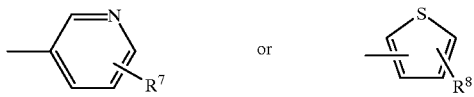

wherein $R^7$ represents a hydrogen atom, a halogen atom, a lower alkyl group or a lower alkoxycarbonyl group, and $R^8$ represents a hydrogen atom, a halogen atom or a lower alkyl group.

As concrete examples of N-phenyltetrahydrophthalamic acid derivatives [I] which are compounds of the present invention are, there can be cited, for example, N-acetyl-N-(4-chloro-2-fluoro-5-methoxycarbonylmethylthiophenyl)-3,4,5,6-tetrahydrophthalamic acid methyl ester, N-acetyl-N-(4-chloro-2-fluoro-5-methoxycarbonylmethylthiophenyl)-3,4,5,6-tetrahydrophthalamic acid ethyl ester, N-acetyl-N-(4-chloro-2-fluoro-5-methoxycarbonylmethylthiophenyl)-3,4,5,6-tetrahydrophthalamic acid-n-propyl ester, N-acetyl-N-(4-chloro-2-fluoro-5-methoxycarbonylmethylthiophenyl)-3,4,5,6-tetrahydrophthalamic acid-iso-propyl ester, N-acetyl-N-(4-chloro-2-fluoro-5-methoxycarbonylmethylthiophenyl)-3,4,5,6-tetrehydrophthalamic acid-n-butyl ester, N-acetyl-N-(4-chloro-2-fluoro-5-methoxycarbonylmethylthiophenyl)-3,4,5,6-tetrahydrophthalamic acid-n-pentyl ester, N-acetyl-N-(4-chloro-2-fluoro-5-methoxycarbonylmethylthiophenyl)-3,4,5,6-tetrahydrophthalamic acid allyl ester, N-acetyl-N-(4-chloro-2-fluoro-5-methoxycarbonylmethylthiophenyl)-3,4,5,6-tetrehydrophthalamic acid propargyl ester, N-acetyl-N-(4-chloro-2-fluoro-5-methoxycarbonylmethylthiophenyl)-3,4,5,6-tetrahydrophthalamic acid methoxymethyl ester, N-acetyl-N-(4-chloro-2-fluoro-5-methoxycarbonylmethylthiophenyl)-3,4,5,6-tetrahydrophthalamic acid ethoxymethyl ester, N-acetyl-N-(4-chloro-2-fluoro-5-methoxycarbonylmethylthiophenyl)-3,4,5,6-tetrahydrophthalamic acid-2-methoxyethyl ester, N-acetyl-N-(4-chloro-2-fluoro-5-methoxycarbonylmethylthiophenyl)-3,4,5,6-tetrahydrophthalamic acid-2-ethoxyethyl ester, N-propionyl-N-(4-chloro-2-fluoro-5-methoxycarbonylmethylthiophenyl)-3,4,5,6-tetrahydrophthalamic acid methyl ester, N-propionyl-N-(4-chloro-2-fluoro-5-methoxycarbonylmethylthiophenyl)-3,4,5,6-tetrahydrophthalamic acid ethyl ester, N-propionyl-N-(4-chloro-2-fluoro-5-methoxycarbonylmethylthiophenyl)-3,4,5,6-tetrahydrophthalamic acid-n-propyl ester, N-propionyl-N-(4-chloro-2-fluoro-5-methoxycarbonylmethylthiophenyl)-3,4,5,6-tetrehydrophthalamic acid-iso-propyl ester, N-propionyl-N-(4-chloro-2-fluoro-5-methoxycarbonylmethylthiophenyl)-3,4,5,6-tetrehydrophthalamic acid-n-butyl ester, N-propionyl-N-(4-chloro-2-fluoro-5-methoxycarbonylmethylthiophenyl)-3,4,5,6-tetrehydrophthalamic acid-n-pentyl ester, N-propionyl-N-(4-chloro-2-fluoro-5-methoxycarbonylmethylthiophenyl)-3,4,5,6-tetrahydrophthalamic acid allyl ester, N-propionyl-N-(4-chloro-2-fluoro-5-methoxycarbonylmethylthiophenyl)-3,4,5,6-tetrehydrophthalamic acid propargyl ester, N-propionyl-N-(4-chloro-2-fluoro-5-methoxycarbonylmethylthiophenyl)-3,4,5,6-tetrehydrophthalamic acid methoxymethyl ester, N-propionyl-N-(4-chloro-2-fluoro-5-methoxycarbonylmethylthiophenyl)-3,4,5,6-tetrahydrophthalamic acid ethoxymethyl ester, N-propionyl-N-(4-chloro-2-fluoro-5-methoxycarbonylmethylthiophenyl)-3,4,5,6-tetrahydrophthalamic acid-2-methoxyethyl ester, N-propionyl-N-(4-chloro-2-fluoro-5-methoxycarbonylmethylthiophenyl)-3,4,5,6-tetrahydrophthalamic acid-2-ethoxyethyl ester, N-(2-chloroacetyl)-N-(4-chloro-2-fluoro-5-methoxycarbonylmethylthiophenyl)-3,4,5,6-tetrahydrophthalamic acid methyl ester, N-(2-chloroacetyl)-N-(4-chloro-2-fluoro-5-methoxycarbonylmethylthiophenyl)-3,4,5,6-tetrahydrophthalamic acid ethyl ester, N-(2-chloroacetyl)-N-(4-chloro-2-fluoro-5-methoxycarbonylmethylthiophenyl)-3,4,5,6-tetrehydrophthalamic acid-n-propyl ester, N-(2-chloroacetyl)-N-(4-chloro-2-fluoro-5-methoxycarbonylmethylthiophenyl)-3,4,5,6-tetrahydrophthalamic acid-iso-propyl ester, N-(2-chloroacetyl)-N-(4-chloro-2-fluoro-5-methoxycarbonylmethylthiophenyl)-3,4,5,6-tetrahydrophthalamic acid-n-butyl ester, N-(2-chloroacetyl)-N-(4-chloro-2-fluoro-5-methoxycarbonylmethylthiophenyl)-3,4,5,6-tetrahydrophthalamic acid-n-pentyl ester, N-(2-chloroacetyl)-N-(4-chloro-2-fluoro-5-methoxycarbonylmethylthiophenyl)-3,4,5,6-tetrahydrophthalamic acid allyl ester, N-(2-chloroacetyl)-N-(4-chloro-2-fluoro-5-methoxycarbonylmethylthiophenyl)-3,4,5,6-tetrahydrophthalamic acid propargyl ester, N-(2-chloroacetyl)-N-(4-chloro-2-fluoro-5-methoxycarbonylmethylthiophenyl)-3,4,5,6-tetrahydrophthalamic acid methoxymethyl ester, N-(2-chloroacetyl)-N-(4-chloro-2-fluoro-5-methoxycarbonylmethylthiophenyl)-3,4,5,6-tetrahydrophthalamic acid ethoxymethyl ester, N-(2-chloroacetyl)-N-(4-chloro-2-fluoro-5- methoxycarbonylmethylthiophenyl)-3,4,5,6-tetrahydrophthalamic acid-2-methoxyethyl ester, N-(2-chloroacetyl)-N-(4-chloro-2-fluoro-5-methoxycarbonylmethylthiophenyl)-3,4,5,6-tetrahydrophthalamic acid-2-ethoxyethyl ester, N-benzoyl-N-(4-chloro-2-fluoro-5-methoxycarbonylmethylthiophenyl)-3,4,5,6-tetrahydrophthalamic acid methyl ester, N-benzoyl-N-(4-chloro-2-fluoro- 5-methoxycarbonylmethylthiophenyl)-3,4,5,6-tetrehydrophthalamic acid ethyl ester, N-benzoyl-N-(4-chloro-2-fluoro-5-methoxycarbonylmethylthiophenyl)-3,4,5,6-tetrehydrophthalamic acid-n-propyl ester, N-benzoyl-N-(4-chloro-2-fluoro-5-methoxycarbonylmethylthiophenyl)-3,4,5,6-tetrehydrophthalamic acid-iso-propyl ester, N-benzoyl-N-(4-chloro-2-fluoro-5-methoxycarbonylmethylthiophenyl)-3,4,5,6-tetrahydrophthalamic acid-n-butyl ester, N-benzoyl-N-(4-chloro-2-fluoro-5-methoxycarbonylmethylthiophenyl)-3,4,5,6-tetrahydrophthalamic acid-n-pentyl ester, N-benzoyl-N-(4-chloro-2-fluoro-5-methoxycarbonylmethylthiophenyl)-3,4,5,6-tetrahydrophthalamic acid allyl ester, N-benzoyl-N-(4-chloro-2-fluoro-5-methoxycarbonylmethylthiophenyl)-3,4,5,6-tetrahydrophthalamic acid propargyl ester, N-benzoyl-N-(4-chloro-2-fluoro-5-methoxycarbonylmethylthiophenyl)-3,4,5,6-tetrahydrophthalamic acid methoxymethyl ester, N-benzoyl-N-(4-chloro-2-fluoro-5-methoxycarbonylmethylthiophenyl)-3,4,5,6-tetrahydrophthalamic acid ethoxymethyl ester, N-benzoyl-N-(4-chloro-2-fluoro-5-methoxycarbonylmethylthiophenyl)-3,4,5,6-tetrahydrophthalamic acid-2-methoxyethyl ester, N-benzoyl-N-(4-chloro-2-fluoro-5-methoxycarbonylmethylthiophenyl)-3,4,5,6-tetrahydrophthalamic acid-2-ethoxyethyl ester, N-(3-fluorobenzoyl)-N-(4-chloro-2-fluoro-5-methoxycarbonylmethylthiophenyl)-3,4,5,6-tetrahydrophthalamic acid methyl ester, N-(3-fluorobenzoyl)-N-(4-chloro-2-fluoro-5-methoxycarbonylmethylthiophenyl)-3,4,5,6-tetrahydrophthalamic acid ethyl ester, N-(3-fluorobenzoyl)-N-(4-chloro-2-fluoro-5-methoxycarbonylmethylthiophenyl)-3,4,5,6-tetrehydrophthalamic acid-n-propyl ester, N-(3-fluorobenzoyl)-N-(4-chloro-2-fluoro-5-methoxycarbonylmethylthiophenyl)-3,4,5,6-tetrahydrophthalamic acid-iso-propyl ester, N-(3-fluorobenzoyl)-N-(4-chloro-2-fluoro-5-methoxycarbonylmethylthiophenyl)-3,4,5,6-tetrahydrophthalamic acid-n-butyl ester, N-(3-fluorobenzoyl)-N-(4-chloro-2-fluoro-5-methoxycarbonylmethylthiophenyl)-3,4,5,6-tetrahydrophthalamic acid-n-pentyl ester, N-(3-fluorobenzoyl)-N-(4-chloro-2-fluoro-5-methoxycarbonylmethylthiophenyl)-3,4,5,6-tetrahydrophthalamic acid allyl ester, N-(3-fluorobenzoyl)-N-(4-chloro-2-fluoro-5-methoxycarbonylmethylthiophenyl)-3,4,5,6-tetrahydrophthalamic acid propargyl ester, N-(3-fluorobenzoyl)-N-(4-chloro-2-fluoro-5-methoxycarbonylmethylthiophenyl)-3,4,5,6-tetrahydrophthalamic acid methoxymethyl ester, N-(3-fluorobenzoyl)-N-(4-chloro-2-fluoro-5-methoxycarbonylmethylthiophenyl)-3,4,5,6-tetrahydrophthalamic acid ethoxymethyl ester, N-(3-fluorobenzoyl)-N-(4-chloro-2-fluoro-5-methoxycarbonylmethylthiophenyl)-3,4,5,6-tetrahydrophthalamic acid-2-methoxyethyl ester, N-(3-fluorobenzoyl)-N-(4-chloro-2-fluoro-5-methoxycarbonylmethylthiophenyl)-3,4,5,6-tetrahydrophthalamic acid-2-ethoxyethyl ester, N-acetyl-N-(4-chloro-2-fluoro-5-ethoxycarbonylmethylthiophenyl)-3,4,5,6-tetrahydrophthalamic acid methyl ester, N-acetyl-N-(4-chloro-2-fluoro-5-ethoxycarbonylmethylthiophenyl)-3,4,5,6-tetrehydrophthalamic acid ethyl ester, N-acetyl-N-(4-chloro-2-fluoro-5-ethoxycarbonylmethylthiophenyl)-3,4,5,6-tetrehydrophthalamic acid-n-propyl ester, N-acetyl-N-(4-chloro-2-2-fluoro-5-ethoxycarbonylmethylthiophenyl)-3,4,5,6-tetrehydrophthalamic acid-iso-propyl ester, N-acetyl-N-(4-chloro-2-fluoro-5-ethoxycarbonylmethylthiophenyl)-3,4,5,6-tetrahydrophthalamic acid-n-butyl ester, N-acetyl-N-(4-chloro-2-fluoro-5-ethoxycarbonylmethylthiophenyl)-3,4,5,6-tetrahydrophthalamic acid-n-pentyl ester, N-acetyl-N-(4-chloro-2-fluoro-5-ethoxycarbonylmethylthiophenyl)-3,4,5,6-tetrahydrophthalamic acid allyl ester, N-acetyl-N-(4-chloro-2-fluoro-5-ethoxycarbonylmethylthiophenyl)-3,4,5,6-tetrahydrophthalamic acid propargyl ester, N-acetyl-N-(4-chloro-2-fluoro-5-ethoxycarbonylmethylthiophenyl)-3,4,5,6-tetrahydrophthalamic acid methoxymethyl ester, N-acetyl-N-(4-chloro-2-fluoro-5-ethoxycarbonylmethylthiophenyl)-3,4,5,6-tetrahydrophthalamic acid ethoxymethyl ester, N-acetyl-N-(4-chloro-2-fluoro-5-ethoxycarbonylmethylthiophenyl)-3,4,5,6-tetrahydrophthalamic acid-2-methoxyethyl ester, N-acetyl-N-(4-chloro-2-fluoro-5-ethoxycarbonylmethylthiophenyl)-3,4,5,6-tetrahydrophthalamic acid-2-ethoxyethyl ester, N-propionyl-N-(4-chloro-2-fluoro-5-ethoxycarbonylmethylthiophenyl)-3,4,5,6-tetrahydrophthalamic acid methyl ester, N-propionyl-N-(4-chloro-2-fluoro-5-ethoxycarbonylmethylthiophenyl)-3,4,5,6-tetrehydrophthalamic acid ethyl ester, N-propionyl-N-(4-chloro-2-fluoro-5-ethoxycarbonylmethylthiophenyl)-3,4,5,6-tetrehydrophthalamic acid-n-propyl ester, N-propionyl-N-(4-chloro-2-fluoro-5-ethoxycarbonylmethylthiophenyl)-3,4,5,6-tetrehydrophthalamic acid-iso-propyl ester, N-propionyl-N-(4-chloro-2-fluoro-5-ethoxycarbonylmethylthiophenyl)-3,4,5,6-tetrahydrophthalamic acid-n-butyl ester, N-propionyl-N-(4-chloro-2-fluoro-5-ethoxycarbonylmethylthiophenyl)-3,4,5,6-tetrahydrophthalamic acid-n-pentyl ester, N-propionyl-N-(4-chloro-2-fluoro-5-ethoxycarbonylmethylthiophenyl)-3,4,5,6-tetrahydrophthalamic acid allyl ester, N-propionyl-N-(4-chloro-2-fluoro-5-ethoxycarbonylmethylthiophenyl)-3,4,5,6-tetrahydrophthalamic acid propargyl ester, N-propionyl-N-(4-chloro-2-fluoro-5-ethoxycarbonylmethylthiophenyl)-3,4,5,6-tetrahydrophthalamic acid methoxymethyl ester, N-propionyl-N-(4-chloro-2-fluoro-5-ethoxycarbonylmethylthiophenyl)-3,4,5,6-tetrahydrophthalamic acid ethoxymethyl ester, N-propionyl-N-(4-chloro-2-fluoro-5-ethoxycarbonylmethylthiophenyl)-3,4,5,6-tetrahydrophthalamic acid-2-methoxyethyl ester, N-propionyl-N-(4-chloro-2-fluoro-5-ethoxycarbonylmethylthiopheny)-3,4,5,6-tetrahydrophthalamic acid-2-ethoxyethyl ester, N-(2-chloroacetyl)-N-(4-chloro-2-fluoro-5-ethoxycarbonylmethylthiophenyl)-3,4,5,6-tetrahydrophthalamic acid methyl ester, N-(2-chloroacetyl)-N-(4-chloro-2-fluoro-5-ethoxycarbonylmethylthiophenyl)-3,4,5,6-tetrahydrophthalamic acid ethyl ester, N-(2-chloroacetyl)-N-(4-chloro-2-fluoro-5-ethoxycarbonylmethylthiophenyl)-3,4,5,6-tetrahydrophthalamic acid-n-propyl ester, N-(2-chloroacetyl)-N-(4-chloro-2-fluoro-5-ethoxycarbonymethylthiophenyl)-3,4,5,6- tetrahydrophthalamic acid-iso-propyl ester, N-(2-chloroacetyl)-N-(4-chloro-2-fluoro-5-ethoxycarbonylmethylthiophenyl)-3,4,5,6-tetrahydrophthalamic acid-n-butyl ester, N-(2-chloroacetyl)-N-(4-chloro-2-fluoro-5-ethoxycarbonylmethylthiophenyl)-3,4,5,6-tetrahydrophthalamic acid-n-pentyl ester, N-(2-chloroacetyl)-N-(4-chloro-2-fluoro-5-ethoxycarbonylmethylthiophenyl)-3,4,5,6-tetrahydrophthalamic acid allyl ester, N-(2-chloroacetyl)-N-(4-chloro-2-fluoro-5-ethoxycarbonylmethylthiophenyl)-3,4,5,6-tetrahydrophthalamic acid propargyl ester, N-(2-chloroacetyl)-N-(4-chloro-2-fluoro-5-ethoxycarbonylmethylthiophenyl)-3,4,5,6-tetrahydrophthalamic acid methoxymethyl ester, N-(2-chloroacetyl)-N-(4-chloro-2-fluoro-5-ethoxycarbonylmethylthiophenyl)-3,4,5,6-tetrahydrophthalamic acid ethoxymethyl ester, N-(2-chloroacetyl)-N-(4-chloro-2-fluoro-5-ethoxycarbonylmethylthiophenyl)-3,4,5,6-tetrehydrophthalamic acid-2-methoxyethyl ester, N-(2-chloroacetyl)-N-(4-chloro-2-fluoro-5-ethoxycarbonylthiophenyl)-3,4,5,6-tetrahydrophthalamic acid-2-ethoxyethyl ester, N-benzoyl-N-(4-chloro-2-fluoro-5-ethoxycarbonylmethylthiophenyl)-3,4,5,6-tetrahydrophthalamic acid methyl ester, N-benzoyl-N-(4-chloro-2-fluoro-5-ethoxycarbonylmethylthiophenyl)-3,4,5,6-tetrahydrophthalamic acid ethyl ester, N-benzoyl-N-(4-chloro-2-fluoro-5-ethoxycarbonylmethylthiophenyl)-3,4,5,6-tetrahydrophthalamic acid-n-propyl ester, N-benzoyl-N-(4-chloro-2-fluoro-5-ethoxycarbonylmethylthiophenyl)-3,4,5,6-tetrahydrophthalamic acid-iso-propyl ester, N-benzoyl-N-(4-chloro-2-fluoro-5-ethoxycarbonylmethylthiophenyl)-3,4,5,6-tetrahydrophthalamic acid-n-butyl ester, N-benzoyl-N-(4-chloro-2-fluoro-5-ethoxycarbonylmethylthiophenyl)-3,4,5,6-tetrahydrophthalamic acid-n-pentyl ester, N-benzoyl-N-(4-chloro-2-fluoro-5-ethoxycarbonylmethylthiophenyl)-3,4,5,6-tetrahydrophthalamic acid allyl ester, N-benzoyl-N-(4-chloro-2-fluoro-5-ethoxycarbonylmethylthiophenyl)-3,4,5,6-tetrahydrophthalamic acid propargyl ester, N-benzoyl-N-(4-chloro-2-fluoro-5-ethoxycarbonylmethylthiophenyl)-3,4,5,6-tetrehydrophthalamic acid methoxymethyl ester, N-benzoyl-N-(4-chloro-2-fluoro-5-ethoxycarbonylmethylthiophenyl)-3,4,5,6-tetrehydrophthalamic acid ethoxymethyl ester, N-benzoyl-N-(4-chloro-2-fluoro-5-ethoxycarbonylmethylthiophenyl)-3,4,5,6-tetrahydrophthalamic acid-2-methoxyethyl ester, N-benzoyl-N-(4-chloro-2-fluoro-5-ethoxycarbonylmethylthiophenyl)-3,4,5,6-tetrehydrophthalamic acid-2-ethoxyethyl ester, N-(3-fluorobenzoyl)-N-(4-chloro-2-fluoro-5-ethoxycarbonylmethylthiophenyl)-3,4,5,6-tetrahydrophthalamic acid methyl ester, N-(3-fluorobenzoyl)-N-(4-chloro-2-fluoro-5-ethoxycarbonylmethylthiophenyl)-3,4,5,6-tetrahydrophthalamic acid ethyl ester, N-(3-fluorobenzoyl)-N-(4-chloro-2-fluoro-5-ethoxycarbonylmethylthiophenyl)-3,4,5,6-tetrahydrophthalamic acid-n-propyl ester, N-(3-fluorobenzoyl)-N-(4-chloro-2-fluoro-5-ethoxycarbonylmethylthiophenyl)-3,4,5,6-tetrahydrophthalamic acid-iso-propyl ester, N-(3-fluorobenzoyl)-N-(4-chloro-2-fluoro-5-ethoxycarbonylmethylthiophenyl)-3,4,5,6-tetrahydrophthalamic acid-n-butyl ester, N-(3-fluorobenzoyl)-N-(4-chloro-2-fluoro-5-ethoxycarbonylmethylthiophenyl)-3,4,5,6-tetrahydrophthalamic acid-n-pentyl ester, N-(3-fluorobenzoyl)-N-(4-chloro-2-fluoro-5-ethoxycarbonylmethylthiophenyl)-3,4,5,6-tetrahydrophthalamic acid allyl ester, N-(3-fluorobenzoyl)-N-(4-chloro-2-fluoro-5-ethoxycarbonylmethylthiophenyl)-3,4,5,6-tetrahydrophthalamic acid propargyl ester, N-(3-fluorobenzoyl)-N-(4-chloro-2-fluoro5-ethoxycarbonylmethylthiophenyl)-3,4,5,6-tetrahydrophthalamic acid methoxymethyl ester, N-(3-fluorobenzoyl)-N-(4-chloro-2-fluoro-5-ethoxycarbonylmethylthiophenyl)-3,4,5,6-tetrehydrophthalamic acid ethoxymethyl ester, N-(3-fluorobenzoyl)-N-(4-chloro-2-fluoro-5-ethoxycarbonylmethylthiophenyl)-3,4,5,6-tetrahydrophthalamic acid-2-methoxyethyl ester, N-(3-fluorobenzoyl)-N-(4-chloro-2-fluoro-5-ethoxycarbonylmethylthiophenyl)-3,4,5,6-tetrahydrophthalamic acid-2-ethoxyethyl ester, N-acetyl-N-[4-chloro-2-fluoro-5-(n-butoxcarbonylmethylthio)phenyl]-3,4,5,6-tetrahydrophthalamic acid methyl ester, N-acetyl-N-[4-chloro-2-fluoro-5-(n-butoxcarbonylmethylthio)phenyl]-3,4,5,6-tetrahydrophthalamic acid ethyl ester,-N-acetyl-N-[4-chloro-2-fluoro-5-(n-butoxcarbonylmethylthio)phenyl]-3,4,5,6-tetrahydrophthalamic acid-n-propyl ester, N-acetyl-N-[4-chloro-2-fluoro-5-(n-butoxcarbonylmethylthio)phenyl]-3,4,5,6-tetrahydrophthalamic acid-iso-propyl ester, N-acetyl-N-[4-chloro-2-fluoro-5-(n-butoxcarbonylmethylthio)phenyl]-3,4,5,6-tetrahydrophthalamic acid-n-butyl ester, N-acetyl-N-[4-chloro-2-fluoro-5-(n-butoxcarbonylmethylthio)phenyl]-3,4,5,6-tetrahydrophthalamic acid-n-pentyl ester, N-acetyl-N-[4-chloro-2-fluoro-5-(n-butoxcarbonylmethylthio)phenyl]-3,4,5,6-tetrahydrophthalamic acid allyl ester, N-acetyl-N-[4-chloro-2-fluoro-5-(n-butoxcarbonyl-methylthio)phenyl]-3,4,5,6-tetrahydrophthalamic acid propargyl ester, N-acetyl-N-[4-chloro-2-fluoro5-(n-butoxycarbonylmethylthio)phenyl]-3,4,5,6-tetrahydrophthalamic acid methoxymethyl ester, N-acetyl-N-[4-chloro-2-fluoro-5-(n-butoxycarbonylmethylthio)phenyl]-3,4,5,6-tetrahydrophthalamic acid ethoxymethyl ester, N-acetyl-N-[4-chloro-2-fluoro-5-(n-butoxycarbonylmethylthio)phenyl]-3,4,5,6-tetrahydrophthalamic acid-2-methoxyethyl ester, N-acetyl-N-[4-chloro-2-fluoro-5-(n-butoxycarbonylmethylthio)phenyl]-3,4,5,6-tetrehydrophthalamic acid-2-ethoxyethyl ester, N-propionyl-N-[4-chloro-2-fluoro-5-(n-butoxycarbonylmethylthio)phenyl]-3,4,5,6-tetrahydrophthalamic acid methyl ester, N-propionyl-N-[4-chloro-2-fluoro-5-(n-butoxycarbonylmethylthio)phenyl]-3,4,5,6-tetrahydrophthalamic acid ethyl ester, N-propionyl-N-[4-chloro-2-fluoro-5-(n-butoxycarbonylmethylthio)phenyl]-3,4,5,6-tetrahydrophthalamic acid-n-propyl ester, N-propionyl-N-[4-chloro-2-fluoro-5-(n-butoxycarbonylmethylthio)phenyl]-3,4,5,6-tetrahydrophthalamic acid-iso-propyl ester, N-propionyl-N-[4-chloro-2-fluoro-5-(n-butoxycarbonylmethylthio)phenyl]-3,4,5,6-tetrahydrophthalamic acid-n-butyl ester, N-propionyl-N-[4-chloro-2-fluoro-5-(n-butoxycarbonylmethylthio)phenyl]-3,4,5,6-tetrehydrophthalamic acid-n-pentyl ester, N-propionyl-N-[4-chloro-2-fluoro-5-(n-butoxycarbonylmethylthio)phenyl]-3,4,5,6-tetrehydrophthalamic acid allyl ester, N-propionyl-N-[4-chloro-2-fluoro-5-(n-butoxycarbonylmethylthio)phenyl]-3,4,5,6-tetrehydrophthalamic acid propargyl ester, N-propionyl-N-[4-chloro-2-fluoro-5-(n-butoxycarbonylmethylthio)phenyl]-3,4,5,6-tetrehydrophthalamic acid methoxymethyl ester, N-propionyl-N-[4-chloro-2-fluoro-5-(n- butoxycarbonylmethylthio)phenyl]-3,4,5,6-tetrahydrophthalamic acid ethoxymethyl ester, N-propionyl-N-[4-chloro-2-fluoro-5-(n-butoxycarbonylmethylthio)phenyl]-3,4,5,6-tetrahydrophthalamic acid-2-methoxyethyl ester, N-propionyl-N-[4-chloro-2-fluoro-5-(n-butoxycarbonylmethylthio)phenyl]-3,4,5,6-tetrahydrophthalamic acid-2-ethoxyethyl ester, N-(2-chloroacetyl)-N-[4-chloro-2-fluoro-5-(n-butoxcarbonylmethylthio)phenyl]-3,4,5,6-tetrahydrophthalamic acid methyl ester, N-(2-chloroacetyl)-N-[4-chloro-2-fluoro-5-(n-butoxcarbonylmethylthio)phenyl]-3,4,5,6-tetrahydrophthalamic acid ethyl ester, N-(2-chloroacetyl)-N-[4-chloro-2-fluoro-5-(n-butoxcarbonylmethylthio)phenyl]-3,4,5,6-tetrahydrophthalamic acid-n-propyl ester, N-(2-chloroacetyl)-N-[4-chloro-2-fluoro-5-(n-butoxycarbonylmethylthio)phenyl]-3,4,5,6-tetrahydrophthalamic acid-iso-propyl ester, N-(2-chloroacetyl)-N-[4-chloro-2-fluoro-5-(n-butoxycarbonylmethylthio)phenyl]-3,4,5,6-tetrahydrophthalamic acid-n-butyl ester, N-(2-chloroacetyl)-N-[4-chloro-2-fluoro-5-(n-butoxycarbonylmethylthio)phenyl]-3,4,5,6-tetrahydrophthalamic acid-n-pentyl ester, N-(2-chloroacetyl)-N-[4-chloro-2-fluoro-5-(n-butoxycarbonylmethylthio)phenyl]-3,4,5,6-tetrahydrophthalamic acid allyl ester, N-(2-chloroacetyl)-N-[4-chloro-2-fluoro-5-(n-butoxycarbonylmethylthio)phenyl]-3,4,5,6-tetrahydrophthalamic acid propargyl ester, N-(2-chloroacetyl)-N-[4-chloro-2-fluoro-5-(n-butoxycarbonylmethylthio)phenyl]-3,4,5,6-tetrahydrophthalamic acid methoxymethyl ester, N-(2-chloroacetyl)-N-[4-chloro-2-fluoro-5-(n-butoxycarbonylmethylthio)phenyl]-3,4,5,6-tetrahydrophthalamic acid ethoxymethyl ester, N-(2-chloroacetyl)-N-[4-chloro-2-fluoro-5-(n-butoxycarbonylmethylthio)phenyl]-3,4,5,6-tetrahydrophthalamic acid-2-methoxyethyl ester, N-(2-chloroacetyl)-N-[4-chloro-2-fluoro-5-(n-butoxycarbonylmethylthio)phenyl]-3,4,5,6-tetrahydrophthalamic acid-2-ethoxyethyl ester, N-benzoyl-N-[4-chloro-2-fluoro-5-(n-butoxycarbonylmethylthio)phenyl]-3,4,5,6-tetrahydrophthalamic acid methyl ester, N-benzoyl-N-[4-chloro-2-fluoro-5-(n-butoxycarbonylmethylthio)phenyl]-3,4,5,6-tetrahydrophthalamic acid ethyl ester, N-benzoyl-N-[4-chloro-2-fluoro-5-(n-butoxycarbonylmethylthio)phenyl]-3,4,5,6-tetrahydrophthalamic acid-n-propyl ester, N-benzoyl-N-[4-chloro-2-fluoro-5-(n-butoxycarbonylmethylthio)phenyl]-3,4,5,6-tetrahydrophthalamic acid-iso-propyl ester, N-benzoyl-N-[4-chloro-2-fluoro-5-(n-butoxycarbonylmethylthio)phenyl]-3,4,5,6-tetrahydrophthalamic acid-n-butyl ester, N-benzoyl-N-[4-chloro-2-fluoro-5-(n-butoxycarbonylmethylthio)phenyl]-3,4,5,6-tetrahydrophthalamic acid-n-pentyl ester, N-benzoyl-N-[4-chloro-2-fluoro-5-(n-butoxycarbonylmethylthio)phenyl]-3,4,5,6-tetrahydrophthalamic acid allyl ester, N-benzoyl-N-[4-chloro-2-fluoro-5-(n-butoxycarbonylmethylthio)phenyl]-3,4,5,6-tetrahydrophthalamic acid propargyl ester, N-benzoyl-N-[4-chloro-2-fluoro-5-(n-butoxycarbonylmethylthio)phenyl]-3,4,5,6-tetrahydrophthalamic acid methoxymethyl ester, N-benzoyl-N-[4-chloro-2-fluoro-5-(n-butoxycarbonylmethylthio)phenyl]-3,4,5,6-tetrahydrophthalamic acid ethoxymethyl ester, N-benzoyl-N-[4-chloro-2-fluoro-5-(n-butoxycarbonylmethylthio)phenyl]-3,4,5,6-tetrahydrophthalamic acid-2-methoxyethyl ester, N-benzoyl-N-[4-chloro-2-fluoro-5-(n-butoxcarbonylmethylthio)phenyl]-3,4,5,6-tetrahydrophthalamic acid-2-ethoxyethyl ester, N-(3-fluorobenzoyl)-N-[4-chloro-2-fluoro-5-(n-butoxycarbonylmethylthio)phenyl]-3,4,5,6-tetrehydrophthalamic acid methyl ester, N-(3-fluorobenzoyl)-N-[4-chloro-2-fluoro-5-(n-butoxycarbonylmethylthio)phenyl]-3,4,5,6-tetrahydrophthalamic acid ethyl ester, N-(3-fluorobenzoyl)-N-[4-chloro-2-fluoro-5-(n-butoxycarbonylmethylthio)phenyl]-3,4,5,6-tetrahydrophthalamic acid-n-propyl ester, N-(3-fluorobenzoyl)-N-[4-chloro-2-fluoro-5-(n-butoxycarbonylmethylthio)phenyl]-3,4,5,6-tetrahydrophthalamic acid-iso-propyl ester, N-(3-fluorobenzoyl)-N-[4-chloro-2-fluoro- 5-(n-butoxcarbonylmethylthio)phenyl]-3,4,5,6-tetrahydrophthalamic acid-n-butyl ester, N-(3-fluorobenzoyl)-N-[4-chloro-2-fluoro-5-(n-butoxycarbonylmethylthio)phenyl]-3,4,5,6-tetrahydrophthalamic acid-n-pentyl ester, N-(3-fluorobenzoyl)-N-[4-chloro-2-fluoro-5-(n-butoxycarbonylmethylthio)phenyl]-3,4,5,6-tetrehydrophthalamic acid allyl ester, N-(3-fluorobenzoyl)-N-[4-chloro-2-fluoro-5-(n-butoxycarbonylmethylthio)phenyl]-3,4,5,6-tetrehydrophthalamic acid propargyl ester, N-(3-fluorobenzoyl)-N-[4-chloro-2-fluoro-5-(n-butoxycarbonylmethylthio)phenyl]-3,4,5,6-tetrahydrophthalamic acid methoxymethyl ester, N-(3-fluorobenzoyl)-N-[4-chloro-2-fluoro-5-(n-butoxycarbonylmethylthio)phenyl]-3,4,5,6-tetrahydrophthalamic acid ethoxymethyl ester, N-(3-fluorobenzoyl)-N-[4-chloro-2-fluoro-5-(n-butoxycarbonylmethylthio)phenyl]-3,4,5,6-tetrahydrophthalamic acid-2-methoxyethyl ester, N-(3-fluorobenzoyl)-N-[4-chloro-2-fluoro-5-(n-butoxycarbonylmethylthio)phenyl]-3,4,5,6-tetrahydrophthalamic acid-2-ethoxyethyl ester, N-acetyl-N-[4-chloro-2-fluoro-5-(1-methoxycarbonylethylthio)phenyl]-3,4,5,6-tetrahydrophthalamic acid methyl ester, N-acetyl-N-[4-chloro-2-fluoro-5-(1-methoxycarbonylethylthio)phenyl]-3,4,5,6-tetrehydrophthalamic acid ethyl ester, N-acetyl-N-[4-chloro-2-fluoro-5-(1-methoxycarbonylethylthio)phenyl]-3,4,5,6-tetrahydrophthalamic acid-n-propyl ester, N-acetyl-N-[4-chloro-2-fluoro-5-(1-methoxycarbonylethylthio)phenyl]-3,4,5,6-tetrahydrophthalamic acid-iso-propyl ester, N-acetyl-N-[4-chloro-2-fluoro-5-(1-methoxycarbonylethylthio)phenyl]-3,4,5,6-tetrehydrophthalamic acid-n-butyl ester, N-acetyl-N-[4-chloro-2-fluoro-5-(1-methoxycarbonylethylthio)phenyl]-3,4,5,6-tetrehydrophthalamic acid-n-pentyl ester, N-acetyl-N-[4-chloro-2-fluoro-5-(1-methoxycarbonylethylthio)phenyl]-3,4,5,6-tetrehydrophthalamic acid allyl ester, N-acetyl-N-[4-chloro-2-fluoro-5-(1-methoxycarbonylethylthio)phenyl]-3,4,5,6-tetrehydrophthalamic acid propargyl ester, N-acetyl-N-[4-chloro-2-fluoro-5-(1-methoxycarbonylethylthio)phenyl]-3,4,5,6-tetrahydrophthalamic acid methoxymethyl ester, N-acetyl-N-[4-chloro-2-fluoro- 5-(1-methoxycarbonylethylthio)phenyl]-3,4,5,6-tetrehydrophthalamic acid ethoxymethyl ester, N-acetyl-N-[4-chloro-2-fluoro-5-(1-methoxycarbonylethylthio)phenyl]-3,4,5,6-tetrehydrophthalamic acid-2-methoxyethyl ester, N-acetyl-N-[4-chloro-2-fluoro-5-(1-methoxycarbonylethylthio)phenyl]-3,4,5,6-tetrehydrophthalamic acid-2-ethoxyethyl ester, N-propionyl-N-[4-chloro-2-fluoro-5-(1-methoxycarbonylethylthio)phenyl]-3,4,5,6-tetrahydrophthalamic acid methyl ester, N-propionyl-N-[4-chloro-2-fluoro-5-(1-methoxycarbonylethylthio)phenyl]-3, 4,5,6-tetrahydrophthalamic acid ethyl ester, N-propionyl-N-[4-chloro-2-fluoro-5-(1-methoxycarbonylethylthio)phenyl]-3,4,5,6-tetrehydrophthalamic acid-n-propyl ester, N-propionyl-N-[4-chloro-2-fluoro-5-(1-methoxycarbonylethylthio)phenyl]-3,4,5,6-tetrehydrophthalamic acid-iso-propyl ester, N-propionyl-N-[4-chloro-2-fluoro-5-(1-methoxycarbonylethylthio)phenyl]-3,4,5,6-tetrehydrophthalamic acid-n-butyl ester, N-propionyl-N-[4-chloro-2-fluoro-5-(1-methoxycarbonylethylthio)phenyl]-3,4,5,6-tetrahydrophthalamic acid-n-pentyl ester, N-propionyl-N-[4-chloro-2-fluoro-5-(1-methoxycarbonylethylthio)phenyl]-3,4,5,6-tetrehydrophthalamic acid allyl ester, N-propionyl-N-[4-chloro-2-fluoro-5-(1-methoxycarbonylethylthio)phenyl]-3,4,5,6-tetrahydrophthalamic acid propargyl ester, N-propionyl-N-[4-chloro-2-fluoro-5-(1-methoxycarbonylethylthio)phenyl]-3,4,5,6-tetrehydrophthalamic acid methoxymethyl ester, N-propionyl-N-[4-chloro-2-fluoro-5-(1-methoxycarbonylethylthio)phenyl]-3,4,5,6-tetrahydrophthalamic acid ethoxymethyl ester, N-propionyl-N-[4-chloro-2-fluoro-5-(1-methoxycarbonylethylthio)phenyl]-3,4,5,6-tetrahydrophthalamic acid-2-methoxyethyl ester, N-propionyl-N-[4-chloro-2-fluoro-5-(1-methoxycarbonylethylthio)phenyl]-3,4,5,6-tetrahydrophthalamic acid-2-ethoxyethyl ester, N-(2-chloroacetyl)-N-[4-chloro-2-fluoro-5-(1-methoxycarbonylethylthio)phenyl]-3,4,5,6-tetrahydrophthalamic acid methyl ester, N-(2-chloroacetyl)-N-[4-chloro-2-fluoro-5-(1-methoxycarbonylethylthio)phenyl]-3,4,5,6-tetrahydrophthalamic acid ethyl ester, N-(2-chloroacetyl)-N-[4-chloro-2-fluoro-5-(1-methoxycarbonylethylthio)phenyl]-3,4,5,6-tetrahydrophthalamic acid-n-propyl ester, N-(2-chloroacetyl)-N-[4-chloro-2-fluoro-5-(1-methoxycarbonylethylthio)phenyl]-3,4,5,6-tetrahydrophthalamic acid-iso-propyl ester, N-(2-chloroacetyl)-N-[4-chloro-2-fluoro-5-(1-methoxycarbonylethylthio)phenyl]-3,4,5,6-tetrehydrophthalamic acid-n-butyl ester, N-(2-chloroacetyl)-N-[4-chloro-2-fluoro-5-(1-methoxycarbonylethylthio)phenyl]-3,4,5,6-tetrahydrophthalamic acid-n-pentyl ester, N-(2-chloroacetyl)-N-[4-chloro-2-fluoro-5-(1-methoxycarbonylethylthio)phenyl]-3,4,5,6-tetrahydrophthalamic acid allyl ester, N-(2-chloroacetyl)-N-[4-chloro-2-fluoro-5-(1-methoxycarbonylethylthio)phenyl]-3,4,5,6-tetrahydrophthalamic acid propargyl ester, N-(2-chloroacetyl)-N-[4-chloro-2-fluoro-5-(1-methoxycarbonylethylthio)phenyl]-3,4,5,6-tetrahydrophthalamic acid methoxymethyl ester, N-(2-chloroacetyl)-N-[4-chloro-2-fluoro-5-(1-methoxycarbonylethylthio)phenyl]-3,4,5,6-tetrahydrophthalamic acid ethoxymethyl ester, N-(2-chloroacetyl)-N-[4-chloro-2-fluoro-5-(1-methoxycarbonylethylthio)phenyl]-3,4,5,6-tetrahydrophthalamic acid-2-methoxyethyl ester, N-(2-chloroacetyl)-N-[4-chloro-2-fluoro-5-(1-methoxycarbonylethylthio)phenyl]-3,4,5,6-tetrahydrophthalamic acid-2-ethoxyethyl ester, N-benzoyl-N-[4-chloro-2-fluoro-5-(1-methoxycarbonylethylthio)phenyl]-3,4,5,6-tetrehydrophthalamic acid methyl ester, N-benzoyl-N-[4-chloro-2-fluoro-5-(1-methoxycarbonylethylthio)phenyl]-3,4,5,6-tetrahydrophthalamic acid ethyl ester, N-benzoyl-N-[4-chloro-2-fluoro-5-(1-methoxycarbonylethylthio)phenyl]-3,4,5,6-tetrahydrophthalamic acid-n-propyl ester, N-benzoyl-N-[4-chloro-2-fluoro-5-(1-methoxycarbonylethylthio)phenyl]-3,4,5,6-tetrehydrophthalamic acid-iso-propyl ester, N-benzoyl-N-[4-chloro-2-fluoro-5-(1-methoxycarbonylethylthio)phenyl]-3,4,5,6-tetrehydrophthalamic acid-n-butyl ester, N-benzoyl-N-[4-chloro-2-fluoro-5-(1-methoxycarbonylethylthio)phenyl]-3,4,5,6-tetrehydrophthalamic acid-n-pentyl ester, N-benzoyl-N-[4-chloro-2-fluoro-5-(1-methoxycarbonylethylthio)phenyl]-3,4,5,6-tetrehydrophthalamic acid allyl ester, N-benzoyl-N-[4-chloro-2-fluoro-5-(1-methoxycarbonylethylthio)phenyl]-3,4,5,6-tetrehydrophthalamic acid propargyl ester, N-benzoyl-N-[4-chloro-2-fluoro-5-(1-methoxycarbonylethylthio)phenyl]-3,4,5,6-tetrahydrophthalamic acid methoxymethyl ester, N-benzoyl-N-[4-chloro-2-fluoro-5-(1-methoxycarbonylethylthio)phenyl]-3,4,5,6-tetrahydrophthalamic acid ethoxymethyl ester, N-benzoyl-N-[4-chloro-2-fluoro-5-(1-methoxycarbonylethylthio)phenyl]-3,4,5,6-tetrahydrophthalamic acid-2-methoxyethyl ester, N-benzoyl-N-[4-chloro-2-fluoro-5-(1-methoxycarbonylethylthio)phenyl]-3,4,5,6-tetrahydrophthalamic acid-2-ethoxyethyl ester, N-(3-fluorobenzoyl)-N-[4-chloro-2-fluoro-5-(1-methoxycarbonylethylthio)phenyl]-3,4,5,6-tetrahydrophthalamic acid methyl ester, N-(3-fluorobenzoyl)-N-[4-chloro-2-fluoro-5-(1-methoxycarbonylethylthio)phenyl]-3,4,5,6-tetrehydrophthalamic acid ethyl ester, N-(3-fluorobenzoyl)-N-[4-chloro-2-fluoro-5-(1-methoxycarbonylethylthio)phenyl]-3,4,5,6-tetrehydrophthalamic acid-n-propyl ester, N-(3-fluorobenzoyl)N-[4-chloro-2-fluoro-5-(1-methoxycarbonylethylthio)phenyl]-3,4,5,6-tetrahydrophthalamic acid-iso-propyl ester, N-(3-fluorobenzoyl)-N-[4-chloro-2-fluoro-5-(1-methoxycarbonylethylthio)phenyl]-3,4,5,6-tetrahydrophthalamic acid-n-butyl ester, N-(3-fluorobenzoyl)-N-[4-chloro-2-fluoro-5-(1-methoxycarbonylethylthio)phenyl]-3,4,5,6-tetrahydrophthalamic acid-n-pentyl ester, N-(3-fluorobenzoyl)-N-[4-chloro-2-fluoro-5-(1-methoxycarbonylethylthio)phenyl]-3,4,5,6-tetrahydrophthalamic acid allyl ester, N-(3-fluorobenzoyl)-N-[4-chloro-2-fluoro-5-(1-methoxycarbonylethylthio)phenyl]-3,4,5,6-tetrahydrophthalamic acid propargyl ester, N-(3-fluorobenzoyl)-N-[4-chloro-2-fluoro-5-(1-methoxycarbonylethylthio)phenyl]-3,4,5,6-tetrahydrophthalamic acid methoxymethyl ester, N-(3-fluorobenzoyl)-N-[4-chloro-2-fluoro-5-(1-methoxycarbonylethylthio)phenyl]-3,4,5,6-tetrehydrophthalamic acid ethoxymethyl ester, N-(3-fluorobenzoyl)-N-[4-chloro-2-fluoro-5-(1-methoxycarbonylethylthio)phenyl]-3,4,5,6-tetrahydrophthalamic acid-2-methoxyethyl ester, N-(3-fluorobenzoyl)-N-[4-chloro-2-fluoro-5-(1-methoxycarbonylethylthio)phenyl]-3,4,5,6-tetrahydrophthalamic acid-2-ethoxyethyl ester, and the like.

Furthermore, as concrete examples of N-phenyltetrahydrophthalamic acid derivatives [II] which are compounds of the present invention, there can be cited, for example, N-[4-chloro-2-fluoro-5-(iso-propoxy)phenyl]-N-nicotinyl-3,4,5,6-tetrahydrophthalamic acid methyl ester, N-[4-chloro-2-fluoro-5-(iso-propoxy)phenyl]-N-nicotinyl-3,4,5,6-tetrahydrophthalamic acid allyl ester, N-[4-chloro-2-fluoro-5-(iso-propoxy)phenyl]-N-nicotinyl-3,4,5,6-tetrahydrophthalamic acid propargyl ester, N-[4-chloro-2-fluoro-5-(iso-propoxy)phenyl]-N-nicotinyl-3,4,5,6-tetrahydrophthalamic acid cyclopentyl ester, N-[4-chloro-2-fluoro-5-(iso-propoxy)phenyl]-N-nicotinyl-3,4,5,6- tetrahydrophthalamic acid-2-methoxyethyl ester, N-[4-chloro-2-fluoro-5-(iso-propoxy)phenyl]-N-(6-chloronicotinyl)-3,4,5,6-tetrahydrophthalamic acid methyl ester, N-[4-chloro-2-fluoro-5-(iso-propoxy)phenyl]-N-(6-chloronicotinyl)-3,4,5,6-tetrahydrophthalamic acid allyl ester, N-[4-chloro-2-fluoro-5-(iso-propoxy)phenyl]-N-(6-chloronicotinyl)-3,4,5,6-tetrahydrophthalamic acid propargyl ester, N-[4-chloro-2-fluoro-5-(iso-propoxy)phenyl]-N-(6-chloronicotinyl)-3,4,5,6-tetrahydrophthalamic acid cyclopentyl ester, N-[4-chloro-2-fluoro-5-(iso-propoxy)phenyl]-N-(6-chloronicotinyl)-3,4,5,6-tetrahydrophthalamic acid-2-methoxyethyl ester, N-[4-chloro-2-fluoro-5-(iso-propoxy)phenyl]-N-(4-methylnicotinyl)-3,4,5,6-tetrehydrophthalamic acid methyl ester, N-[4-chloro-2-fluoro-5-(iso-propoxy)phenyl]-N-(4-methylnicotinyl)-3,4,5,6-tetrehydrophthalamic acid allyl ester, N-[4-chloro-2-fluoro-5-(iso-propoxy)phenyl]-N-(4-methylnicotinyl)-3,4,5,6-tetrehydrophthalamic acid propargyl ester, N-[4-chloro-2-fluoro5-(iso-propoxy)phenyl]-N-(4-methylnicotinyl)-3,4,5,6-tetrehydrophthalamic acid cyclopentyl ester, N-[4-chloro-2-fluoro-5-(iso-propoxy)phenyl]-N-(4-methylnicotinyl)-3,4,5,6-tetrehydrophthalamic acid-2-methoxyethyl ester, N-[4-chloro-2-fluoro- 5-(iso-propoxy)phenyl]-N-(5-methoxycarbonylnicotinyl)-3,4,5,6-tetrahydrophthalamic acid methyl ester, N-[4-chloro-2-fluoro-5-(iso-propoxy)phenyl]-N-(5-methoxycarbonylnicotinyl)-3,4,5,6-tetrahydrophthalamic acid allyl ester, N-[4-chloro-2-fluoro-5-(iso-propoxy)phenyl]-N-(5-methoxycarbonylnicotinyl)-3,4,5,6-tetrahydrophthalamic acid propargyl ester, N-[4-chloro-2-fluoro-5-(iso-propoxy)phenyl]-N-(5-methoxycarbonylnicotinyl)-3,4,5,6-tetrahydrophthalamic acid cyclopentyl ester, N-[4-chloro-2-fluoro-5-(iso-propoxy)phenyl]-N-(5-methoxycarbonylnicotinyl)-3,4,5,6-tetrahydrophthalamic acid-2-methoxyethyl ester, N-(4-chloro-2-fluoro-5-allyloxyphenyl)-N-nicotinyl 3,4,5,6-tetrahydrophthalamic acid methyl ester, N-(4-chloro-2-fluoro-5-allyloxyphenyl)-N-nicotinyl-3,4,5,6-tetrahydrophthalamic acid allyl ester, N-(4-chloro-2-fluoro-5-allyloxyphenyl)-N-nicotinyl-3,4,5,6-tetrahydrophthalamic acid propargyl ester, N-(4-chloro-2-fluoro-5-allyloxyphenyl)-N-nicotinyl-3,4,5,6-tetrahydrophthalamic acid cyclopentyl ester, N-(4-chloro-2-fluoro-5-allyloxyphenyl)-N-nicotinyl-3,4,5,6-tetrahydrophthalamic acid-2-methoxyethyl ester, N-(4-chloro-2-fluoro-5-allyloxyphenyl)-N-(6-chloronicotinyl)-3,4,5,6-tetrahydrophthalamic acid methyl ester, N-(4-chloro-2-fluoro-5-allyloxyphenyl)-N-(6-chloronicotinyl)-3,4,5,6-tetrahydrophthalamic acid allyl ester, N-(4-chloro-2-fluoro-5-allyloxyphenyl)-N-(6-chloronicotinyl)-3,4,5,6-tetrahydrophthalamic acid propargyl ester, N-(4-chloro-2-fluoro-5-allyloxyphenyl)-N-(6-chloronicotinyl)-3,4,5,6-tetrahydrophthalamic acid cyclopentyl ester, N-(4-chloro-2-fluoro-5-allyloxyphenyl)-N-(6-chloronicotinyl)-3,4,5,6-tetrahydrophthalamic acid-2-methoxyethyl ester, N-(4-chloro-2-fluoro-5-allyloxyphenyl)-N-(4-methylnicotinyl)-3,4,5,6-tetrahydrophthalamic acid methyl ester, N-(4-chloro-2-fluoro-5-allyloxyphenyl)-N-(4-methylnicotinyl)-3,4,5,6-tetrahydrophthalamic acid allyl ester, N-(4-chloro-2-fluoro-5-allyloxyphenyl)-N-(4-methylnicotinyl)-3,4,5,6-tetrahydrophthalamic acid propargyl ester, N-(4-chloro-2-fluoro- 5-allyloxyphenyl)-N-(4-methylnicotinyl)-3,4,5,6-tetrahydrophthalamic acid cyclopentyl ester, N-(4-chloro-2-fluoro-5-allyloxyphenyl)-N-(4-methylnicotinyl)-3,4,5,6-tetrahydrophthalamic acid-2-methoxyethyl ester, N-(4-chloro-2-fluoro-5-allyloxyphenyl)-N-(5-methoxycarbonylnicotinyl)-3,4,5,6-tetrahydrophthalamic acid methyl ester, N-(4-chloro-2-fluoro-5-allyloxyphenyl)-N-(5-methoxycarbonylnicotinyl)-3,4,5,6-tetrehydrophthalamic acid propargyl ester, N-(4-chloro-2-fluoro5-allyloxyphenyl)-N-(5-methoxycarbonylnicotinyl)-3,4,5,6-tetrehydrophthalamic acid cyclopentyl ester, N-(4-chloro-2-fluoro-5-allyloxyphenyl)-N-(5-methoxycarbonylnicotinyl)-3,4,5,6-tetrahydrophthalamic acid-2-methoxyethyl ester, N-[4-chloro-2-fluoro-5-(1-methylpropargyloxy)pheny]-N-nicotinyl-3,4,5,6-tetrahydrophthalamic acid methyl ester, N-[4-chloro-2-fluoro-5-(1-methylpropargyloxy)phenyl]-N-nicotinyl-3,4,5,6-tetrahydrophthalamic acid allyl ester, N-[4-chloro-2-fluoro-5-(1-methylpropargyloxy)phenyl]-N-nicotinyl-3,4,5,6-tetrahydrophthalamic acid propargyl ester, N-[4-chloro-2-fluoro-5-(1-methylpropargyloxy)phenyl]-N-nicotinyl-3,4,5,6-tetrahydrophthalamic acid cyclopentyl ester, N-[4-chloro-2-fluoro-5-(1-methylpropargyloxy)phenyl]-N-nicotinyl-3,4,5,6-tetrahydrophthalamic acid-2-methoxyethyl ester, N-[4-chloro-2-fluoro-5-(1-methylpropargyloxy)phenyl]-N-(6-chloronicotinyl)-3,4,5,6-tetrehydrophthalamic acid methyl ester, N-[4-chloro-2-fluoro-5-(1-methylpropargyloxy)phenyl]-N-(6-chloronicotinyl)-3,4,5,6-tetrehydrophthalamic acid allyl ester, N-[4-chloro-2-fluoro-5-(1-methylpropargyloxy)phenyl]-N-(6-chloronicotin tetrahydrophthalamic acid propargyl ester, N-[4-chloro-2-fluoro5-(1-methylpropargyloxy)phenyl]-N-(6-chloronic tetrahydrophthalamic acid cyclopentyl ester, N-[4-chloro-2-fluoro-5-(1-methylpropargyloxy)phenyl]-N-(6-chloronicotinyl)-3,4,5,6-tetrahydrophthalamic acid-2-methoxyethyl ester, N-[4-chloro-2-fluoro-5-(1-methylpropargyloxy)phenyl]-N-(4-methylnicotinyl)-3,4,5,6-tetrahydrophthalamic acid methyl ester, N-[4-chloro-2-fluoro-5-(1-methylpropargyloxy)phenyl]-N-(4-methylnicotinyl)-3,4,5,6-tetrahydrophthalamic acid allyl ester, N-[4-chloro-2-fluoro-5-(1-methylpropargyloxy)phenyl]-N-(4-methylnicotinyl)-3,4,5,6-tetrahydrophthalamic acid propargyl ester, N-[4-chloro-2-fluoro-5-(1-methylpropargyloxy)phenyl]-N-(4-methylnicotinyl)-3,4,5,6-tetrahydrophthalamic acid cyclopentyl ester, N-[4-chloro-2-fluoro-5-(1-methylpropargyloxy)phenyl]-N-(4-methylnicotinyl)-3,4,5,6-tetrahydrophthalamic acid-2-methoxyethyl ester, N-[4-chloro-2-fluoro-5-(1-methylpropargyloxy)phenyl]-N-(5-methoxycarbonylnicotinyl)-3,4,5,6-tetrahydrophthalamic acid methyl ester, N-[4-chloro-2-fluoro-5-(1-methylpropargyloxy)phenyl]-N-(5-nicotinyl)-3,4,5,6-tetrahydrophthalamic acid allyl ester, N-[4-chloro-2-fluoro-5-(1-methylpropargyloxy)phenyl]-N-(5-methoxycarbonylnicotinyl)-3,4,5,6-tetrahydrophthalamic acid propargyl ester, N-[4-chloro-2-fluoro-5-(1-methylpropargyloxy)phenyl]-N-(5-methoxycarbonylnicotinyl)-3,4,5,6-tetrahydrophthalamic acid cyclopentyl ester, N-[4-chloro-2-fluoro-5-(1-methylpropargyloxy)phenyl]-N-(5-methoxycarbonylnicotinyl)-3,4,5,6-tetrahydrophthalamic acid-2-methoxyethyl ester, N-(4-chloro-2-fluoro-5-methoxycarbonylphenyl)-N-nicotinyl-3,4,5,6-tetrahydrophthalamic acid methyl ester, N-(4-chloro-2-fluoro-5-methoxycarbonylphenyl)-N-nicotinyl-3,4,5,6-tetrehydrophthalamic acid allyl ester, N-(4-chloro-2-fluoro-5-methoxycarbonylphenyl)-N-nicotinyl-3,4,5,6-tetrahydrophthalamic acid propargyl ester, N-(4-chloro-2-fluoro-5-methoxycarbonylphenyl)-N-nicotinyl-3,4,5,6-tetrahydrophthalamic acid cyclopentyl ester, N-(4-chloro-2-fluoro-5-methoxycarbonylphenyl)-N-nicotinyl-3,4,5,6-tetrahydrophthalamic acid-2-methoxyethyl ester, N-(4-chloro-2-fluoro-5-methoxycarbonylphenyl)-N-(6- chloronicotinyl)-3,4,5,6-tetrehydrophthalamic acid methyl ester, N-(4-chloro-2-fluoro-5-methoxycarbonylphenyl)-N-(6-chloronicotinyl)-3,4,5,6-tetrehydrophthalamic acid allyl ester, N-(4-chloro-2-fluoro-5-methoxycarbonylphenyl)-N-(6-chloronicotinyl)-3,4,5,6-tetrehydrophthalamic acid propargyl ester, N-(4-chloro-2-fluoro5-methoxycarbonylphenyl)-N-(6-chloronicotinyl)-3,4,5,6-tetrehydrophthalamic acid cyclopentyl ester, N-(4-chloro-2-fluoro-5-methoxycarbonylphenyl)-N-(6-chloronicotinyl)-3,4,5,6-tetrehydrophthalamic acid-2-methoxyethyl ester, N-(4-chloro-2-fluoro-5-methoxycarbonylphenyl)-N-(4-methylnicotinyl)-3,4,5,6-tetrehydrophthalamic acid methyl ester, N-(4-chloro-2-fluoro-5-methoxycarbonylphenyl)-N-(4-methylnicotinyl)-3,4,5,6-tetrehydrophthalamic acid allyl ester, N-(4-chloro-2-fluoro-5-methoxycarbonylphenyl)-N-(4-methylnicotinyl)-3,4,5,6-tetrehydrophthalamic acid propargyl ester, N-(4-chloro-2-fluoro5-methoxycarbonylphenyl)-N-(4-methylnicotinyl)-3,4,5,6-tetrahydrophthalamic acid cyclopentyl ester, N-(4-chloro-2-fluoro-5-methoxycarbonylphenyl)-N-(4-methylnicotinyl)-3,4,5,6-tetrehydrophthalamic acid-2-methoxyethyl ester, N-(4-chloro-2-fluoro-5-methoxycarbonylphenyl)-N-(5-methoxycarbonylnicotinyl)-3,4,5,6-tetrahydrophthalamic acid methyl ester, N-(4-chloro-2-fluoro-5-methoxycarbonylphenyl)-N-(5-methoxycarbonylnicotinyl)-3,4,5,6-tetrahydrophthalamic acid allyl ester, N-(4-chloro-2-fluoro-5-methoxycarbonylphenyl)-N-(5-methoxycarbonylnicotinyl)-3,4,5,6-tetrahydrophthalamic acid propargyl ester, N-(4-chloro-2-fluoro-5-methoxycarbonylphenyl)-N-(5-methoxycarbonylnicotinyl)-3,4,5,6-tetrahydrophthalamic acid cyclopentyl ester, N-(4-chloro-2-fluoro-5-methoxycarbonylphenyl)-N-(5-methoxycarbonylnicotinyl)-3,4,5,6-tetrahydrophthalamic acid-2-methoxyethyl ester, N-(4-chloro-2-fluoro-5-methoxycarbonylmethoxyphenyl)-N-nicotinyl 3,4,5,6-tetrahydrophthalamic acid methyl ester, N-(4-chloro-2-fluoro-5-methoxycarbonylmethoxyphenyl)-N-nicotinyl-3,4,5,6-tetrahydrophthalamic acid allyl ester, N-(4-chloro-2-fluoro-5-methoxycarbonylmethoxyphenyl)-N-nicotinyl-3,4,5,6-tetrahydrophthalamic acid propargyl ester, N-(4-chloro-2-fluoro5-methoxycarbonylmethoxyphenyl)-N-nicotinyl-3,4,5,6-tetrahydrophthalamic acid cyclopentyl ester, N-(4-chloro-2-fluoro-5-methoxycarbonylmethoxyphenyl)-N-nicotinyl-3,4,5,6-tetrehydrophthalamic acid-2-methoxyethyl ester, N-(4-chloro-2-fluoro-5-methoxycarbonylmethoxyphenyl)-N-(6-chloronicotinyl)-3,4,5,6-tetrahydrophthalamic acid methyl ester, N-(4-chloro-2-fluoro-5-methoxycarbonylmethoxyphenyl)-N-(6-chloronicotinyl)-3,4,5,6-tetrahydrophthalamic acid allyl ester, N-(4-chloro-2-fluoro-5-methoxycarbonylmethoxyphenyl)-N-(6-chloronicotinyl)-3,4,5,6-tetrahydrophthalamic acid propargyl ester, N-(4-chloro-2-fluoro-5-methoxycarbonylmethoxyphenyl)-N-(6-chloronicotinyl)-3,4,5,6-tetrahydrophthalamic acid cyclopentyl ester, N-(4-chloro-2-fluoro-5-methoxycarbonylmethoxyphenyl)-N-(6-chloronicotinyl)-3,4,5,6-tetrahydrophthalamic acid-2-methoxyethyl ester, N-(4-chloro-2-fluoro-5-methoxycarbonylmethoxyphenyl)-N-(4-methylnicotinyl)-3,4,5,6-tetrahydrophthalamic acid methyl ester, N-(4-chloro-2-fluoro-5-methoxycarbonylmethoxyphenyl)-N-(4-methylnicotinyl)-3,4,5,6-tetrahydrophthalamic acid allyl ester, N-(4-chloro-2-fluoro-5-methoxycarbonylmethoxyphenyl)-N-(4-methylnicotinyl)-3,4,5,6-tetrehydrophthalamic acid propargyl ester, N-(4-chloro-2-fluoro5-methoxycarbonylmethoxyphenyl)-N-(4-methylnicotinyl)-3,4,5,6-tetrahydrophthalamic acid cyclopentyl ester, N-(4-chloro-2-fluoro-5-methoxycarbonylmethoxyphenyl)-N-(4-methylnicotinyl)-3,4,5,6-tetrahydrophthalamic acid-2-methoxyethyl ester, N-(4-chloro-2-fluoro-5-methoxycarbonylmethoxyphenyl)-N-(5-methoxycarbonylnicotinyl)-3,4,5,6-tetrehydrophthalamic acid methyl ester, N-(4-chloro-2-fluoro-5-methoxycarbonylmethoxyphenyl)-N-(5-methoxycarbonylnicotinyl)-3,4,5,6-tetrahydrophthalamic acid allyl ester, N-(4-chloro-2-fluoro-5-methoxycarbonylmethoxyphenyl)-N-(5-methoxycarbonylnicotinyl)-3,4,5,6-tetrahydrophthalamic acid propargyl ester, N-(4-chloro-2-fluoro-5-methoxycarbonylmethoxyphenyl)-N-(5-methoxycarbonylnicotinyl)-3,4,5,6-tetrahydrophthalamic acid cyclopentyl ester, N-(4-chloro-2-fluoro-5-methoxycarbonylmethoxyphenyl)-N-(5-methoxycarbonylnicotinyl)-3,4,5,6-tetrahydrophthalamic acid-2-methoxyethyl ester, N-(4-chloro-2-fluoro-5-methoxycarbonylmethylthiophenyl)-N-nicotinyl-3,4,5,6-tetrahydrophthalamic acid methyl ester, N-(4-chloro-2-fluoro-5-methoxycarbonylmethylthiophenyl)-N-nicotinyl-3,4,5,6-tetrahydrophthalamic acid allyl ester, N-(4-chloro-2-fluoro-5-methoxycarbonylmethylthiophenyl)-N-nicotinyl-3,4,5,6-tetrahydrophthalamic acid propargyl ester, N-(4-chloro-2-fluoro-5-methoxycarbonylmethylthiophenyl)-N-nicotinyl-3,4,5,6-tetrahydrophthalamic acid cyclopentyl ester, N-(4-chloro-2-fluoro-5-methoxycarbonylmethylthiophenyl)-N-nicotinyl-3,4,5,6-tetrahydrophthalamic acid-2-methoxyethyl ester, N-(4-chloro-2-fluoro-5-methoxycarbonylmethylthiophenyl)-N-(6-chloronicotinyl)-3,4,5,6-tetrahydrophthalamic acid methyl ester, N-(4-chloro-2-fluoro-5-methoxycarbonylmethylthiophenyl)-N-(6-chloronicotinyl)-3,4,5,6-tetrahydrophthalamic acid allyl ester, N-(4-chloro-2-fluoro-5-methoxycarbonylmethylthiophenyl)-N-(6-chloronicotinyl)-3,4,5,6-tetrahydrophthalamic acid propargyl ester, N-(4-chloro-2-fluoro-5-methoxycarbonylmethylthiophenyl)-N-($^6$-chloronicotinyl)-3,4,5,6-tetrahydrophthalamic acid cyclopentyl ester, N-(4-chloro-2-fluoro-5-methoxycarbonylmethylthiophenyl)-N-(6-chloronicotinyl)-3,4,5,6-tetrahydrophthalamic acid-2-methoxyethyl ester, N-(4-chloro-2-fluoro-5-methoxycarbonylmethylthiophenyl)-N-(4-methylnicotinyl)-3,4,5,6-tetrahydrophthalamic acid methyl ester, N-(4-chloro-2-fluoro-5-methoxycarbonylmethylthiophenyl)-N-(4-methylnicotinyl)-3,4,5,6-tetrahydrophthalamic acid allyl ester, N-(4-chloro-2-fluoro-5-methoxycarbonylmethylthiophenyl)-N-(4-methylnicotinyl)-3,4,5,6-tetrahydrophthalamic acid propargyl ester, N-(4-chloro-2-fluoro-5-methoxycarbonylmethylthiophenyl)-N-(4-methylnicotinyl)-3,4,5,6-tetrahydrophthalamic acid cyclopentyl ester, N-(4-chloro-2-fluoro-5-methoxycarbonylmethylthiophenyl)-N-(4-methylnicotinyl)-3,4,5,6-tetrahydrophthalamic acid-2-methoxyethyl ester, N-(4-chloro-2-fluoro-5-methoxycarbonylmethylthiophenyl)-N-(5-methoxycarbonylnicotinyl)-3,4,5,6-tetrahydrophthalamic acid methyl ester, N-( 4-chloro-2-fluoro-5-methoxycarbonylmethylthiophenyl)-N-(5-methoxycarbonylnicotinyl)-3,4,5,6-tetrahydrophthalamic acid allyl ester, N-(4-chloro-2-fluoro-5-methoxycarbonylmethylthiophenyl)-N-(5-methoxycarbonylnicotinyl)-3,4,5,6-tetrahydrophthalamic acid propargyl ester, N-(4-chloro-2-fluoro-5-methoxycarbonylmethylthiophenyl)-N-(5-methoxycarbonylnicotinyl)-3,4,5,6-tetrahydrophthalamic acid cyclopentyl ester, N-(4-chloro-2-fluoro-5- methoxycarbonylmethylthiophenyl)-N-(5-methoxycarbonylnicotinyl)-3,4,5,6-tetrahydrophthalamic acid-2-methoxyethyl ester, N-[2,4-dichloro-5-(iso-propoxy) phenyl]-N-nicotinyl-3,4,5,6-tetrahydrophthalamic acid methyl ester, N-[2,4-dichloro-5-(iso-propoxy)phenyl]-N-nicotinyl-3,4,5,6-tetrahydrophthalamic acid allyl ester, N-[2,4-dichloro-5-(iso-propoxy)phenyl]-N-nicotinyl-3,4,5,6-tetrahydrophthalamic acid propargyl ester, N-[2,4-dichloro-5-(iso-propoxy)phenyl]-N-nicotinyl-3,4,5,6-tetrahydrophthalamic acid cyclopentyl ester, N-[2,4-dichloro-5-(iso-propoxy)phenyl]-N-nicotinyl-3,4,5,6-tetrehydrophthalamic acid-2-methoxyethyl ester, N-[2,4-dichloro-5-(iso-propoxy)phenyl]-N-(6-chloronicotinyl)-3,4,5,6-tetrahydrophthalamic acid methyl ester, N-[2,4-dichloro-5-(iso-propoxy)phenyl]-N-(6-chloronicotinyl)-3,4,5,6-tetrahydrophthalamic acid allyl ester, N-[2,4-dichloro-5-(iso-propoxy)phenyl]-N-(6-chloronicotinyl)-3,4,5,6-tetrehydrophthalamic acid propargyl ester, N-[2,4-dichloro-5-(iso-propoxy)phenyl]-N-(6-chloronicotinyl)-3,4,5,6-tetrehydrophthalamic acid cyclopentyl ester, N-[2,4-dichloro-5-(iso-propoxy)phenyl]-N-(6-chloronicotinyl)-3,4,5,6-tetrehydrophthalamic acid-2-methoxyethyl ester, N-[2,4-dichloro-5-(iso-propoxy)phenyl]-N-(4-methylnicotinyl)-3,4,5,6-tetrehydrophthalamic acid methyl ester, N-[2,4-dichloro-5-(iso-propoxy)phenyl]-N-(4-methylnicotinyl)-3,4,5,6-tetrahydrophthalamic acid allyl ester, N-[2,4-dichloro-5-(iso-propoxy)phenyl]-N-(4-methylnicotinyl)-3,4,5,6-tetrahydrophthalamic acid propargyl ester, N-[2,4-dichloro-5-(iso-propoxy)phenyl]-N-(4-methylnicotinyl)-3,4,5,6-tetrehydrophthalamic acid cyclopentyl ester, N-[2,4-dichloro-5-(iso-propoxy)phenyl]-N-(4-methylnicotinyl)-3,4,5,6-tetrehydrophthalamic acid-2-methoxyethyl ester, N-[2,4-dichloro-5-(iso-propoxy)phenyl]-N-(5-methoxycarbonylnicotinyl)-3,4,5,6-tetrahydrophthalamic acid methyl ester, N-[2,4-dichloro-5-(iso-propoxy)phenyl]-N-(5-methoxycarbonylnicotinyl)-3,4,5,6-tetrahydrophthalamic acid allyl ester, N-[2,4-dichloro-5-(iso-propoxy)phenyl]-N-(5-methoxycarbonylnicotinyl)-3,4,5,6-tetrahydrophthalamic acid propargyl ester, N-[2,4-dichloro-5-(iso-propoxy)phenyl]-N-(5-methoxycarbonylnicotinyl)-3,4,5,6-tetrahydrophthalamic acid cyclopentyl ester, N-[2,4-dichloro-5-(iso-propoxy)phenyl]-N-(5-methoxycarbonylnicotinyl)-3,4,5,6-tetrahydrophthalamic acid-2-methoxyethyl ester, N-(2,4-dichloro-5-allyloxyphenyl)-N-nicotinyl-3,4,5,6-tetrahydrophthalamic acid methyl ester, N-(2,4-dichloro-5-allyloxyphenyl)-N-nicotinyl-3,4,5,6-tetrahydrophthalamic acid allyl ester, N-(2,4-dichloro-5-allyloxyphenyl)-N-nicotinyl-3,4,5,6-tetrahydrophthalamic acid propargyl ester, N-(2,4-dichloro-5-allyloxyphenyl)-N-nicotinyl-3,4,5,6-tetrahydrophthalamic acid cyclopentyl ester, N-(2,4-dichloro-5-allyloxyphenyl)-N-nicotinyl-3,4,5,6-tetrahydrophthalamic acid-2-methoxyethyl ester, N-(2,4-dichloro-5-allyloxyphenyl)-N-(6-chloronicotinyl)-3,4,5,6-tetrahydrophthalamic acid methyl ester, N-(2,4-dichloro-5-allyloxyphenyl)-N-(6-chloronicotinyl)-3,4,5,6-tetrahydrophthalamic acid allyl ester, N-(2,4-dichloro-5-allyloxyphenyl)-N-(6-chloronicotinyl)-3,4,5,6-tetrahydrophthalamic acid propargyl ester, N-(2,4-dichloro-5-allyloxyphenyl)-N-(6-chloronicotinyl)-3,4,5,6-tetrahydrophthalamic acid cyclopentyl ester, N-(2,4-dichloro-5-allyloxyphenyl)-N-(6-chloronicotinyl)-3,4,5,6-tetrahydrophthalamic acid-2-methoxyethyl ester, N-(2,4-dichloro-5-allyloxyphenyl)-N-(4-methylnicotinyl)-3,4,5,6-tetrahydrophthalamic acid methyl ester, N-(2,4-dichloro-5-allyloxyphenyl)-N-(4-methylnicotinyl)-3,4,5,6-tetrahydrophthalamic acid allyl ester, N-(2,4-dichloro-5-allyloxyphenyl)-N-(4-methylnicotinyl)-3,4,5,6-tetrahydrophthalamic acid propargyl ester, N-(2,4-dichloro-5-allyloxyphenyl)-N-(4-methylnicotinyl)-3,4,5,6-tetrahydrophthalamic acid cyclopentyl ester, N-(2,4-dichloro-5-allyloxyphenyl)-N-(4-methylnicotinyl)-3,4,5,6-tetrehydrophthalamic acid-2-methoxyethyl ester, N-(2,4-dichloro-5-allyloxyphenyl)-N-(5-methoxycarbonylnicotinyl)-3,4,5,6-tetrahydrophthalamic acid methyl ester, N-(2,4-dichloro-5-allyloxyphenyl)-N-(5-methoxycarbonylnicotinyl)-3,4,5,6-tetrehydrophthalamic acid allyl ester, N-(2,4-dichloro-5-allyloxyphenyl)-N-(5-methoxycarbonylnicotinyl)-3,4,5,6-tetrehydrophthalamic acid propargyl ester, N-(2,4-dichloro-5-allyloxyphenyl)-N-(5-methoxycarbonylnicotinyl)-3,4,5,6-tetrehydrophthalamic acid cyclopentyl ester, N-(2,4-dichloro-5-allyloxyphenyl)-N-(5-methoxycarbonylnicotinyl)-3,4,5,6-tetrehydrophthalamic acid-2-methoxyethyl ester, N-[2,4-dichloro-5-(1-methylpropargyloxy)phenyl]-N-nicotinyl-3,4,5,6-tetrahydrophthalamic acid methyl ester, N-[2,4-dichloro-5-(1-methylpropargyloxy)phenyl]-N-nicotinyl-3,4,5,6-tetrahydrophthalamic acid allyl ester, N-[2,4-dichloro-5-(1-methylpropargyloxy)phenyl]-N-nicotinyl-3,4,5,6-tetrahydrophthalamic acid propargyl ester, N-[2,4-dichloro-5-(1-methylpropargyloxy)phenyl]-N-nicotinyl-3,4,5,6-tetrahydrophthalamic acid cyclopentyl ester, N-[2,4-dichloro-5-(1-methylpropargyloxy)phenyl]-N-nicotinyl-3,4,5,6-tetrahydrophthalamic acid-2-methoxyethyl ester, N-[2,4-dichloro-5-(1-methylpropargyloxy)phenyl]-N-(6-chloronicotinyl)-3,4,5,6-tetrahydrophthalamic acid methyl ester, N-[2,4-dichloro-5-(1-methylpropargyloxy)phenyl]-N-(6-chloronicotinyl)-3,4,5,6-tetrahydrophthalamic acid allyl ester, N-[2,4-dichloro-5-(1-methylpropargyloxy)phenyl]-N-(6-chloronicotinyl)-3,4,5,6-tetrahydrophthalamic acid propargyl ester, N-[2,4-dichloro-5-(1-methylpropargyloxy)phenyl]-N-(6-chloronicotinyl)-3,4,5,6-tetrahydrophthalamic acid cyclopentyl ester, N-[2,4-dichloro-5-(1-methylpropargyloxy)phenyl]-N-(6-chloronicotinyl)-3,4,5,6-tetrahydrophthalamic acid-2-methoxyethyl ester, N-[2,4-dichloro-5-(1-methylpropargyloxy)phenyl]-N-(4-methylnicotinyl)-3,4,5,6-tetrahydrophthalamic acid methyl ester, N-[2,4-dichloro-5-(1-methylpropargyloxy)phenyl]-N-(4-methylnicotinyl)-3,4,5,6-tetrahydrophthalamic acid allyl ester, N-[2,4-dichloro-5-(1-methylpropargyloxy)phenyl]-N-(4-methylnicotinyl)-3,4,5,6-tetrahydrophthalamic acid propargyl ester, N-[2,4-dichloro-5-(1-methylpropargyloxy)phenyl]-N-(4-methylnicotinyl)-3,4,5,6-tetrahydrophthalamic acid cyclopentyl ester, N-[2,4-dichloro-5-(1-methylpropargyloxy)phenyl]-N-(4-methylnicotinyl)-3,4,5,6-tetrahydrophthalamic acid-2-methoxyethyl ester, N-[2,4-dichloro-5-(1-methylpropargyloxy)phenyl]-N-(5-methoxycarbonylnicotinyl)-3,4,5,6-tetrahydrophthalamic acid methyl ester, N-[2,4-dichloro-5-(1-methylpropargyloxy)phenyl]-N-(5-methoxycarbonylnicotinyl)-3,4,5,6-tetrahydrophthalamic acid allyl ester, N-[2,4-dichloro-5-(1-methylpropargyloxy)phenyl]-N-(5-methoxycarbonylnicotinyl)-3,4,5,6-tetrahydrophthalamic acid propargyl ester, N-[2,4-dichloro-5-(1-methylpropargyloxy)phenyl]-N-(5-methoxycarbonylnicotinyl)-3,4,5,6-tetrahydrophthalamic acid cyclopentyl ester, N-[2,4-dichloro-5-(1-methylpropargyloxy)phenyl]-N-(5-methoxycarbonylnicotinyl)-3,4,5,6-tetrahydrophthalamic acid-2-methoxyethyl ester, N-(2,4-dichloro-5-methoxycarbonylphenyl)-N-nicotinyl-3,4,5,6-tetrahydrophthalamic acid methyl ester, N-(2,4-dichloro-5- methoxycarbonylphenyl)-N-nicotinyl-3,4,5,6-tetrahydrophthalamic acid allyl ester, N-(2,4-dichloro-5-methoxycarbonylphenyl)-N-nicotinyl-3,4,5,6-tetrahydrophthalamic acid propargyl ester, N-(2,4-dichloro-5-methoxycarbonylphenyl)-N-nicotinyl 3,4,5,6-tetrahydrophthalamic acid cyclopentyl ester, N-(2,4-dichloro-5-methoxycarbonylphenyl)-N-nicotinyl-3,4,5,6-tetrahydrophthalamic acid-2-methoxyethyl ester, N-(2,4-dichloro-5-methoxycarbonylphenyl)-N-(6-chloronicotinyl)-3,4,5,6-tetrahydrophthalamic acid methyl ester, N-(2,4-dichloro-5-methoxycarbonylphenyl)-N-(6-chloronicotinyl)-3,4,5,6-tetrahydrophthalamic acid allyl ester, N-(2,4-dichloro-5-methoxycarbonylphenyl)-N-(6-chloronicotinyl)-3,4,5,6-tetrahydrophthalamic acid propargyl ester, N-(2,4-dichloro-5-methoxycarbonylphenyl)-N-(6-chloronicotinyl)-3,4,5,6-tetrahydrophthalamic acid cyclopentyl ester, N-(2,4-dichloro-5-methoxycarbonylphenyl)-N-(6-chloronicotinyl)-3,4,5,6-tetrahydrophthalamic acid-2-methoxyethyl ester, N-(2,4-dichloro-5-methoxycarbonylphenyl)-N-(4-methylnicotinyl)-3,4,5,6-tetrahydrophthalamic acid methyl ester, N-(2,4-dichloro-5-methoxycarbonylphenyl)-N-(4-methylnicotinyl)-3,4,5,6-tetrahydrophthalamic acid allyl ester, N-(2,4-dichloro-5-methoxycarbonylphenyl)-N-(4-methylnicotinyl)-3,4,5,6-tetrahydrophthalamic acid propargyl ester, N-(2,4-dichloro-5-methoxycarbonylphenyl)-N-(4-methylnicotinyl)-3,4,5,6-tetrahydrophthalamic acid cyclopentyl ester, N-(2,4-dichloro-5-methoxycarbonylphenyl)-N-(4-methylnicotinyl)-3,4,5,6-tetrahydrophthalamic acid-2-methoxyethyl ester, N-(2,4-dichloro-5-methoxycarbonylphenyl)-N-(5-methoxycarbonylnicotinyl)-3,4,5,6-tetrahydrophthalamic acid methyl ester, N-(2,4-dichloro-5-methoxycarbonylphenyl)-N-(5-methoxycarbonylnicotinyl)-3,4,5,6-tetrahydrophthalamic acid allyl ester, N-(2,4-dichloro-5-methoxycarbonylphenyl)-N-(5-methoxycarbonylnicotinyl)-3,4,5,6-tetrahydrophthalamic acid propargyl ester, N-(2,4-dichloro-5-methoxycarbonylphenyl)-N-(5-methoxycarbonylnicotinyl)-3,4,5,6-tetrahydrophthalamic acid cyclopentyl ester, N-(2,4-dichloro-5-methoxycarbonylphenyl)-N-(5-methoxycarbonylnicotinyl)-3,4,5,6-tetrahydrophthalamic acid-2-methoxyethyl ester, N-(2,4-dichloro-5-methoxycarbonylmethoxyphenyl)-N-nicotinyl-3,4,5,6-tetrahydrophthalamic acid methyl ester, N-(2,4-dichloro-5-methoxycarbonylmethoxyphenyl)-N-nicotinyl-3,4,5,6-tetrehydrophthalamic acid allyl ester, N-(2,4-dichloro-5-methoxycarbonylmethoxyphenyl)-N-nicotinyl-3,4,5,6-tetrehydrophthalamic acid propargyl ester, N-(2,4-dichloro-5-methoxycarbonylmethoxyphenyl)-N-nicotinyl-3,4,5,6-tetrehydrophthalamic acid cyclopentyl ester, N-(2,4-dichloro-5-methoxycarbonylmethoxyphenyl)-N-nicotinyl-3,4,5,6-tetrahydrophthalamic acid-2-methoxyethyl ester, N-(2,4-dichloro-5-methoxycarbonylmethoxyphenyl)-N-(6-chloronicotinyl)- 3,4,5,6-tetrahydrophthalamic acid methyl ester, N-(2,4-dichloro-5-methoxycarbonylmethoxyphenyl)-N-(6-chloronicotinyl)-3,4,5,6-tetrahydrophthalamic acid allyl ester, N-(2,4-dichloro-5-methoxycarbonylmethoxyphenyl)-N-(6-chloronicotinyl)-3,4,5,6-tetrahydrophthalamic acid propargyl ester, N-(2,4-dichloro-5-methoxycarbonylmethoxyphenyl)-N-(6-chloronicotinyl)-3,4,5,6-tetrehydrophthalamic acid cyclopentyl ester, N-(2,4-dichloro-5-methoxycarbonylmethoxyphenyl)-N-(6-chloronicotinyl)-3,4,5,6-tetrahydrophthalamic acid-2-methoxyethyl ester, N-(2,4-dichloro-5-methoxycarbonylmethoxyphenyl)-N-(4-methylnicotinyl)-3,4,5,6-tetrehydrophthalamic acid allyl ester, N-(2,4-dichloro-5-methoxycarbonylmethoxyphenyl)-N-(4-methylnicotinyl)-3,4,5,6-tetrehydrophthalamic acid propargyl ester, N-(2,4-dichloro-5-methoxycarbonylmethoxyphenyl)-N-(4-methylnicotinyl)-3,4,5,6-tetrehydrophthalamic acid cyclopentyl ester, N-(2,4-dichloro-5-methoxycarbonylmethoxyphenyl)-N-(4-methylnicotinyl)-3,4,5,6-tetrahydrophthalamic acid-2-methoxyethyl ester, N-(2,4-dichloro-5-methoxycarbonylmethoxyphenyl)-N-(5-methoxycarbonylnicotinyl)-3,4,5,6-tetrahydrophthalamic acid methyl ester, N-(2,4-dichloro-5-methoxycarbonylmethoxyphenyl)-N-(5-methoxycarbonylnicotinyl)-3,4,5,6-tetrahydrophthalamic acid allyl ester, N-(2,4-dichloro-5-methoxycarbonylmethoxyphenyl)-N-(5-methoxycarbonylnicotinyl)-3,4,5,6-tetrahydrophthalamic acid propargyl ester, N-(2,4-dichloro-5-methoxycarbonylmethoxyphenyl)-N-(5-methoxycarbonylnicotinyl)-3,4,5,6-tetrahydrophthalamic acid cyclopentyl ester, N-(2,4-dichloro-5-methoxycarbonylmethoxyphenyl)-N-(5-methoxycarbonylnicotinyl)-3,4,5,6-tetrahydrophthalamic acid-2-methoxyethyl ester, N-(2,4-dichloro-5-methoxycarbonylmethylthiophenyl)-N-nicotinyl-3,4,5,6-tetrahydrophthalamic acid methyl ester, N-(2,4-dichloro-5-methoxycarbonylmethylthiophenyl)-N-nicotinyl-3,4,5,6-tetrahydrophthalamic acid allyl ester, N-(2,4-dichloro-5-methoxycarbonylmethylthiophenyl)-N-nicotinyl-3,4,5,6-tetrahydrophthalamic acid propargyl ester, N-(2,4-dichloro-5-methoxycarbonylmethylthiophenyl)-N-nicotinyl-3,4,5,6-tetrahydrophthalamic acid cyclopentyl ester, N-(2,4-dichloro-5-methoxycarbonylmethylthiophenyl)-N-nicotinyl-3,4,5,6-tetrehydrophthalamic acid-2-methoxyethyl ester, N-(2,4-dichloro-5-methoxycarbonylmethylthiophenyl)-N-(6-chloronicotinyl)-3,4,5,6-tetrahydrophthalamic acid methyl ester, N-(2,4-dichloro-5-methoxycarbonylmethylthiophenyl)-N-(6-chloronicotinyl)-3,4,5,6-tetrahydrophthalamic acid allyl ester, N-(2,4-dichloro-5-methoxycarbonylmethylthiophenyl)-N-(6-chloronicotinyl)-3,4,5,6-tetrahydrophthalamic acid propargyl ester, N-(2,4-dichloro-5-methoxycarbonylmethylthiophenyl)-N-(6-chloronicotinyl)-3,4,5,6-tetrahydrophthalamic acid cyclopentyl ester, N-(2,4-dichloro-5-methoxycarbonylmethylthiophenyl)-N-(6-chloronicotinyl)-3,4,5,6-tetrahydrophthalamic acid-2-methoxyethyl ester, N-(2,4-dichloro-5-methoxycarbonylmethylthiophenyl)-N-(4-methylnicotinyl)-3,4,5,6-tetrahydrophthalamic acid methyl ester, N-(2,4-dichloro-5-methoxycarbonylamethylthiophenyl)-N-(4-methylnicotinyl)-3,4,5,6-tetrehydrophthalamic acid allyl ester, N-(2,4-dichloro-5-methoxycarbonylmethylthiophenyl)-N-(4-methylnicotinyl)-3,4,5,6-tetrahydrophthalamic acid propargyl ester, N-(2,4-dichloro-5-methoxycarbonylmethylthiophenyl)-N-(4-methylnicotinyl)-3,4,5,6-tetrehydrophthalamic acid cyclopentyl ester, N-(2,4-dichloro-5-methoxycarbonylmethylthiophenyl)-N-(4-methylnicotinyl)-3,4,5,6-tetrahydrophthalamic acid-2-methoxyethyl ester, N-(2,4-dichloro-5-methoxycarbonylmethylthiophenyl)-N-(5-methoxycarbonylnicotinyl)-3,4,5,6-tetrehydrophthalamic acid methyl ester, N-(2,4-dichloro-5-methoxycarbonylmethylthiophenyl)-N-(5-methoxycarbonylnicotinyl)-3,4,5,6-tetrahydrophthalamic acid allyl ester, N-(2,4-dichloro-5-methoxycarbonylmethylthiophenyl)-N-(5- methoxycarbonylnicotinyl)-3,4,5,6-tetrahydrophthalamic acid propargyl ester, N-(2,4-dichloro-5-methoxycarbonylmethylthiophenyl)-N-(5-methoxycarbonylnicotinyl)-3,4,5,6-tetrehydrophthalamic acid cyclopentyl ester, N-(2,4-dichloro-5-methoxycarbonylmethylthiophenyl)-N-(5-methoxycarbonylnicotinyl)-3,4,5,6-tetrahydrophthalamic acid-2-methoxyethyl ester, N-(4-chloro-2-fluoro-5-methoxyphenyl)-N-(2thiophenecarboxy)-3,4,5,6-tetrahydrophthalamic acid methyl ester, N-(4-chloro-2-fluoro-5-methoxyphenyl)-N-(2thiophenecarboxy)-3,4,5,6-tetrahydrophthalamic acid allyl ester, N-(4-chloro-2-fluoro-5-methoxyphenyl)-N-(2-thiophenecarboxy)-3,4,5,6-tetrahydrophthalamic acid propargyl ester, N-(4-chloro-2-fluoro-5-methoxyphenyl)-N-(2-thiophenecarboxy)-3,4,5,6-tetrahydrophthalamic acid cyclopentyl ester, N-(4-chloro-2-fluoro-5-methoxyphenyl)-N-(2-thiophenecarboxy)-3,4,5,6-tetrahydrophthalamic acid-2-methoxyethyl ester, N-(4-chloro-2-fluoro-5-methoxyphenyl)-N-(5-chloro-2-thiophenecarboxy)-3,4,5,6-tetrahydrophthalamic acid methyl ester, N-(4-chloro-2-fluoro-5-methoxyphenyl)-N-(5-chloro-2-thiophenecarboxy)-3,4,5,6-tetrahydrophthalamic acid allyl ester, N-(4-chloro-2-fluoro-5-methoxyphenyl)-N-(5-chloro-2-thiophenecarboxy)-3,4,5,6-tetrahydrophthalamic acid propargyl ester, N-(4-chloro-2-fluoro-5-methoxyphenyl)-N-(5-chloro-2-thiophenecarboxy)-3,4,5,6-tetrahydrophthalamic acid cyclopentyl ester, N-(4-chloro-2-fluoro-5-methoxyphenyl)-N-(5-chloro-2-thiophenecarboxy)-3,4,5,6-tetrahydrophthalamic acid-2-methoxyethyl ester, N-(4-chloro-2-fluoro-5-methoxyphenyl)-N-(5-methyl-2-thiophenecarboxy)-3,4,5,6-tetrahydrophthalamic acid methyl ester, N-(4-chloro-2-fluoro-5-methoxyphenyl)-N-(5-methyl-2thiophenecarboxy)-3,4,5,6-tetrahydrophthalamic acid allyl ester, N-(4-chloro-2-fluoro-5-methoxyphenyl)-N-(5-methyl-2thiophenecarboxy)-3,4,5,6-tetrahydrophthalamic acid propargyl ester, N-(4-chloro-2-fluoro-5-methoxyphenyl)-N-(5-methyl-2thiophenecarboxy)-3,4,5,6-tetrahydrophthalamic acid cyclopentyl ester, N-(4-chloro-2-fluoro-5-methoxyphenyl)-N-(5-methyl-2thiophenecarboxy)-3,4,5,6-tetrahydrophthalamic acid-2-methoxyethyl ester, N-(4-chloro-2-fluoro-5-allyloxyphenyl)-N-(2-thiophenecarboxy)-3,4,5,6-tetrahydrophthalamic acid methyl ester, N-(4-chloro-2-fluoro-5-allyloxyphenyl)-N-(2-thiophenecarboxy)-3,4,5,6-tetrahydrophthalamic acid allyl ester, N-(4-chloro-2-fluoro-5-allyloxyphenyl)-N-(2-thiophenecarboxy)-3,4,5,6-tetrahydrophthalamic acid propargyl ester, N-(4-chloro-2-fluoro-5-allyloxyphenyl)-N-(2-thiophenecarboxyl)-3,4,5,6-tetrehydrophthalamic acid cyclopentyl ester, N-(4-chloro-2-fluoro-5-allyloxyphenyl)-N-(2-thiophenecarboxy)-3,4,5,6-tetrahydrophthalamic acid-2-methoxyethyl ester, N-(4-chloro-2-fluoro-5-allyloxyphenyl)-N-(5-chloro-2-thiophenecarboxy)-3,4,5,6-tetrahydrophthalamic acid methyl ester, N-(4-chloro-2-fluoro-5-allyloxyphenyl)-N-(5-chloro-2-thiophenecarboxy)-3,4,5,6-tetrahydrophthalamic acid allyl ester, N-(4-chloro-2-fluoro-5-allyloxyphenyl)-N-(5-chloro-2-thiophenecarboxy)-3,4,5,6-tetrahydrophthalamic acid propargyl ester, N-(4-chloro-2-fluoro-5-allyloxyphenyl)-N-(5-chloro-2-thiophenecarboxy)-3,4,5,6-tetrahydrophthalamic acid cyclopentyl ester, N-(4-chloro-2-fluoro-5-allyloxyphenyl)-N-(5-chloro-2-thiophenecarboxy)-3,4,5,6-tetrahydrophthalamic acid-2-methoxyethyl ester, N-(4-chloro-2-fluoro-5-allyloxyphenyl)-N-(5-methyl-2-thiophenecarboxy)-3,4,5,6-tetrahydrophthalamic acid methyl ester, N-(4-chloro-2-fluoro-5-allyloxyphenyl)-N-(5-methyl-2-thiophenecarboxy)-3,4,5,6-tetrahydrophthalamic acid allyl ester, N-(4-chloro-2-fluoro-5-allyloxyphenyl)-N-(5-methyl-2-thiophenecarboxy)-3,4,5,6-tetrahydrophthalamic acid propargyl ester, N-(4-chloro-2-fluoro-5-allyloxyphenyl)-N-(5-methyl-2-thiophenecarboxy)-3,4,5,6-tetrahydrophthalamic acid cyclopentyl ester, N-(4-chloro-2-fluoro-5-allyloxyphenyl)-N-(5-methyl-2-thiophenecarboxy)-3,4,5,6-tetrahydrophalamic acid-2-methoxyethyl ester, N-[4-chloro-2-fluoro-5-(1-methylpropargyloxy)phenyl]-N-(2-thiophenecarboxy)-3,4,5,6-tetrahydrophthalamic acid methyl ester, N-[4-chloro-2-fluoro-5-(1-methylpropargyloxy)phenyl]-N-(2-thiophenecarboxy)-3,4,5,6-tetrehydrophthalamic acid allyl ester, N-[4-chloro-2-fluoro-5-(1-methylpropargyloxy)phenyl]-N-(2-thiophenecarboxy)-3,4,5,6-tetrehydrophthalamic acid propargyl ester, N-[4-chloro-2-fluoro5-(1-methylpropargyloxy)phenyl]-N-(2-thiophenecarboxy)-3,4,5,6-tetrahydrophthalamic acid cyclopentyl ester, N-[4-chloro-2-fluoro-5-(1-methylpropargyloxy)phenyl]-N-(2-thiophenecarboxy)-3,4,5,6-tetrahydrophthalamic acid-2-methoxyethyl ester, N-[4-chloro-2-fluoro-5-(1-methylpropargyloxy)phenyl]-N-(5-chloro-2-thiophenecarboxy)-3,4,5,6-tetrahydrophthalamic acid methyl ester, N-[4-chloro-2-fluoro-5-(1-methylpropargyloxy)phenyl]-N-(5-chloro-2-thiophenecarboxy)-3,4,5,6-tetrahydrophthalamic acid allyl ester, N-[4-chloro-2-fluoro-5-(1-methylpropargyloxy)phenyl]-N-(5-chloro-2-thiophenecarboxy)-3,4,5,6-tetrahydrophthalamic acid propargyl ester, N-[4-chloro-2-fluoro-5-(1-methylpropargyloxy)phenyl]-N-(5-chloro-2thiophenecarboxy)-3,4,5,6-tetrahydrophthalamic acid cyclopentyl ester, N-[4-chloro-2-fluoro-5-(1-methylpropargyloxy)phenyl]-N-5-(5-chloro-2-thiophenecarboxy)-3,4,5,6-tetrahydrophthalamic acid-2-methoxyethyl ester, N-[4-chloro-2-fluoro-5-(1-methylpropargyloxy)phenyl]-N-(5-methyl-2-thiophenecarboxy)-3,4,5,6-tetrahydrophthalamic acid methyl ester, N-[4-chloro-2-fluoro-5-(1-methylpropargyloxy)phenyl]-N-(5-methyl-2thiophenecarboxy)-3,4,5,6-tetrahydrophthalamic acid allyl ester, N-[4-chloro-2-fluoro-5-(1-methylpropargyloxy)phenyl]-N-(5-methyl-2-thiophenecarboxy)-3,4,5,6-tetrahydrophthalamic acid propargyl ester, N-[4-chloro-2-fluoro-5-(1-methylpropargyloxy)phenyl]-N-(5-methyl-2-thiophenecarboxy)-3,4,5,6-tetrahydrophthalamic acid cyclopentyl ester, N-[4-chloro-2-fluoro-5-(1-methylpropargyloxy)phenyl]-N-(5-methyl-2-thiophenecarboxy)-3,4,5,6-tetrahydrophthalamic acid-2-methoxyethyl ester, N-(4-chloro-2-fluoro-5-cyclopentyloxyphenyl)-N-(2-thiophenecarboxy)-3,4,5,6-tetrahydrophthalamic acid methyl ester, N-(4-chloro-2-fluoro-5-cyclopentyloxyphenyl)-N-(2-thiophenecarboxy)-3,4,5,6-tetrahydrophthalamic acid allyl ester, N-(4-chloro-2-fluoro-5-cyclopentyloxyphenyl)-N-(2-thiophenecarboxy)-3,4,5,6-tetrahydrophthalamic acid propargyl ester, N-(4-chloro-2-fluoro-5-cyclopentyloxyphenyl)-N-(2-thiophenecarboxy)-3,4,5,6-tetrahydrophthalamic acid cyclopentyl ester, N-(4-chloro-2-fluoro-5-cyclopentyloxyphenyl)-5-N-(2-thiophenecarboxy)-3,4,5,6-tetrahydrophthalamic acid-2-methoxyethyl ester, N-(4-chloro-2-fluoro-5-cyclopentyloxyphenyl)-N-(5-chloro-2-thiophenecarboxy)-3,4,5,6-tetrahydrophthalamic acid methyl ester, N-(4-chloro-2-fluoro-5cyclopentyloxyphenyl)-N-(5-chloro-2-thiophenecarboxy)-3,4,5,6-tetrehydrophthalamic acid allyl ester, N-(4-chloro-2-fluoro-5cyclopentyloxyphenyl)-N-(5-chloro-2- thiophenecarboxy)-3,4,5,6-tetrahydrophthalamic acid propargyl ester, N-(4-chloro-2-fluoro-5-cyclopentyloxyphenyl)-N-(5-chloro-2-thiophenecarboxy)-3,4,5,6-tetrahydrophthalamic acid cyclopentyl ester, N-(4-chloro-2-fluoro-5-cyclopentyloxyphenyl)-N-(5-chloro-2-thiophenecarboxy)-3,4,5,6-tetrahydrophthalamic acid-2-methoxyethyl ester, N-(4-chloro-2-fluoro-5-cyclopentyloxyphenyl)-N-(5-methyl-2-thiophenecarboxy)-3,4,5,6-tetrahydrophthalamic acid methyl ester, N-(4-chloro-2-fluoro-5-cyclopentyloxyphenyl)-N-(5-methyl-2-thiophenecarboxy)-3,4,5,6-tetrahydrophthalamic acid allyl ester, N-(4-chloro-2-fluoro-5-cyclopentyloxyphenyl)-N-(5-methyl-2-thiophenecarboxy)-3,4,5,6-tetrahydrophthalamic acid propargyl ester, N-(4-chloro-2-fluoro-5-cyclopentyloxyphenyl)-N-(5-methyl-2-thiophenecarboxy)-3,4,5,6-tetrehydrophthalamic acid cyclopentyl ester, N-(4-chloro-2-fluoro-5-cyclopentyloxyphenyl)-N-(5-methyl-2thiophenecarboxy)-3,4,5,6-tetrahydrophthalamic acid-2-methoxyethyl ester, N-(4-chloro-2-fluoro-5-methoxycarbonylmethoxyphenyl)-N-(2-thiophenecarboxy)-3,4,5,6-tetrahydrophthalamic acid methyl ester, N-(4-chloro-2-fluoro-5-methoxycarbonylmethoxyphenyl)-N-(2-thiophenecarboxy)-3,4,5,6-tetrahydrophthalamic acid allyl ester, N-(4-chloro-2-fluoro-5-methoxycarbonylmethoxyphenyl)-N-(2thiophenecarboxy)-3,4,5,6-tetrahydrophthalamic acid propargyl ester, N-(4-chloro-2-fluoro-5-methoxycarbonylmethoxyphenyl)-N-(2-thiophenecarboxy)- 3,4,5,6-tetrahydrophthalamic acid cyclopentyl ester, N-(4-chloro-2-fluoro-5-methoxycarbonylmethoxyphenyl)-N-(2-thiophenecarboxy)-3,4,5,6-tetrahydrophthalamic acid-2-methoxyethyl ester, N-(4-chloro-2-fluoro-5-methoxycarbonylmethoxyphenyl)-N-(5-chloro-2-thiophenecarboxy)-3,4,5,6-tetrahydrophthalamic acid methyl ester, N-(4-chloro-2-fluoro-5-methoxycarbonylmethoxyphenyl)-N-(5-chloro-2-thiophenecarboxy)-3,4,5,6-tetrahydrophthalamic acid allyl ester, N-(4-chloro-2-fluoro-5-methoxycarbonylmethoxyphenyl)-N-(5-chloro-2-thiophenecarboxy)-3,4,5,6-tetrahydrophthalamic acid propargyl ester, N-(4-chloro-2-fluoro-5-methoxycarbonylmethoxyphenyl)-N-(5-chloro-2-thiophenecarboxy)-3,4,5,6-tetrahydrophthalamic acid cyclopentyl ester, N-(4-chloro-2-fluoro-5-methoxycarbonylmethoxyphenyl)-N-(5-chloro-2-thiophenecarboxy)-3,4,5,6-tetrahydrophthalamic acid-2-methoxyethyl ester, N-(4-chloro-2-fluoro-5-methoxycarbonylmethoxyphenyl)-N-(5-methyl-2-thiophenecarboxy)-3,4,5,6-tetrehydrophthalamic acid methyl ester, N-(4-chloro-2-fluoro-5-methoxycarbonylmethoxyphenyl)-N-(5-methyl-2-thiophenecarboxy)-3,4,5,6-tetrahydrophthalamic acid allyl ester, N-(4-chloro-2-fluoro-5-methoxycarbonylmethoxyphenyl)-N-(5-methyl-2-thiophenecarboxy)-3,4,5,6-tetrahydrophthalamic acid propargyl ester, N-(4-chloro-2-fluoro-5-methoxycarbonylmethoxyphenyl)-N-(5-methyl-2-thiophenecarboxy)-3,4,5,6-tetrehydrophthalamic acid cyclopentyl ester, N-(4-chloro-2-fluoro-5-methoxycarbonylmethoxyphenyl)-N-(5-methyl-2-thiophenecarboxy)-3,4,5,6-tetrahydrophthalamic acid-2-methoxyethyl ester, N-(4-chloro-2-fluoro-5-methoxyphenyl)-N-(3-thiophenecarboxy)-3,4,5,6-tetrahydrophthalamic acid methyl ester, N-(4-chloro-2-fluoro-5-methoxyphenyl)-N-(3-thiophenecarboxy)-3,4,5,6-tetrahydrophthalamic acid allyl ester, N-(4-chloro-2-fluoro-5-methoxyphenyl)-N-(3-thiophenecarboxy)-3,4,5,6-tetrahydrophthalamic acid propargyl ester, N-(4-chloro-2-fluoro-5-methoxyphenyl)-N-(3-thiophenecarboxy)-3,4,5,6-tetrehydrophthalamic acid cyclopentyl ester, N-(4-chloro-2-fluoro-5-methoxyphenyl)-N-( 3-thiophenecarboxy)-3,4,5,6-tetrehydrophthalamic acid-2-methoxyethyl ester, N-(4-chloro-2-fluoro-5-methoxyphenyl)-N-(5-chloro-3-thiophenecarboxy)-3,4,5,6-tetrahydrophthalamic acid methyl ester, N-(4-chloro-2-fluoro-5-methoxyphenyl)-N-(5-chloro-3-thiophenecarboxy)-3,4,5,6-tetrahydrophthalamic acid allyl ester, N-(4-chloro-2-fluoro-5-methoxyphenyl)-N-(5-chloro-3-thiophenecarboxy)-3,4,5,6-tetrahydrophthalamic acid propargyl ester, N-(4-chloro-2-fluoro-5-methoxyphenyl)-N-(5-chloro-3-thiophenecarboxy)-3,4,5,6-tetrahydrophthalamic acid cyclopentyl ester, N-(4-chloro-2-fluoro-5-methoxyphenyl)-N-(5-chloro-3-thiophenecarboxy)-3,4,5,6-tetrahydrophthalamic acid-2-methoxyethyl ester, N-(4-chloro-2-fluoro-5-methoxyphenyl)-N-(5-methyl-3-thiophenecarboxy)-3,4,5,6-tetrahydrophthalamic acid methyl ester, N-(4-chloro-2-fluoro-5-methoxyphenyl)-N-(5-methyl-3-thiophenecarboxy)-3,4,5,6-tetrahydrophthalamic acid allyl ester, N-(4-chloro-2-fluoro-5-methoxyphenyl)-N-(5-methyl-3-thiophenecarboxy)-3,4,5,6-tetrahydrophthalamic acid propargyl ester, N-(4-chloro-2-fluoro-5-methoxyphenyl)-N-(5-methyl-3-thiophenecarboxy)-3,4,5,6-tetrahydrophthalamic acid cyclopentyl ester, N-(4-chloro-2-fluoro-5-methoxyphenyl)-N-(5-methyl-3-thiophenecarboxy)-3,4,5,6-tetrahydrophthalamic acid-2-methoxyethyl ester, N-(4-chloro-2-fluoro-5-allyloxyphenyl)-N-(3-thiophenecarboxy)-3,4,5,6-tetrahydrophthalamic acid methyl ester, N-(4-chloro-2-fluoro-5-allyloxyphenyl)-N-(3-thiophenecarboxy)-3,4,5,6-tetrahydrophthalamic acid allyl ester, N-(4-chloro-2-fluoro-5-allyloxyphenyl)-N-(3-thiophenecarboxy)-3,4,5,6-tetrehydrophthalamic acid propargyl ester, N-(4-chloro-2-fluoro5-allyloxyphenyl)-N-(3-thiophenecarboxy)-3,4,5,6-tetrahydrophthalamic acid cyclopentyl ester, N-(4-chloro-2-fluoro-5-allyloxyphenyl)-N-(3-thiophenecarboxy)-3,4,5,6-tetrahydrophthalamic acid-2-methoxyethyl ester, N-(4-chloro-2-fluoro-5-allyloxyphenyl)-N-(5-chloro-3-thiophenecarboxy)-3,4,5,6-tetrehydrophthalamic acid methyl ester, N-(4-chloro-2-fluoro-5-allyloxyphenyl)-N-(5-chloro-3-thiophenecarboxy)-3,4,5,6-tetrehydrophthalamic acid allyl ester, N-(4-chloro-2-fluoro-5-allyloxyphenyl)-N-(5-chloro-3-thiophenecarboxy)-3,4,5,6-tetrehydrophthalamic acid propargyl ester, N-(4-chloro-2-fluoro5-allyloxyphenyl)-N-(5-chloro-3-thiophenecarboxy)-3,4,5,6-tetrehydrophthalamic acid cyclopentyl ester, N-(4-chloro-2-fluoro-5-allyloxyphenyl)-N-(5-chloro-3-thiophenecarboxy)-3,4,5,6-tetrahydrophthalamic acid-2-methoxyethyl ester, N-(4-chloro-2-fluoro-5-allyloxyphenyl)-N-(5-methyl-3-thiophenecarboxy)-3,4,5,6-tetrahydrophthalamic acid methyl ester, N-(4-chloro-2-fluoro-5-allyloxyphenyl)-N-(5-methyl-3-thiophenecarboxy)-3,4,5,6-tetrahydrophthalamic acid allyl ester, N-(4-chloro-2-fluoro-5-allyloxyphenyl)-N-(5-methyl-3-thiophenecarboxy)-3,4,5,6-tetrahydrophthalamic acid propargyl ester, N-(4-chloro-2-fluoro-5-allyloxyphenyl)-N-(5-methyl-3-thiophenecarboxy)-3,4,5,6-tetrahydrophthalamic acid cyclopentyl ester, N-(4-chloro-2-fluoro-5-allyloxyphenyl)-N-(5-methyl-3-thiophenecarboxy)-3,4,5,6-tetrahydrophthalamic acid-2-methoxyethyl ester, N-[4-chloro-2-fluoro-5-(1-methylpropargyloxy)phenyl]-N-(3-thiophenecarboxy)-3,4,5,6-tetrahydrophthalamic acid methyl ester, N-[4-chloro-2-fluoro-5-(1-methylpropargyloxy)phenyl]-N-(3-thiophenecarboxy)-3,4,5,6-tetrahydrophthalamic acid allyl ester, N-[4-chloro-2-fluoro-5-(1-methylpropargyloxy)phenyl]-N-(3-thiophenecarboxy)-3,4,5,6-tetrahydrophthalamic acid propargyl ester, N-[4-chloro-2-fluoro-5-(1-methylpropargyloxy)phenyl]-N-(3-thiophenecarboxy)-3,4,5,6-tetrahydrophthalamic acid cyclopentyl ester, N-[4-chloro-2-fluoro-5-(1-methylpropargyloxy)phenyl]-N-(3-thiophenecarboxy)-3,4,5,6-tetrahydrophthalamic acid-2-methoxyethyl ester, N-[4-chloro-2-fluoro-5-(1-methylpropargyloxy)phenyl]-N-(5-chloro-3thiophenecarboxy)-3,4,5,6-tetrahydrophthalamic acid methyl ester, N-[4-chloro-2-fluoro-5-(1-methylpropargyloxy)phenyll-N-(5-chloro-3-thiophenecarboxy)-3,4,5,6-tetrahydrophthalamic acid allyl ester, N-[4-chloro-2-fluoro-5-(1-methylpropargyloxy)phenyl]-N-(5-chloro-3-thiophenecarboxy)-3,4,5,6-tetrahydrophthalamic acid propargyl ester, N-[4-chloro-2-fluoro-5-(1-methylpropargyloxy)phenyl]-N-( 5-chloro-3-thiophenecarboxy)-3,4,5,6-tetrahydrophthalamic acid cyclopentyl ester, N-[4-chloro-2-fluoro-5-(1-methylpropargyloxy)phenyl]-N-(5-chloro-3thiophenecarboxy)-3,4,5,6-tetrahydrophthalamic acid-2-methoxyethyl ester, N-[4-chloro-2-fluoro-5-(1-methylpropargyloxy)phenyl]-N-(5-methyl-3-thiophenecarboxy)-3,4,5,6-tetrehydrophthalamic acid methyl ester, N-[4-chloro-2-fluoro-5-(1-methylpropargyloxy)phenyl]-N-(5-methyl-3-thiophenecarboxy)-3,4,5,6-tetrahydrophthalamic acid allyl ester, N-[4-chloro-2-fluoro-5-(1-methylpropargyloxy)phenyl]-N-(5-methyl3-thiophenecarboxy)-3,4,5,6-tetrahydrophthalamic acid propargyl ester, N-[4-chloro-2-fluoro-5-(1-methylpropargyloxy)phenyl]-N-(5-methyl-3-thiophenecarboxy)-3,4,5,6-tetrahydrophthalamic acid cyclopentyl ester, N-[4-chloro-2-fluoro-5-(1-methylpropargyloxy)phenyl]-N-(5-methyl-3-thiophenecarboxy)-3,4,5,6-tetrahydrophthalamic acid-2-methoxyethyl ester, N-(4-chloro-2-fluoro-5-cyclopentyloxyphenyl)-N-(3-thiophenecarboxy)-3,4,5,6-tetrahydrophthalamic acid methyl ester, N-(4-chloro-2-fluoro-5-cyclopentyloxyphenyl)-N-(3-thiophenecarboxy)-3,4,5,6-tetrahydrophthalamic acid allyl ester, N-(4-chloro-2-fluoro-5-cyclopentyloxyphenyl)-N-(3-thiophenecarboxy)-3,4,5,6-tetrahydrophthalamic acid propargyl ester, N-(4-chloro-2-fluoro-5-cyclopentyloxyphenyl)-N-(3-thiophenecarboxy)-3,4,5,6-tetrahydrophthalamic acid cyclopentyl ester, N-(4-chloro-2-fluoro-5-cyclopentyloxyphenyl)-N-(3-thiophenecarboxy)-3,4,5,6-tetrahydrophthalamic acid-2-methoxyethyl ester, N-(4-chloro-2-fluoro-5-cyclopentyloxyphenyl)-N-(5-chloro-3-thiophenecarboxy)-3,4,5,6-tetrahydrophthalamic acid methyl ester, N-(4-chloro-2-fluoro-5-cyclopentyloxyphenyl)-N-(5-chloro-3-thiophenecarboxy)-3,4,5,6-tetrahydrophthalamic acid allyl ester, N-(4-chloro-2-fluoro-5-cyclopentyloxyphenyl)-N-(5-chloro-3-thiophenecarboxy)-3,4,5,6-tetrahydrophthalamic acid propargyl ester, N-(4-chloro-2-fluoro-5-cyclopentyloxyphenyl)-N-(5-chloro-3-thiophenecarboxy)-3,4,5,6-tetrahydrophthalamic acid cyclopentyl ester, N-(4-chloro-2-fluoro- 5-cyclopentyloxyphenyl)-N-(5-chloro-3-thiophenecarboxy)-3,4,5,6-tetrahydrophthalamic acid-2-methoxyethyl ester, N-(4-chloro-2-fluoro-5-cyclopentyloxyphenyl)-N-(5-methyl-3-thiophenecarboxy)-3,4,5,65-tetrehydrophthalamic acid methyl ester, N-(4-chloro-2-fluoro-5cyclopentyloxyphenyl)-N-(5-methyl-3-thiophenecarboxy)-3,4,5,6-tetrahydrophthalamic acid allyl ester, N-(4-chloro-2-fluoro-5-cyclopentyloxyphenyl)-N-(5-methyl-3-thiophenecarboxy)-3,4,5,6-tetrahydrophthalamic acid propargyl ester, N-(4-chloro-2-fluoro-5-cyclopentyloxyphenyl)-N-(5-methyl-3thiophenecarboxy)-3,4,5,6-tetrahydrophthalamic acid cyclopentyl ester, N-(4-chloro-2-fluoro-5-cyclopentyloxyphenyl)-N-(5-methyl-3-thiophenecarboxy)-3,4,5,6-tetrahydrophthalamic acid2-methoxyethyl ester, N-(4-chloro-2-fluoro-5-methoxycarbonylmethoxyphenyl)-N-(3-thiophenecarboxy)-3,4,5,6-tetrahydrophthalamic acid methyl ester, N-(4-chloro-2-fluoro-5-methoxycarbonylmethoxyphenyl)-N-(3-thiophenecarboxy)-3,4,5,6-tetrahydrophthalamic acid allyl ester, N-(4-chloro-2-fluoro-5-methoxycarbonylmethoxyphenyl)-N-(3-thiophenecarboxy)-3,4,5,6-tetrahydrophthalamic acid propargyl ester, N-(4-chloro-2-fluoro-5-methoxycarbonylmethoxyphenyl)-N-(3-thiophenecarboxy)-3,4,5,6-tetrahydrophthalamic acid cyclopentyl ester, N-(4-chloro-2-fluoro-5-methoxycarbonylmethoxyphenyl)-N-(3-thiophenecarboxy)-3,4,5,6-tetrahydrophthalamic acid-2-methoxyethyl ester, N-(4-chloro-2-fluoro-5-methoxycarbonylmethoxyphenyl)-N-(5-chloro-3-thiophenecarboxy)-3,4,5,6-tetrahydrophthalamic acid methyl ester, N-(4-chloro-2-fluoro-5-methoxycarbonylmethoxyphenyl)-N-(5-chloro-3-thiophenecarboxy)-3,4,5,6-tetrahydrophthalamic acid allyl ester, N-(4-chloro-2-fluoro-5-methoxycarbonylmethoxyphenyl)-N-(5-chloro-3-thiophenecarboxy)-3,4,5,6-tetrahydrophthalamic acid propargyl ester, N-(4-chloro-2-fluoro-5-methoxycarbonylmethoxyphenyl)-N-(5-chloro-3-thiophenecarboxy)-3,4,5,6-tetrahydrophthalamic acid cyclopentyl ester, N-(4-chloro-2-fluoro-5-methoxycarbonylmethoxyphenyl)-N-(5-chloro3thiophenecarboxy)-3,4,5,6-tetrahydrophthalamic acid-2-methoxyethyl ester, N-(4-chloro-2-fluoro-5-methoxycarbonylmethoxyphenyl)-N-(5-methyl-3-thiophenecarboxy)-3,4,5,6-tetrehydrophthalamic acid methyl ester, N-(4-chloro-2-fluoro-5-methoxycarbonylmethoxyphenyl)-N-(5-methyl-3-thiophenecarboxy)-3,4,5,6-tetrahydrophthalamic acid allyl ester, N-(4-chloro-2-fluoro-5-methoxycarbonylmethoxyphenyl)-N-(5-methyl-3-thiophenecarboxy)-3,4,5,6-tetrahydrophthalamic acid propargyl ester, N-(4-chloro-2-fluoro-5-methoxycarbonylmethoxyphenyl)-N-(5-methyl-3-thiophenecarboxy)-3,4,5,6-tetrahydrophthalamic acid cyclopentyl ester, N-(4-chloro-2-fluoro-5-methoxycarbonylmethoxyphenyl)-N-(5-methyl-3thiophenecarboxy)-3,4,5,6-tetrahydrophthalamic acid-2-methoxyethyl ester, and the like.

An N-phenyltetrahydrophthalamic acid derivative [I] which is a compound of the present invention can be produced, for example, as shown by the following formula, by reacting an imidoylchloride derivative represented by the general formula [III] with a carboxylic acid represented by the general formula [V],

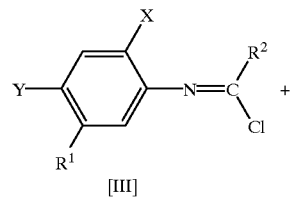

[III]

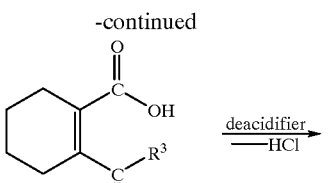

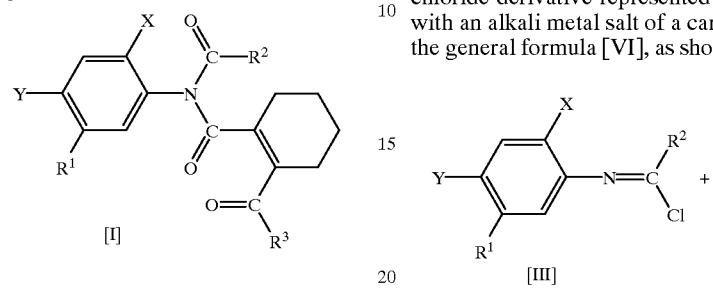

wherein X and Y each individually represent hydrogen atoms or halogen atoms, $R^1$ represents a lower alkoxycarbonylalkylthio group, $R^2$ represents a lower alkyl group, a halogenated lower alkyl group or a substituted or unsubstituted phenyl group, and $R^3$ represents a lower alkoxy group, a lower alkenyloxy group, a lower alkynyloxy group, or a lower alkoxyalkoxy group.

The reaction can proceed preferably without using any solvent or in a suitable solvent such as benzene, toluene, xylene, methylene chloride, chloroform, ethyl acetate, dioxane, tetrahydrofuran, diethyl ether, N,N-dimethylformamide or dimethylsulfoxide, by adding a suitable deacidifying agent such as an organic base such as triethylamine or pyridine, or an inorganic base such as potassium hydroxide or sodium hydroxide.

The present reaction is an equimolar reaction. Therefore, the molar ratio of an imidoylchloride derivative [III] to a carboxylic acid [V] is preferably about 1, and it is usually appropriately from 0.8 to 1.2. In case that it is less than 0.8, the imidoylchloride derivative [III] which has been added in an excessive amount remains unreacted in a large amount. In case that it is greater than 1.2 by mol, the carboxylic acid [V] which has been added in an excessive amount remains unreacted in a large amount. Therefore, it becomes impossible to effectively conduct the reaction, thereby causing an economical disadvantage. Furthermore, a burden in a purification process unpreferably increases, because it is necessary to remove or recover the unreacted imidoylchloride derivative [III] or unreacted carboxylic acid [V]. It is more preferably from 0.9 to 1.1 by mol.

In the present reaction, the addition of deacidifier in an amount of at least 1 by mol relative to the imidoylchloride derivative [III] suffices. It is usually appropriately from 1 to 3 by mol. Less than 1 by mol is not preferable, because the reaction does not proceed sufficiently, causing a lowering of the yield. Even if an amount greater than 3 by mol is added, the reaction does not change so much, causing only an economical disadvantage. Furthermore, a burden in a purification process unpreferably increases, because it is necessary to remove an excessive deacidifier. It is more preferably from 1 to 2 by mol.

The reaction temperature is not particularly limited, and it is usually appropriately from −20° C. to 200° C. A temperature lower than −20° C. is not preferable, because it is impossible to obtain a sufficient reaction rate. With this, the reaction time becomes very long, and thus it becomes impossible to efficiently conduct the reaction. A temperature higher than 200° C. is not preferable, because the decomposition becomes violent. This causes a lowering of the yield. Furthermore, a burden in a purification process unpreferably increases, because it is necessary to remove the degradation product(s). It is more preferably from 20° C. to 70° C.

It is also possible to produce an N-phenyltetrahydrophthalamic derivative [I] which is a compound of the present invention by reacting an imidoylchloride derivative represented by the general formula [III] with an alkali metal salt of a carboxylic acid, represented by the general formula [VI], as shown in the following formula.

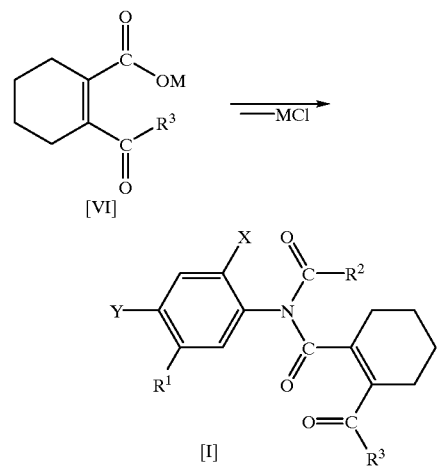

wherein X and Y each individually represent hydrogen atoms or halogen atoms, $R^1$ represents a lower alkoxycarbonylalkylthio group, $R^2$ represents a lower alkyl group, a halogenated lower alkyl group or a substituted or unsubstituted phenyl group, $R^3$ represents a lower alkoxy group, a lower alkenyloxy group, a lower alkynyloxy group, or a lower alkoxyalkoxy group, and M represents an alkali metal.

The reaction can preferably be conducted without using any solvent, or in a suitable solvent such as benzene, toluene, xylene, methylene chloride, chloroform, ethyl acetate, dioxane, tetrahydrofuran, diethyl ether, N,N-dimethylformamide, dimethylsulfoxide or water, if necessary, by adding a phase transfer catalyst.

The present reaction is an equimolar reaction. Therefore, the molar ratio of an alkali metal salt of carboxylic acid [VI] to an imidoylchloride derivative [III] is preferably about 1, and it is usually appropriately from 0.8 to 1.2. In case that it is less than 0.8, the imidoylchloride derivative [III] which has been added in an excessive amount remains unreacted in a large amount. In case that it is greater than 1.2, the alkali metal salt of carboxylic acid [VI] which has been added in an excessive amount remains unreacted in a large amount. Therefore, it becomes impossible to effectively conduct the reaction, thereby causing an economical disadvantage. Furthermore, a burden in a purification process unpreferably increases, because it is necessary to remove or recover the unreacted imidoylchloride derivative [III] or unreacted alkali metal salt of carboxylic acid [VI]. It is more preferably from 0.9 to 1.1 by mol.

As examples of a phase transfer catalyst used in the present reaction, it is possible to cite, for example, crown ethers such as 18-crown-6-ether, polyethers such as polyethylene glycol, quaternary phosphonium salts such as tetraphenylphosphonium chloride, and quaternary ammonium salts such as tetrabutylammonium bromide and tetrabutylammonium hydrogensulfate.

The amount of the phase transfer catalyst to be used is not particularly limited and may arbitrarily be adjusted depending on the desired reaction rate. It is usually appropriately from 0.01 mol % to 20 mol % relative to the imidoylchloride derivative [III]. Less than 0.01 mol % is not preferable, because it is impossible to obtain a sufficient reaction rate. With this, the reaction time becomes very long, and thus it becomes impossible to efficiently conduct the reaction. Even if an amount greater than 20 mol % is added, the reaction does not change so much, causing only an economical disadvantage. Thus, this is not preferable. It is more preferably from 0.1 mol % to 10 mol %.

The reaction temperature is not particularly limited, and it is usually appropriately from 0° C. to 200° C. A temperature lower than 0° C. is not preferable, because it is impossible to obtain a sufficient reaction rate. With this, the reaction time becomes very long, and thus it becomes impossible to efficiently conduct the reaction. A temperature higher than 200° C. is not preferable, because the decomposition becomes violent. This causes a lowering of yield. Furthermore, a burden in a purification process unpreferably increases, because it is necessary to remove the degradation product. It is preferably from 0° C. to 100° C. for more efficiently conducting the reaction.

It is possible to produce an N-phenyltetrahydrophthalamic derivative [II] which is a compound of the present invention, for example, by reacting an imidoylchloride derivative represented by the general formula [IV] with a carboxylic acid represented by the general formula [VII], as shown in the following formula.

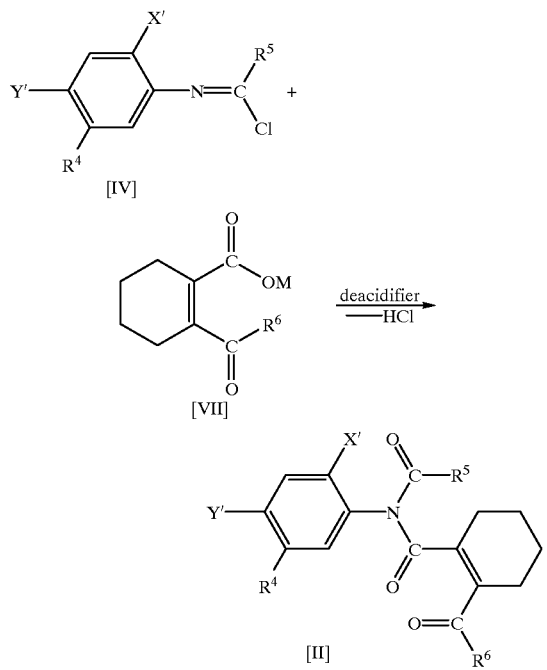

wherein X' and Y' each individually represent hydrogen atoms or halogen atoms, $R^4$ represents a hydrogen atom, a lower alkoxy group, a lower alkenyloxy group, a lower alkynyloxy group, cycloalkyloxy group, a lower alkoxycarbonyl group, a lower alkoxycarbonylalkoxy group or a lower alkoxycarbonylalkylthio group, $R^5$ represents:

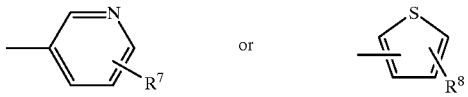

wherein $R^7$ represents a hydrogen atom, a halogen atom, a lower alkyl group or a lower alkoxycarbonyl group, and $R^8$ represents a hydrogen atom, a halogen atom or a lower alkyl group and $R^6$ represents a lower alkoxy group, a lower alkenyloxy group, a lower alkynyloxy group, a cycloalkyloxy group or a lower alkoxyalkoxy group.

The reaction can preferably be conducted without using any solvent, or in a suitable solvent such as benzene, toluene, xylene, methylene chloride, chloroform, ethyl acetate, dioxane, tetrahydrofuran, diethyl ether, N,N-dimethylformamide or dimethylsulfoxide, by adding a suitable deacidifier, for example, an organic base such as triethylamine or pyridine, or an inorganic base such as potassium hydroxide or sodium hydroxide.

The present reaction is an equimolar reaction. Therefore, the molar ratio of a carboxylic acid [VII] to an imidoylchloride derivative [IV] is preferably about 1, and it is usually appropriately from 0.8 to 1.2. In case that it is less than 0.8 by mol, the imidoylchloride derivative [IV] which has been added in an excessive amount remains unreacted in a large amount. In case that it is greater than 1.2 by mol, the carboxylic acid [VII] which has been added in an excessive amount remains unreacted in a large amount. Therefore, it becomes impossible to effectively conduct the reaction, thereby to cause an economical disadvantage. Furthermore, a burden in a purification process unpreferably increases, because it is necessary to remove or recover the unreacted imidoylchloride derivative [IV] or unreacted carboxylic acid [VII]. It is more preferably from 0.9 to 1.1 by mol.

In the present reaction, the addition of deacidifier in an amount of at least 1 by mol relative to the imidoylchloride derivative [IV] suffices. It is usually appropriately from 1 to 3 by mol. Less than 1 by mol is not preferable, because the reaction does not proceed sufficiently, causing a lowering of the yield. Even if an amount greater than 3 by mol is added, the reaction does not change so much, causing only an economical disadvantage. Furthermore, a burden in a purification process unpreferably increases, because it is necessary to remove an excessive deacidifier. It is more preferably from 1 to 2 by mol.

The reaction temperature is not particularly limited, and it is usually appropriately from −20° C. to 200° C. A temperature lower than −20° C. is not preferable, because it is impossible to obtain a sufficient reaction rate. With this, the reaction time becomes very long, and thus it becomes impossible to efficiently conduct the reaction. A temperature higher than 200° C. is not preferable, because the decomposition becomes violent. This causes a lowering of the yield. Furthermore, a burden in a purification process unpreferably increases, because it is necessary to remove the degradation product. It is more preferably from 20° C. to 70° C.

It is also possible to produce an N-phenyltetrahydrophthalamic derivative [II] which is a compound of the present invention by reacting an imidoylchloride derivative represented by the general formula [IV] with an alkali metal salt of a carboxylic acid, represented by the general formula [VIII], as shown in the following formula.

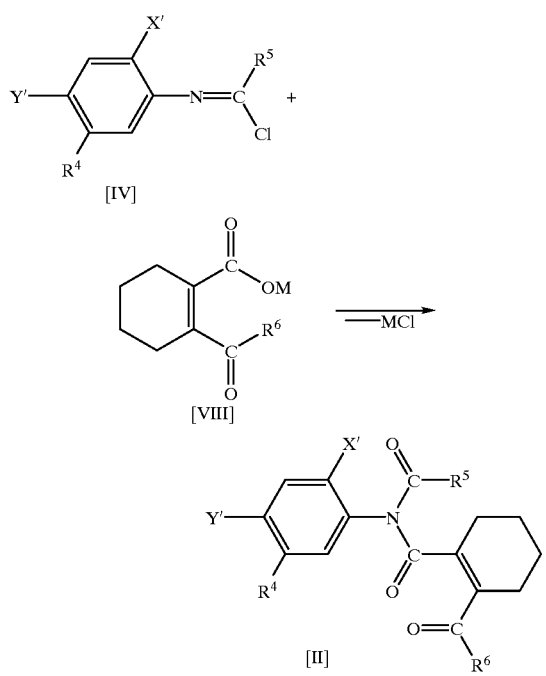

wherein X' and Y' each individually represent hydrogen atoms or halogen atoms, $R^4$ represents a hydrogen atom, a lower alkoxy group, a lower alkenyloxy group, a lower alkynyloxy group, cycloalkyloxy group, a lower alkoxycarbonyl group, a lower alkoxycarbonylalkoxy group or a lower alkoxycarbonylalkylthio group, $R^5$ represents:

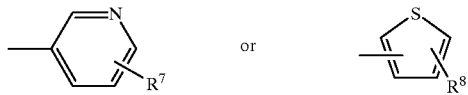

wherein $R^7$ represents a hydrogen atom, a halogen atom, a lower alkyl group or a lower alkoxycarbonyl group, and $R^8$ represents a hydrogen atom, a halogen atom or a lower alkyl group, and $R^6$ represents a lower alkoxy group, a lower alkenyloxy group, a lower alkynyloxy group, a cycloalkyloxy group or a lower alkoxyalkoxy group, and M represents an alkali metal.

The reaction can preferably be conducted without using any solvent, or in a suitable solvent such as benzene, toluene, xylene, methylene chloride, chloroform, ethyl acetate, dioxane, tetrahydrofuran, diethyl ether, N,N-dimethylformamide, dimethylsulfoxide or water, if necessary, by adding a phase transfer catalyst.

The present reaction is an equimolar reaction. Therefore, the molar ratio of an alkali metal salt of a carboxylic acid [VIII] to an imidoylchloride derivative [IV] is preferably about 1, and it is usually appropriately from 0.8 to 1.2. In case that it is less than 0.8 by mol, the imidoylchloride derivative [IV] which has been added in an excessive amount remains unreacted in a large amount. In case that it is greater than 1.2 by mol, the alkali metal salt of carboxylic acid [VIII] which has been added in an excessive amount remains unreacted in a large amount. Therefore, it becomes impossible to effectively conduct the reaction, thereby causing an economical disadvantage. Furthermore, a burden in a purification process unpreferably increases, because it is necessary to remove or recover the unreacted imidoylchloride derivative [IV] or unreacted alkali metal salt of carboxylic acid [VIII]. It is more preferably from 0.9 to 1.1 by mol.

As examples of a phase transfer catalyst used in the present reaction, it is possible to cite, for example, crown ethers such as 18-crown-6-ether, polyethers such as polyethylene glycol, quaternary phosphonium salts such as tetraphenylphosphonium chloride, and quaternary ammonium salts such as tetrabutylammonium bromide and tetrabutylammonium hydrogensulfate.

The amount of the phase transfer catalyst to be used is not particularly limited, and may arbitrarily be adjusted depending on the desired reaction rate. It is usually appropriately from 0.01 mol % to 20 mol % relative to the imidoylchloride derivative [IV]. Less than 0.01 mol % is not preferable, because it is impossible to obtain a sufficient reaction rate. With this, the reaction time becomes very long, and thus it becomes impossible to efficiently conduct the reaction. Even if an amount greater than 20 mol % is added, the reaction does not change so much, causing only an economical disadvantage. Thus, this is not preferable. It is more preferably from 0.1 mol % to 10 mol %.

The reaction temperature is not particularly limited, and it is usually appropriately from 0° C. to 200° C. A temperature lower than 0° C. is not preferable, because it is impossible to obtain a sufficient reaction rate. With this, the reaction time becomes very long, and thus it becomes impossible to efficiently conduct the reaction. A temperature higher than 200° C. is not preferable, because the decomposition becomes violent. This causes a lowering of yield. Furthermore, a burden in a purification process unpreferably increases, because it is necessary to remove the degradation product. It is preferably from 0° C. to 100° C. for more efficiently conducting the reaction.

Furthermore, an imidoylchloride derivative [I] which is necessary as a starting material to obtain an N-phenyltetrahydrophthalamic acid derivative of the present invention can be produced, for example, using an anilide derivative represented by the general formula [IX] as a starting raw material,

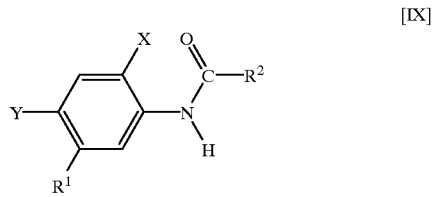

wherein X and Y each individually represent hydrogen atoms or halogen atoms, $R^1$ represents a lower alkoxycarbonylalkylthio group, and $R^2$ represents a lower alkyl group, a halogenated lower alkyl group or a substituted or unsubstituted phenyl group.

The reaction can be conducted in accordance with the following reaction formula, using a dehydrochlorinating agent, in the presence of a reaction solvent or not.

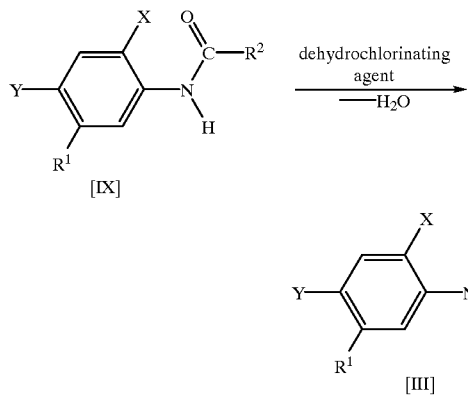

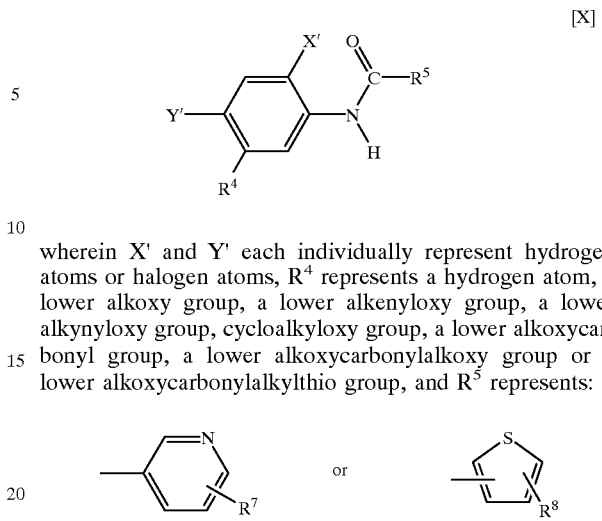

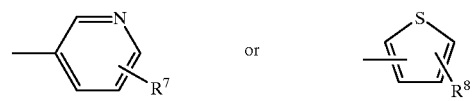

wherein X and Y each individually represent hydrogen atoms or halogen at oms, $R^1$ represents a lower alkoxycarbonylalkylthio group, and $R^2$ represents a lower alkyl group, a halogenated lower alkyl group or a substituted or unsubstituted phenyl group.

As preferable examples of the dehydrochlorinating agent used in the reaction, there can be cited phosphorus pentachloride, phosphorus trichforide-chaorine, thionyl chloride, arylsulfonylchl oride, phosgene, triphenylphosphine-carbon tetrachloride and polymer carried triphenylphosphine-carbon tetrachloride.

The amount of dehydrochiorinating agent to be used is appropriately from 1 equivalent to 10 equivalents relative to the anilide derivative [IX]. If it is less than 1 equivalent, the reaction does not proceed sufficiently, causing a lowering of the yield. Thus, this is not preferable. Even if an amount greater than 10 equivalents is added, the reaction does not change so much, thereby causing only an economical disadvantage. Furthermore, a burden in a purification process increases, because it is necessary to remove an excessive amount of the dehydrochiorinating agent. It is more preferably from 1 equivalent to 2 equivalents.

Furthermore, as preferable examples of the solvent used in the reaction, there can be cited halogenated hydrocarbons such as dichloroethane, carbon tetrachlo ride, chloroform and methylene chloride, aromatic hydrocarbons such as benzene, toluene, xylene and chlorobenzene, polar solvents such as acetonitrile and dimethyl sulfoxide.

The reaction temperature is not particularly limited, and is usually appropriately from 0° C. to 100° C. A temperature lower than 0° C. is not preferable, because it is impossible to obtain a sufficient reaction rate. With this, the reaction time becomes very long, and thus it becomes impossible to efficiently conduct the reaction. A temperature higher than 100° C. is not preferable, because the decomposition becomes violent. This causes a lowering of the yield. Furthermore, a burden in a purification process unpreferably increases, because it is necessary to remove the degradation product. It is more preferably from room temperature to 80° C.

Furthermore, an imidoylchloride derivative [IV] which is necessary as a starting material to obtain an N-phenyltetrahydrophthalamic acid derivative [IV] of the present invention can be produced, for example, using an anilide derivative represented by the general formula [X] as a starting raw material, wherein X' and Y' each individually represent hydrogen atoms or halogen atoms, $R^4$ represents a hydrogen atom, a lower alkoxy group, a lower alkenyloxy group, a lower alkynyloxy group, cycloalkyloxy group, a lower alkoxycarbonyl group, a lower alkoxycarbonylalkoxy group or a lower alkoxycarbonylalkylthio group, and $R^5$ represents:

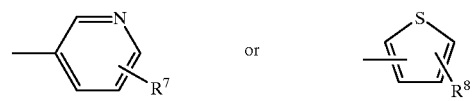

wherein $R^7$ represents a hydrogen atom, a halogen atom, a lower alkyl group or a lower alkoxycarbonyl group, and $R^8$ represents a hydrogen atom, a halogen atom or a lower alkyl group.

The reaction can be conducted in accordance with the following reaction formula, using a dehydrochlorinating agent, in the presence of a reaction solvent or not.

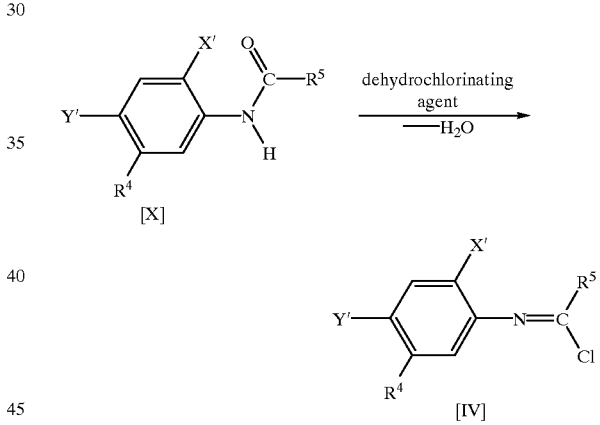

wherein X' and Y' each individually represent hydrogen atoms or halogen atoms, $R^4$ represents a hydrogen atom, a lower alkoxy group, a lower alkenyloxy group, a lower alkynyloxy group, cycloalkyloxy group, a lower alkoxycarbonyl group, a lower alkoxycarbonylalkoxy group or a lower alkoxycarbonylalkylthio group, and $R^5$ represents:

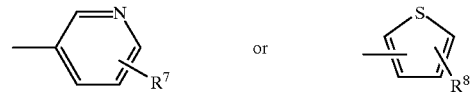

wherein $R^7$ represents a hydrogen atom, a halogen atom, a lower alkyl group or a lower alkoxycarbonyl group, and $R^8$ represents a hydrogen atom, a halogen atom or a lower alkyl group.

As preferable examples of the dehydrochlorinating agent used in the reaction, there can be cited phosphorus pentachloride, phosphorus trichloride-chlorine, thionyl chloride, arylsulfonyl-chloride, phosgene, triphenylphosphine-carbon tetrachloride and polymer carried triphenylphosphine-carbon tetrachloride.

The amount of dehydrochlorinating agent to be used is appropriately from 1 equivalent to 10 equivalents relative to the anilide derivative [X]. If it is less than 1 equivalent, the reaction does not proceed sufficiently, causing a lowering of the yield. Thus, this is not preferable. Even if an amount greater than 10 equivalents is added, the reaction does not change so much, thereby causing only an economical disadvantage. Furthermore, a burden in a purification process increases, because it is necessary to remove an excessive amount of the dehydrochlorinating agent. It is more preferably from 1 equivalent to 2 equivalents.

Furthermore, as preferable examples of the solvent used in the reaction, there can be cited halogenated hydrocarbons such as dichloroethane, carbon tetrachloride, chloroform and methylene chloride, aromatic hydrocarbons such as benzene, toluene, xylene and chlorobenzene, polar solvents such as acetonitrile and dimethyl sulfoxide.

The reaction temperature is not particularly limited, and is usually appropriately from 0° C. to 100° C. A temperature lower than 0° C. is not preferable, because it is impossible to obtain a sufficient reaction rate. With this, the reaction time becomes very long, and thus it becomes impossible to efficiently conduct the reaction. A temperature higher than 100° C. is not preferable, because the decomposition becomes violent. This causes a lowering of the yield. Furthermore, a burden in a purification process unpreferably increases, because it is necessary to remove the degradation product. It is more preferably from room temperature to 80° C.

THE BEST MODE TO CARRY OUT THE INVENTION

In the following, the present invention will be described concretely with reference to Examples.

REFERENTIAL EXAMPLE 1

Production of 5-acetylamino-2-chloro-4-fluoro-methoxycarbonylmethylthiophenol (A compound that is represented by No. 1 in the aftermentioned Table 1 and by the general formula [IX]

3.75 g (27.1 mmol) of potassium carbonate was suspended in 50 ml of N,N-dimethylformamide (DMF). Then, 11.9 g (54.2 mmol) of 5-acetylamino-2-chloro-4-fluoro-thiophenol was dissolved in 80 ml of DMF, and then it was added thereto. Under stirring, 8.29 g (54.2 mmol) of methyl bromoacetate was dissolved in 20 ml of DMF, and it was added dropwise thereto at room temperature. After the reaction for 10 minutes, DMF was removed under reduced pressure, and then water was added to the residue, followed by an extraction with ethyl acetate. It was washed first with water and then with saturated brine and then dried with anhydrous magnesium sulfate. Then, the solvent was distilled off under reduced pressure, thereby to obtain crystals. Recrystallization was conducted with ethyl acetate/n-hexane, thereby to obtain 12.49 g of 5-acetyl-2-chloro-4-fluoromethoxycarbonylmethylthiophenol. The melting point was 125.0–126.5° C.

Table 1 shows the anilide derivatives [IX] which were obtained in manners analogous to that of the above Referential Example 1, and Table 2 shows 1H-NMR absorption spectrum values thereof.

TABLE 1

[IX-A]

| Compound No. | R¹ | R² | m.p. (° C.) |
|---|---|---|---|
| 1 | SCH$_2$COOCH$_3$ | CH$_3$ | 125.0~126.5 |
| 2 | SCH$_2$COOCH$_3$ | CH$_2$CH$_3$ | 104.5~105 |
| 3 | SCH$_2$COOCH$_3$ | phenyl | 93.5~96.0 |
| 4 | SCH$_2$COOCH$_3$ | 3-fluorophenyl | 115.5~116 |
| 5 | SCHCOOCH$_3$<br>\|<br>CH$_3$ | CH$_3$ | 80.5~81.0 |
| 24 | SCH$_2$COOCH$_2$CH$_3$ | CH$_3$ | 94.0~96.5 |
| 25 | SCH$_2$COOCH$_2$CH$_3$ | CH$_2$CH$_3$ | 74.0~75.0 |
| 26 | SCH$_2$COO$^n$Bu | CH$_3$ | 80.5~82.0 |

TABLE 2

| Compound No. | $^1$H-NMR Absorption Spectrum Values (δ) (CDCl$_3$) |
|---|---|
| 1 | 2.10(s, 3H), 3.34(s, 1H), 3.65(s, 3H), 3.89(s, 2H), 7.56 (d, J=7.55Hz, 1H), 8.02(d, J=8.1Hz, 1H) |
| 2 | 1.24(t, J=7.4Hz, 3H), 2.44(q, J=7.4Hz, 2H), 3.68(s, 2H), 3.75(s, 3H), 7.16(d, J=10.3Hz, 1H), 7.32~7.56(brs, 1H), 8.53(d, J=8.1Hz, 1H) |
| 3 | 3.70(s, 2H), 3.73(s, 3H), 7.16~8.00(m, 8H) |
| 4 | 3.72(s, 2H), 3.77(s, 3H), 7.22(d, J=10.5Hz, 1H), 7.20~7.76(m, 4H), 7.89~8.16(brs, 1H), 8.60(d, J=8.1Hz, 1H) |
| 5 | 1.26(d, J=7.0Hz, 3H), 2.22(s, 3H), 3.71(s, 3H), 3.85(q, J=7.25Hz, 1H), 7.26(d, J=11.55Hz, 1H), 7.20~7.44(brs, 1H), 8.57(d, J=8.0Hz, 1H) |
| 24 | 1.25(t, J=7.25Hz, 3H), 2.21(s, 3H), 3.67(s, 2H), 4.19(q, J=7.25Hz, 2H), 7.15(d, J=10.5Hz, 1H), 7.4(bs, 1H), 8.55 (d, J=8.1Hz, 1H) |
| 25 | 1.24(t, J=7.25Hz, 3H), 1.26(t, J=7.25Hz, 3H), 2.44(q, J= 7.25Hz, 2H), 3.68(s, 2H), 4.19(q, J=7.25Hz, 2H), 7.15(d, J=10.55Hz, 1H), 7.38(brs, 1H), 8.55(d, J=8.1Hz, 1H) |
| 26 | 0.90(t, J=6.6Hz, 3H), 1.19~1.6(m, 4H), 2.2(s, 3H), 3.67 (s, 3H), 4.12(t, J=6.49Hz, 2H), 7.15(d, J=10.3Hz, 1H), 7.21~7.44(bs, 1H), 8.49(d, J=8.13Hz, 1H) |

EXAMPLE 1

Production of N-(4-chloro-2-fluoro-5-methoxycarbonylmethylthiophenyl)-acetoimidoylchloride (A compound that is represented by No. 6 in the aftermentioned Table 3 and by the general formula [III])

10 g (34.3 mmol) of 5-acetylamino-2-chloro-4-fluoromethoxycarbonylmethylthiophenol and 7.14 g (34.3 mmol) of phosphorus pentachloride were suspended in 250 ml of benzene, followed by heating to 60° C. and then by stirring for 1 hr. After the reaction, the reaction liquid was concentrated under reduced pressure, thereby to quantitatively obtain N-(4-chloro-2-fluoro5-methoxycarbonylmethylthiophenyl)-acetoimidoylchloride in the form of oil-like substance.

EXAMPLE 2

Production of N-acetyl-N-(4-chloro-2-fluoro-5-methoxycarbonylmethylthiophenyl)-3,4,5,6-tetrahydrophthalamic acid methyl ester (A compound that is represented by No. 11 in the aftermentioned Table 5 and by the general formula [I])

10.6 g (34.3 mmol) of N-(4-chloro-2-fluoro-5-methoxycarbonylmethylthiophenyl)-acetoimidoylchloride and 6.95 g (37.7 mmol) of 3,4,5,6-tetrahydrophthalamic acid monomethyl ester were dissolved in 50 ml of benzene. Then, 4.16 g (41.2 mmol) of trimethylamine dissolved in 10 ml of benzene was added dropwise thereto at a temperature not higher than 10° C. After the dropwise addition, stirring was conducted at 60° C. for 3 hr. After it was allowed to stand to cool down, it was washed first with water and then with saturated brine and then dried with anhydrous magnesium sulfate. The solvent was concentrated, thereby to obtain crystals. Recrystallization was conducted with methanol, thereby to obtain 5.09 g of N-acetyl-N-(4-chloro-2-fluoro-5-methoxycarbonylmethylthiophenyl)-3,4,5,6-tetrahydrophthalamic acid methyl ester. The melting point was 124.0–124.5° C.

EXAMPLE 3

Production of N-acetyl-N-[4-chloro-2-fluoro-5-(1-methoxycarbonylethylthio)phenyl]-3,4,5,6-tetrahydrophthalamic acid methyl ester (A compound that is represented by No. 20 in the aftermentioned Table 5 and by the general formula [I])

1.0 g (3.1 mmol) of N-[4-chloro-2-fluoro-5-(1-methoxycarbonylethylthio)phenyl]-acetoimidoylchloride and 0.83 g (3.7 mmol) of a potassium salt of 3,4,5,6-tetrahydrophthalamic acid monomethyl ester were mixed in 20 ml of N,N-dimethylformamide, followed by heating and stirring at 70° C. for 2 hr. After it was allowed to stand to cool down, the solvent was distilled off under reduced pressure, then water was added to the residue, and then it was extracted with ethyl acetate. The organic layer was washed with water, followed by drying with anhydrous magnesium sulfate. The solvent was concentrated, thereby to obtain an oil-like substance. The residue was purified by silica gel column chromatography, thereby to obtain 0.66 g of N-acetyl-N-[4-chloro-2-fluoro-5-(1-methoxycarbonylethylthio)phenyl]-3,4,5,6-tetrahydrophthalamic acid methyl ester in the form of oil-like substance.

Table 5 shows N-phenyltetrahydrophthalamic acid derivatives [I]) which are compounds of the present invention and were obtained in manners analogous to those of the foregoing Examples 1–3, and Table 6 shows $^1$H-NMR absorption spectrum values thereof. Table 3 shows imidoylchloride derivatives [III] which are compounds of the present invention, and Table 4 shows $^1$H-NMR absorption spectrum values thereof. However, the compounds of the present invention are not limited to these.

The compound Nos. will be employed in the following examples and experiments, too.

TABLE 3

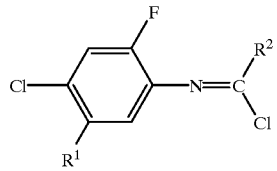

[III-A]

| Compound No. | R$^1$ | R$^2$ |
|---|---|---|
| 6 | SCH$_2$COOCH$_3$ | CH$_3$ |
| 7 | SCH$_2$COOCH$_3$ | CH$_2$CH$_3$ |
| 8 | SCH$_2$COOCH$_3$ | —C$_6$H$_5$ |
| 9 | SCH$_2$COOCH$_3$ | —C$_6$H$_4$F |
| 10 | SCH(CH$_3$)COOCH$_3$ | CH$_3$ |
| 27 | SCH$_2$COOCH$_2$CH$_3$ | CH$_3$ |
| 28 | SCH$_2$COOCH$_2$CH$_3$ | CH$_2$CH$_3$ |
| 29 | SCH$_2$COO$^n$Bu | CH$_3$ |

TABLE 4

| Compound No. | $^1$H-NMR Absorption Spectrum Values (δ) (CDCl$_3$) |
|---|---|
| 6 | 2.59(s, 3H), 3.63(s, 2H), 3.68(s, 3H), 7.03(d, J=7.9Hz, 1H), 7.21(d, J=9.7Hz, 1H) |
| 7 | 1.32(t, J=7.25Hz, 3H), 2.83(q, J=7.25Hz, 2H), 3.65(s, 2H), 3.69(s, 3H), 7.03(d, J=7.9Hz, 1H), 7.21(d, J=9.65Hz, 1H) |
| 8 | 3.67(s, 2H), 3.72(s, 3H), 7.13~8.24(m, 7H) |
| 9 | 3.64(s, 2H), 3.69(s, 3H), 7.15(d, J=6.6Hz, 1H), 7.25(d, J=8.35Hz, 1H), 7.22~7.99(m, 4H) |
| 10 | 1.51(d, J=7.0Hz, 3H), 2.62(s, 3H), 3.65(s, 3H), 3.86(q, J=7.0Hz, 1H), 7.15(d, J=8.1Hz, 1H), 7.24(d, J=9.7Hz, 1H) |
| 27 | 1.22(t, J=7.0Hz, 3H), 2.61(s, 3H), 3.62(s, 2H), 4.15(q, J=7.0Hz, 2H), 7.04(d, J=7.7Hz, 1H), 9.45(d, J=9.5Hz, 1H) |
| 28 | 1.25(t, J=7.25Hz, 3H), 1.32(t, J=7.25Hz, 3H), 2.84(q, J=7.25Hz, 2H), 3.65(s, 2H), 4.15(q, J=7.25Hz, 2H), 7.03(d, J=7.9Hz, 1H), 7.3(d, J=9.7Hz, 1H) |
| 29 | 0.90(t, J=6.38Hz, 3H), 1.12~1.65(m, 4H), 2.60(s, 3H), 3.63(s, 2H), 4.09(t, J=6.38Hz, 2H), 7.03(d, J=7.91Hz, 1H), 7.21(d, J=9.67Hz, 1H) |

TABLE 5

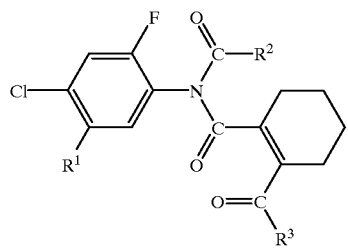

[I-A]

| Compound No. | R¹ | R² | R³ | m.p. (°C) |
|---|---|---|---|---|
| 11 | SCH₂COOCH₃ | CH₃ | OCH₃ | 124.0~124.5 |
| 12 | SCH₂COOCH₃ | CH₃ | OCH₂CH₃ | glassy |
| 13 | SCH₂COOCH₃ | CH₃ | O(CH₂)₂CH₃ | 59.5~60.0 |
| 14 | SCH₂COOCH₃ | CH₃ | O(CH₂)₂CH₃ | 49.5~50.5 |
| 15 | SCH₂COOCH₃ | CH₃ | OCH₂C≡CH | oil-like substance |
| 16 | SCH₂COOCH₃ | CH₂CH₃ | OCH₃ | 95.5~96.0 |
| 17 | SCH₂COOCH₃ | CH₂CH₃ | O(CH₂)₄CH₃ | oil-like substance |
| 18 | SCH₂COOCH₃ | ⌬ (phenyl) | OCH₃ | 159.5~162.5 |
| 19 | SCH₂COOCH₃ | 3-F-phenyl | OCH₃ | 150.5~151.0 |
| 20 | SCHCOOCH₃ \| CH₃ | CH₃ | OCH₃ | oil-like substance |
| 21 | SCHCOOCH₃ \| CH₃ | CH₃ | OCH₂CH₃ | oil-like substance |
| 22 | SCHCOOCH₃ \| CH₃ | CH₃ | O(CH₂)₂CH₃ | oil-like substance |
| 23 | SCHCOOCH₃ \| CH₃ | CH₃ | O(CH₂)₂OCH₂CH₃ | oil-like substance |
| 30 | SCH₂COOCH₃ | CH₃ | OCH(CH₃)₂ | oil-like substance |
| 31 | SCH₂COOCH₃ | CH₃ | O(CH₂)₂OCH₃ | 93.5~94.5 |
| 32 | SCH₂COOCH₃ | CH₃ | O(CH₂)₂OCH₂CH₃ | 80.0~81.5 |
| 33 | SCH₂COOCH₃ | CH₂CH₃ | OCH₂CH₃ | 57.5~59.0 |
| 34 | SCH₂COOCH₃ | CH₂CH₃ | O(CH₂)₂CH₃ | 62.0~63.0 |
| 35 | SCH₂COOCH₃ | CH₂CH₃ | O(CH₂)₃CH₃ | 56.0~57.0 |
| 36 | SCH₂COOCH₃ | CH₂CH₃ | O(CH₂)₂OCH₃ | 79.0~80.0 |
| 37 | SCH₂COOCH₃ | CH₂CH₃ | O(CH₂)₂OCH₂CH₃ | 63.0~65.0 |
| 38 | SCH₂COOCH₃ | CH₂CH₃ | OCH₂C≡CH | oil-like substance |
| 39 | SCH₂COOCH₂CH₃ | CH₃ | O(CH₂)₃CH₃ | oil-like substance |
| 40 | SCH₂COOⁿBu | CH₃ | O(CH₂)₃CH₃ | oil-like substance |
| 41 | SCHCOOCH₃ \| CH₃ | CH₃ | OCH(CH₃)₂ | 79.0~80.0 |

TABLE 5-continued

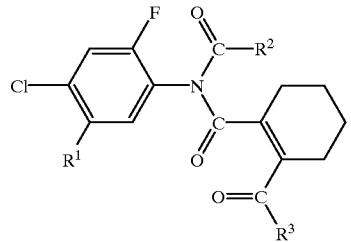

[I-A]

| Compound No. | R¹ | R² | R³ | m.p. (° C.) |
|---|---|---|---|---|
| 42 | SCHCOOCH₃<br>\|<br>CH₃ | CH₃ | O(CH₂)₃CH₃ | oil-like substance |
| 43 | SCHCOOCH₃<br>\|<br>CH₃ | CH₃ | P(CH₂)₄CH₃ | oil-like substance |
| 44 | SCHCOOCH₃<br>\|<br>CH₃ | CH₃ | O(CH₂)₂OCH₃ | oil-like substance |

TABLE 6

| Compound No. | ¹H-NMR Absorption Spectrum Values (δ) (CDCl₃) |
|---|---|
| 11 | 1.47~2.77(m, 4H), 2.10~2.42(m, 4H), 2.19(m, 3H), 3.65 (s, 2H), 3.69(s, 3H), 3.74(s, 3H), 7.32(d, J=8.8Hz, 1H), 7.64(d, J=7.7Hz, 1H) |
| 12 | 1.29(t, J=7.0Hz, 3H), 1.40~1.80(m, 4H), 2.20(s, 3H), 2.00~ 2.40(m, 4H), 3.66(s, 2H), 3.69(s, 3H), 4.21(q, J=7.0Hz, 2H), 7.32(d, J=9.0Hz, 1H), 7.70(d, J=7.5Hz, 1H) |
| 13 | 0.96(t, J=7.35Hz, 3H), 1.24~1.85(m, 6H), 2.09~2.45(m, 4H), 2.09(s, 3H), 3.66(s, 2H), 3.69(s, 3H), 4.11(t, J= 6.6Hz, 2H), 7.31(d, J=9.0Hz, 1H), 7.66(d, J=7.45Hz, 1H) |
| 14 | 0.81~1.06(m, 3H), 1.40~1.76(m, 8H), 2.10~2.44(m, 4H), 2.19(s, 3H), 3.65(s, 2H), 3.69(s, 3H), 4.16(t, J=7.1Hz, 2H), 7.31(d, J=8.8Hz 1H), 7.66(d, J=7.7Hz 1H) |
| 15 | 1.52~1.82(m, 4H), 2.03(s, 3H), 2.23~2.48(m, 4H), 2.56 (t, J=2.4Hz, 1H), 3.09(s, 3H), 4.76(s, 2H), 4.79(s, 2H), 7.34(d, J=9.0Hz, 1H), 7.66(d, J=7.7Hz, 1H) |
| 16 | 1.06(t, J=7.1Hz, 3H), 1.48~1.84(m, 4H), 2.04~2.56(m, 6H), 3.67(s, 2H), 3.69(s, 3H), 3.74(s, 2H), 7.32(d, J= 8.7Hz, 1H), 7.64(d, J=7.7Hz, 1H) |
| 17 | 0.72~1.00(m, 3H), 1.17(t, J=7.0Hz, 3H), 1.20~1.48(m, 4H), 1.40~1.84(m, 6H), 2.17~2.54(m, 6H), 3.67(s, 2H), 3.69(s, 3H), 4.06~4.21(m, 2H), 7.31(d, J=8.0Hz, 1H), 7.67(d, J=7.7Hz, 1H) |
| 18 | 1.41~1.77(m, 4H), 2.18~2.40(m, 2H), 2.40~2.64(m, 2H), 3.67(s, 2H), 3.74(s, 3H), 3.75(s, 3H), 7.04(d, J=9.2Hz, 1H), 7.20~7.56(m, 5H), 7.90(d, J=7.5Hz, 1H) |
| 19 | 1.49~1.85(m, 4H), 2.15~2.39(m, 2H), 2.39~2.64(m, 2H), 3.67(s, 2H), 3.75(s, 1H), 3.76(s, 1H), 6.91~7.37(m, 4H), 7.07(d, J=9.45Hz, 1H), 7.90(d, J=7.45Hz, 1H) |
| 20 | 1.50(d, J=7.25Hz, 3H), 1.57~1.80(m, 4H), 2.21(s, 3H), 2.24~2.45(m, 4H), 3.37(s, 3H), 3.65(s, 3H), 3.85(q, J= 7.0Hz, 1H), 7.33(d, J=9.0Hz, 1H), 7.76(d, J=7.7Hz, 1H) |
| 21 | 1.28(t, J=7.25Hz, 3H), 1.51(d, J=7.25Hz, 3H), 1.56~1.76 (m, 4H), 2.21(s, 3H), 2.20~2.44(m, 4H), 3.65(s, 3H), 3.85(q, J=7.25Hz, 1H), 4.20(q, J=7.25Hz, 2H), 7.34(d, J= 9.0Hz, 1H), 7.73(d, J=7.9Hz, 1H) |
| 22 | 0.95(t, J=7.2Hz, 3H), 1.50(d, J=7.0Hz, 3H), 1.55~1.85 (m, 6H), 2.18~2.45(m, 4H), 3.65(s, 3H), 3.85(q, J=7.1Hz, 1H), 4.1(t, J=6.6Hz, 2H), 7.35(d, J=9.0Hz, 1H), 7.74(d, J=7.9Hz, 1H) |
| 23 | 1.19(t, J=7.0Hz, 3H), 1.50(d, J=7.0Hz, 3H), 1.58~1.80 (m, 4H), 3.52(q, J=6.8Hz, 2H), 3.65(s, 3H), 3.65(t, J= 4.8Hz, 2H), 3.86(q, J=7.25Hz, 1H), 4.24~4.34(m, 2H), 7.34 (d, J=9.0Hz, 1H), 7.77(d, J=7.7Hz, 1H) |
| 30 | 1.27(d, J=6.4Hz, 6H), 1.40~1.88(m, 4H), 2.00~2.44(m, 4H), 2.22(s, 3H), 3.66(s, 2H), 3.69(s, 3H), 5.07(7th, J= 6.4Hz, 1H), 7.31(d, J=9.0Hz, 1H), 7.78(d, J=7.7Hz, 1H) |
| 31 | 1.19(t, J=7.0Hz, 3H), 1.45~1.75(m, 4H), 2.21(s, 3H), 2.1~ 2.5(m, 4H), 3.52(q, J=7.0Hz, 2H), 3.55~3.7(m, 2H), 3.67(s, 2H), 3.69(s, 3H), 4.2~4.35(m, 2H), 7.3(d, J= 9.22Hz, 1H), 7.69(d, J=7.7Hz, 1H) |
| 32 | 1.19(t, J=6.9Hz, 3H), 1.40~1.76(m, 4H), 2.06~2.46(m, 4H), 2.21(s, 3H), 3.58(q, J=6.9Hz, 2H), 3.60~3.71(m, 2H), 3.67(s, 2H), 3.69(s, 3H), 4.24~4.35(m, 2H), 7.30(d, J=9.2Hz, 1H), 7.67(d, J=7.7Hz, 1H) |
| 33 | 1.08(t, J=7.2Hz, 3H), 1.28(t, J=7.1Hz 3H), 1.30~1.70 (m, 4H), 2.12~2.44(m, 6H), 3.68(s, 2H), 3.70(s, 3H), 4.21 (q, J=7.1Hz, 2H), 7.67(d, J=7.5Hz, 1H) |
| 34 | 0.95(t, J=7.3Hz, 3H), 1.07(t, J=7.1Hz, 3H), 1.56~1.79 (m, 6H), 2.12~2.56(m, 6H), 3.67(s, 2H), 3.68(s, 3H), 4.10 (t, J=6.6Hz, 2H), 7.31(d, J=9.0Hz, 1H), 7.66(d, J=7.5Hz, 1H) |
| 35 | 0.94(t, J=6.4Hz, 3H), 1.07(t, J=7.3Hz, 3H), 1.23~1.88 (m, 8H), 2.12~2.54(m, 6H), 3.67(s, 2H), 3.68(s, 3H), 4.14 (t, J=6.3Hz, 1H), 7.31(d, J=8.8Hz, 1H), 7.67(d, J=7.5Hz, 1H) |
| 36 | 1.07(t, J=7.0Hz, 3H), 1.40~1.80(m, 4H), 2.08~2.48(m, 6H), 3.36(s, 3H), 3.55~3.79(m, 2H), 3.68(s, 2H), 3.69 (s, 3H), 4.24~4.35(m, 2H), 7.30(d, J=9.0Hz, 1H), 7.68(d, J=7.69Hz, 1H) |
| 37 | 1.07(t, J=7.25Hz, 3H), 1.19(t, J=7.0Hz, 3H), 1.48~1.76 (m, 4H), 2.08~2.56(m, 6H), 3.52(q, J=7.0Hz, 2H), 3.59~ 3.68(m, 7H), 4.23~4.34(m, 2H), 7.30(d, J=8.8Hz, 1H), 7.69(d, J=7.7Hz, 1H) |
| 38 | 1.07(t, J=7.25Hz, 3H), 1.46~1.88(m, 4H), 2.23~2.38(m, |

TABLE 6-continued

| Compound No. | $^1$H-NMR Absorption Spectrum Values (δ) (CDCl$_3$) |
|---|---|
|  | 6H), 2.49(t, J=2.4Hz, 1H), 3.68(s, 2H), 3.70(s, 3H), 4.76 (d, J=2.4Hz, 2H), 7.32(d, J=9.0Hz, 1H), 7.67(d, J=7.7Hz, 1H) |
| 39 | 0.93(t, J=6.4Hz, 3H), 1.23(t, J=7.1Hz, 3H), 1.44~1.80 (m, 8H) 2.20(s, 3H), 2.12~2.52(m, 4H), 3.64(s, 2H), 4.14 (t, J=6.4Hz, 2H), 4.15(q, J=7.1Hz, 2H), 7.30(d, J=9.0Hz, 1H), 7.65(d, J=7.7Hz, 1H) |
| 40 | 0.75~1.04(m, 6H), 1.10~1.85(m, 12H), 2.19(s, 3H), 2.12~2.46(m, 4H), 3.64(s, 2H), 4.09(t, J=6.6Hz 2H), 4.13 (t, J=6.4Hz, 2H), 7.28(d, J=8.8Hz, 1H), 7.63(d, J=7.7Hz, 1H) |
| 41 | 1.26(d, J=6.4Hz, 6H), 1.57(d, J=7.0Hz, 3H), 1.46~1.76 (m, 4H), 2.23(s, 3H), 2.10~2.40(m, 4H), 3.64(s, 3H), 3.84 (q, J=7.0Hz, 1H), 5.06(7th, J=6.4Hz, 1H), 7.33(d, J=9.0Hz, 1H), 7.75(d, J=7.7Hz, 1H) |
| 42 | 0.90(t, J=6.0Hz, 3H), 1.15~1.5(m, 4H), 1.5(d, J=7.0Hz, 3H), 1.4~1.8(m, 4H), 2.05~2.45(m, 4H), 2.19(s, 3H), 3.65(s, 3H), 3.84(q, J=7.0Hz, 1H), 4.12(t, J=6.0Hz, 2H), 7.33(d, J=9.0Hz, 1H), 7.73(d, J=7.9Hz, 1H) |
| 43 | 0.65~1.0(m, 3H), 1.0~1.4(m, 6H), 1.50(d, J=7.0Hz, 3H), 1.43~1.84(m, 4H), 2.19(s, 3H), 2.04~2.44(m, 4H), 3.65 (s, 3H), 3.84(q, J=7.0Hz, 1H), 4.12(t, J=6.5Hz, 2H), 7.33(d, J=9.0Hz, 1H), 7.73(d, J=7.9Hz, 1H) |
| 44 | 1.4~1.8(m, 4H), 1.51(d, J=7.0Hz, 3H), 2.21(s, 3H), 2.1~2.5(m, 4H), 3.37(s, 3H), 3.5~3.7(m, 4H), 3.65(s, 3H), 3.86(q, J=7.0Hz, 1H), 4.2~4.4(m, 2H), 7.34(d, J=9.0Hz, 1H), 7.76(d, J=7.7Hz, 1H) |

REFERENTIAL EXAMPLE 2

Production of N-[4-chloro-2-fluoro-5-(1-methylpropargyloxy)phenyl]nicotinamide (A compound that is represented by No. 46 in the aftermentioned Table 7 and by the general formula [X])

2.5 g (11.8 mmol) of 4-chloro-2-fluoro-5-(1-methylpropargyloxy)aniline and 2.53 g (25 mmol) of triethylamine were dissolved in 50 ml of 1,2-dichloroethane. 2.14 g (12 mmol) of chloronicotinoyl hydrochloride was added by small portions to this solution, while the reaction temperature was maintained at a temperature not higher than 35° C. Under room temperature, stirring was conducted for 2 hr. After the reaction, water was added to the reaction liquid, followed by extraction with ethyl acetate. Then, the organic layer was washed with water and then dried with anhydrous magnesium sulfate and then concentrated under reduced pressure. The obtained residue was recrystallized with a solvent mixture of n-hexane and ethyl acetate, thereby to obtain 2.5 g of pale yellow crystals, N-[4-chloro-2-fluoro-5-(1hylpropargyloxy)phenyl]nicotinamide. The melting point was 157–158° C.

Table 7 shows anilide derivatives [X] which were obtained in manners analogous to that of the foregoing Referential Example 2 and Table 8 shows $^1$H-NMR absorption spectrum values thereof.

TABLE 7

[X-A]

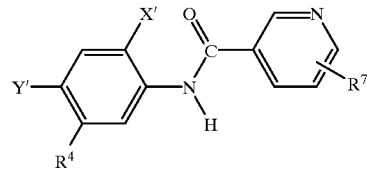

| Compound No. | X' | Y' | R$^4$ | R$^7$ | m.p. (° C.) |
|---|---|---|---|---|---|
| 45 | F | Cl | OCH(CH$_3$)$_2$ | H | 121~122 |
| 46 | F | Cl | OCHC≡CH\|CH$_3$ | H | 157~158 |
| 47 | F | Cl | OCHC≡CH\|CH$_3$ | 6-Cl | 159.5~160.0 |
| 48 | F | Cl | SCH$_2$COOCH$_3$ | H | 136~137 |
| 49 | Cl | Cl | OCHC≡CH\|CH$_3$ | H | 153~155 |
| 72 | F | Cl | SCHCOOCH$_3$\|CH$_3$ | H | — |

TABLE 8

| Compound No. | $^1$H-NMR Absorption Spectrum Values (δ) (CDCl$_3$) |
|---|---|
| 45 | 1.39(d, J=5.9Hz, 6H), 4.56(sev, J=5.9Hz, 1H), 1.17(d, J=10.3Hz, 1H), 7.44(dd, J=7.9, 4.8Hz, 1H), 8.15(d, J=7.0Hz, 1H), 8.09~8.5(m, 2H), 8.76(brd, J=4.8Hz, 1H), 9.09 (brs, 1H) |
| 46 | 1.72(d, J=6.6Hz 3H), 2.56(d, J=2.0Hz, 1H), 4.94(dq, J=6.6, 2.0Hz, 1H), 7.21(d, J=10.3Hz, 1H), 7.46(dd, J=7.3, 4.3Hz 1H), 8.09~8.33(m, 2H), 8.42(d, J=7.5Hz 1H), 8.79 (dd, J=4.3, 1.8Hz, 1H), 9.12(brd, J=1.8Hz, 1H) |
| 47 | 1.72(d, J=6.6Hz, 3H), 2.56(d, J=2.3Hz, 1H), 4.91(dq, J=6.6, 2.3Hz, 1H), 7.20(d, J=10.3Hz, 1H), 7.47(d, J=8.4Hz, 1), 8.08(brs, 1H), 8.15(dd, J=8.4, 2.7Hz, 1H), 8.35(d, J=7.3Hz, 1H), 8.88(d, J=2.7Hz, 1H) |
| 48 | 3.72(s, 3H), 3.77(s, 3H), 7.24(d, J=10.3Hz, 1H), 7.68(dd, J=8.0, 5.0Hz, 1H), 8.03~8.39(m, 1H), 8.60(d, J=8.0Hz, 1H), 8.81(dd, J=5.0, 2.8Hz, 1H), 9.11(brd, J=2.0Hz, 1H) |
| 49 | 1.71(d, J=6.0Hz, 3H), 3.15(d, J=2.0Hz, 1H), 5.11(dd, J=7.1, 2.8Hz, 1H), 7.57(s, 1H), 7.57(ddd, J=21.3, 5.6, 1.4Hz, 1H), 8.18(s, 1H), 8.34(dt, J=8.4, 1.4Hz, 1H), 8.78(dd, J=5.3, 1.4Hz, 1H) |
| 72 | 1.54(d, J=7.3Hz, 3H), 3.72(s, 3H), 3.97(q, J=7.3Hz, 1H), 7.26(d, J=10.3Hz, 1H), 7.44(dd, J=7.9, 4.6Hz, 1H), 8.21 (dt, J=7.9, 1.8Hz, 1H), 8.28(brs, 1H), 8.61(d, J=8.1Hz, 1H), 8.78(brd, J=4.6Hz, 1H), 9.10(brs, 1H) |

EXAMPLE 4

Production of N-[4-chloro-2-fluoro-5-(1-methylpropargyloxy)phenyl] nicotinoylimidoylchloride (A compound that is represented by No. 51 in the aftermentioned Table 9 and by the general formula [IV])

5.00 g (15.7 mmol) of N-[4-chloro-2-fluoro-5-(1-methylpropargyloxy)phenyl]nicotinamide was added to 30 ml of benzene, and then 3.27 g (15.7 mmol) of phosphorus pentachloride was added thereto under stirring. This mixture was heated and stirred at 60° C. for 2 hr. After standing to cool down, the solvent and the like were distilled off under reduced pressure. 20 ml of methylene chloride was added to the residue. Under cooling with ice, 1.60 g (15.8 mmol) of triethylamine was added dropwise thereto. After that, 10 ml of n-hexane was added thereto. After removal of the resulting precipitate by vacuum filtration, the filtrate was concentrated under reduced pressure. The residue was purified by silica gel column chromatography, thereby to obtain 2.87 g of N-[4-chloro-2-fluoro-5-(1-methylpropargyloxy)phenyl] nicotinoylimidoylchloride in the form of yellow crystals.

EXAMPLE 5

Production of N-[4-chloro-2-fluoro-5-(1-methylpropargyloxy)phenyl]-N-nicotinyl-3,4,5,6-tetrahydrophthalamic acid methyl ester (A compound represented by No. 57 in the aftermentioned Table 11 and by the general formula [II]

2.75 g (8.2 mmol) of N-(4-chloro-2-fluoro-5-(1-methylpropargyloxy)phenyl]nicotinoylimidoylchloride and 1.81 g (8.2 mmol) of a potassium salt of 3,4,5,6-tetrahydrophthalamic acid monomethyl ester were mixed in 20 ml of N,N-dimethylformamide, followed by heating and stirring at 70° C. for 2 hr. After standing to cool down, the solvent was distilled off under reduced pressure, then water was added to the residue, and then it was extracted with ethyl acetate. The organic layer was washed with water and then dried with anhydrous magnesium sulfate and then concentrated. The residue was recrystallized from methanol, thereby to obtain 2.35 g of N-[4-chloro-2-fluoro5-(1-methylpropargyloxy)phenyl]-N-nicotinyl-3,4,5,6-tetrehydrophthalamic acid methyl ester in the form of pale yellow crystals. The melting point was 115–118° C.

Table 11 shows N-phenyltetrahydrophthalamic acid derivatives [II] which are compounds of the present invention and were obtained in manners analogous to that of the foregoing Examples 4–5, and Table 12 shows $^1$H-NMR absorption spectrum values thereof. Table 9 shows imidoylchloride derivatives [IV] which are compounds of the present invention, and Table 10 shows $^1$H-NMR absorption spectrum values thereof. However, the compounds of the present invention are not limited to these.

The compound Nos. will be employed in the following examples and experiments, too.

TABLE 9

[IV-A]

| Compound No. | X' | Y' | R⁴ | R⁷ |
|---|---|---|---|---|
| 50 | F | Cl | OCH(CH₃)₂ | H |
| 51 | F | Cl | OCHC≡CH<br>\|<br>CH₃ | H |

TABLE 9-continued

[IV-A]

| Compound No. | X' | Y' | R⁴ | R⁷ |
|---|---|---|---|---|
| 52 | F | Cl | OCHC≡CH<br>\|<br>CH₃ | 5-COOCH₃ |
| 53 | F | Cl | OCHC≡CH<br>\|<br>CH₃ | 6-Cl |
| 54 | F | Cl | SCH₂COOCH₃ | H |
| 55 | Cl | Cl | OCHC≡CH<br>\|<br>CH₃ | H |
| 73 | F | Cl | SCHCOOCH₃<br>\|<br>CH₃ | H |

TABLE 10

| Compound No. | $^1$H-NMR Absorption Spectrum Values (δ) (CDCl₃) |
|---|---|
| 50 | 1.39(d, J=6.1Hz, 6H), 4.48(sev, J=6.1Hz, 1H), 6.65(d, J=7.1Hz, 1H), 7.22(d, J=9.4Hz, 1H), 7.44(dd, J=6.4, 4.8Hz, 1H), 8.39(dt, J=6.4, 1.6Hz, 1H), 8.78(dd, J=4.8, 1.6Hz, 1H) |
| 51 | 1.73(d, J=6.6Hz, 3H), 2.55(d, J=2.2Hz, 1H), 4.84(dq, J=6.6, 2.2Hz, 1H), 6.90(d, J=7.0Hz, 1H), 7.24(d, J=9.5Hz, 1H), 7.24(brs, 1H), 8.40(brd, J=7.9Hz, 1H), 8.80(dd, J=4.8, 1.6Hz, 1H), 9.37(brd, J=1.0Hz, 1H) |
| 52 | 1.72(d, J=6.6Hz 3H), 2.54(d, J=1.8Hz, 1H), 4.00(s, 3H), 4.82(dq, J=6.6, 1.8Hz, 1H), 6.89(d, J=7.0Hz, 1H), 7.24 (d, J=9.2Hz, 1H), 8.98(brs, 1H), 10.0(brs, 2H) |
| 53 | 1.70(d, J=6.5Hz, 3H), 2.50(d, J=2.0Hz, 1H), 4.85(dq, J=6.5, 2.0Hz, 1H), 6.86(d, J=7.3Hz 1H), 7.22(d, J=9.6Hz, 1H), 7.44(d, J=9.6Hz 1H), 8.37(dd, J=8.6, 2.7Hz, 1H), 9.20 (d, J=2.7Hz, 1H) |
| 54 | 3.67(s, 3H), 3.72(s, 3H), 7.22(d, J=7.5Hz, 1H), 7.31(d, J=8.4Hz 1H), 7.39(brs, 1H), 8.42(brd, J=7.9Hz, 1H), 8.83 (dd, J=4.8, 1.6Hz, 1H), 9.40(brs, 1H) |
| 55 | 1.74(d, J=6.6Hz, 3H), 2.50(d, J=2.2Hz, 1H), 4.83(dd, J=7.15, 2.85Hz, 1H), 6.82(s, 1H), 7.26(s, 1H), 7.26~7.31 (m, 1H), 8.34~8.53(m, 1H), 8.60~8.87(m, 1H) |
| 73 | 1.52(d, J=7.0Hz, 3H), 3.73(s, 3H), 3.89(q, J=7.0Hz, 1H), 7.03(d, J=7.5Hz, 1H), 7.32(d, J=8.4Hz, 1H), 7.40(brs, 1H), 8.43(brd, J=7.9Hz, 1H), 8.82(brs, 1H), 9.40(brs, 1H) |

TABLE 11

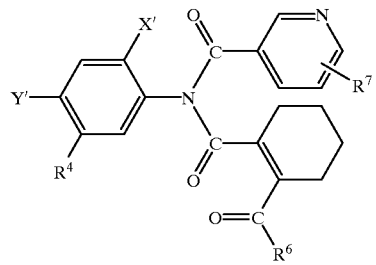

[II-A]

| Compound No. | $R^4$ | $R^7$ | $R^6$ | m.p. (°C.) |
|---|---|---|---|---|
| | | X' = F, Y' = Cl | | |
| 56 | OCH(CH$_3$)$_2$ | H | OCH$_3$ | 127~129 |
| 57 | OCHC≡CH, CH$_3$ | H | OCH$_3$ | 115~118 |
| 58 | OCHC≡CH, CH$_3$ | H | O(CH$_2$)$_2$CH$_3$ | 91~93.5 |
| 59 | OCHC≡CH, CH$_3$ | H | O(CH$_2$)$_3$CH$_3$ | 83.5~85.0 |
| 60 | OCHC≡CH, CH$_3$ | H | O(CH$_2$)$_2$OCH$_2$CH$_3$ | oil-like substance |
| 61 | OCHC≡CH, CH$_3$ | H | OCH$_2$C≡CH | oil-like substance |
| 62 | OCHC≡CH, CH$_3$ | H | —O—(cyclopentyl) | 129.5~131.5 |
| 63 | SCH$_2$COOCH$_3$ | H | OCH$_3$ | 175~176 |
| 64 | COOCH$_3$ | H | OCH$_3$ | 148~150 |
| 65 | COOCH$_3$ | H | O(CH$_2$)$_2$OCH$_3$ | oil-like substance |
| 66 | COO(CH$_2$)$_3$CH$_3$ | H | OCH$_3$ | 98~99 |
| 67 | OCHC≡CH, CH$_3$ | 5-COOCH$_3$ | OCH$_3$ | 110~112 |
| 68 | OCHC≡CH, CH$_3$ | 6-Cl | OCH(CH$_3$)$_2$ | 91.5~94.0 |
| 69 | OCHC≡CH, CH$_3$ | 6-Cl | O(CH$_2$)$_2$OCH$_3$ | 86.5~89.0 |
| 74 | OCHC≡CH, CH$_3$ | H | O(CH$_2$)$_2$OCH$_3$ | oil-like substance |

TABLE 12

| Compound No. | ¹H-NMR Absorption Spectrum Values (δ) (CDCl₃) |
|---|---|
| 56 | 1.38(d, J=6.2Hz, 6H), 1.53~1.86(m, 4H), 2.17~2.69(m, 4H), 3.75(s, 3H), 4.55(sev, J=6.2Hz, 1H), 7.02(d, J=9.2Hz, 1H), 7.25(dd, J=7.8, 4.7Hz, 1H), 7.48(d, J=6.8Hz, 1H), 7.88(dd, J=7.8, 2.0Hz, 1H), 8.60(brd, J=4.7Hz, 1H), 8.77(brs, 1H) |
| 57 | 1.54~1.86(m, 4H), 1.72(d, J=6.6Hz, 3H), 2.14~2.62(m, 4H), 2.65(d, J=2.0Hz, 1H), 3.74(s, 3H), 4.91(dq, J=6.6, 2.0Hz, 1H), 7.02(d, J=9.2Hz, 1H), 7.01~7.26(m, 1H), 7.68 (d, J=6.6Hz, 1H), 7.78(brd, J=7.0Hz, 1H), 8.50(brs, 1H), 8.66(brs, 1H) |
| 58 | 0.92(t, J=6.8Hz, 3H), 1.45~1.93(m, 6H), 1.72(d, J=6.6Hz, 3H), 2.17~2.73(m, 4H), 2.63(d, J=2.2Hz, 1H), 4.10(t, J=6.6Hz, 2H), 4.92(dq, J=6.6, 2.2Hz, 1H), 7.01(d, J=9.0Hz, 1H), 7.21(ddd, J=7.9, 5.0, 1.0Hz, 1H), 7.71(d, J=6.6Hz, 1H), 7.87(dt, J=7.9, 1.8Hz, 1H), 8.58(dd, J=5.0, 1.8Hz, 1H), 8.77~8.91(m, 1H) |
| 59 | 0.90(t, J=6.4Hz, 3H), 1.08~1.92(m, 8H), 1.72(d, J=6.4Hz, 3H), 2.16~2.69(m, 4H), 2.63(d, J=2.0Hz, 1H), 4.15(t, J=6.1Hz, 2H), 4.95(dq, J=6.4, 2.0Hz, 1H), 7.01(d, J=9.0Hz, 1H), 7.21(dd, J=8.1, 5.0Hz, 1H), 7.71(d, J=6.8Hz, 1H), 7.85(dt, J=8.1, 1.5Hz, 1H), 8.57(dd, J=5.0, 1.5Hz, 1H), 8.72~8.88(m, 1H) |
| 60 | 1.15(t, J=7.0Hz, 3H), 1.50~1.92(m, 4H), 1.71(d, J=6.4Hz, 3H), 2.20~2.73(m, 4H), 2.68(d, J=2.0Hz, 1H), 3.49(q, J=7.0Hz, 2H), 3.57~3.77(m, 2H), 4.20~4.46(m, 2H), 4.92(dq, J=6.4, 2.0Hz, 1H), 7.03(d, J=9.2Hz, 1H), 7.25(dd, J=8.1, 5.0Hz, 1H), 7.70(d, J=6.8Hz, 1H), 7.89(brd, J=8.1Hz, 1H), 8.64(brd, J=5.0Hz, 1H), 8.78(brs, 1H) |
| 61 | 1.53~1.93(m, 4H), 1.72(d, J=6.4Hz, 3H), 2.17~2.71(m, 4H), 2.44(t, J=2.5Hz, 1H), 2.69(d, J=2.0Hz, 1H), 4.76(d, J=2.5Hz, 2H), 4.92(dq, J=6.4, 2.0Hz, 1H), 7.01(d, J=9.0Hz, 1H), 7.23(dd, J=7.9, 4.6Hz, 1H), 7.71(d, J=6.8Hz, 1H), 7.86(dt, J=7.9, 1.8Hz, 1H), 8.37~8.85(m, 2H) |
| 62 | 1.30~1.98(m, 12H), 1.73(d, J=6.6Hz, 3H), 2.14~2.70(m, 4H), 2.64(d, J=1.8Hz, 1H), 4.92 (dq, J=6.6, 1.8Hz, 1H), 5.10~5.40(m, 1H), 7.01(d, J=9.0Hz, 1H), 7.21(dd, J=7.9, 4.8Hz, 1H), 7.76(d, J=6.6Hz, 1H), 7.88(dt, J=7.9, 1.8Hz, 1H), 8.58(dd, J=4.8, 1.8Hz, 1H), 8.72[8.90(m, 1H) |
| 63 | 1.53~1.87(m, 4H), 2.17~2.70(m, 4H), 3.69(s, 2H), 3.76 (s, 3H), 3.77(s, 3H), 7.08(d, J=9.2Hz, 1H), 7.26(dd, J=8.0, 4.8Hz, 1H), 7.77~7.96(m, 2H), 8.61(brd, J=4.8Hz, 1H), 8.76(brs, 1H) |
| 64 | 1.51~1.89(m, 4H), 2.14~2.69(m, 4H), 3.76(s, 3), 3.93 (s, 3H), 7.14(d, J=9.5Hz, 1H), 7.21~7.39(m, 1H), 7.89 (brd, J=8.0Hz, 1H), 8.31(d, J=7.9Hz, 1H), 8.64(brd, J=5.0Hz, 1H), 8.78(brs, 1H) |
| 65 | 1.43~1.66(m, 4H), 2.14~2.66(m, 4H), 3.34(s, 3H), 3.46~3.70(m, 2H), 3.94(s, 3H), 4.22~4.42(m, 2H), 7.17(d, J=9.5Hz, 1H), 7.16~7.42(m, 1H), 7.90(brd, J=7.9Hz, 1H), 8.35(d, J=7.9Hz, 1H), 8.63(brd, J=4.7Hz, 1H), 8.80(brs, 1H) |
| 66 | 0.98(t, J=6.6Hz, 3H), 1.21~1.97(m, 8H), 2.09~2.69(m, 4H), 3.77(s, 3H), 4.35(t, J=6.2Hz, 2H), 7.14(d, J=9.4Hz, 1H), 7.17~7.36(m, 1H), 7.85(dt, J=7.9, 1.7Hz, 1H), 8.34 (d, J=8.1Hz, 1H), 8.59(brd, J=5.0Hz, 1H), 8.78(brs, 1H) |
| 67 | 1.51~1.90(m, 4H), 1.72(d, J=6.6Hz, 3H), 2.17~2.69(m, 4H), 2.68(d, J=2.0Hz, 1H), 3.77(s, 3H), 3.93(s, 3H), 7.03 (d, J=9.0Hz, 1H), 7.67(d, J=6.8Hz, 1H), 8.47(brt, J=2.0Hz, 1H), 8.90(brs, 1H), 9.15(brs, 1H) |
| 68 | 1.22(d, J=6.3Hz, 3H), 1.24(d, J=6.3Hz, 3H), 1.55~1.98 (m, 4H), 1.72(d, J=6.6Hz, 3H), 2.14~2.73(m, 4H), 2.60(d, J=2.0Hz, 1H), 4.90(dq, J=6.6, 2.0Hz, 1H), 5.04(sev, J=6.3Hz, 1H), 7.04(d, J=9.2Hz, 1H), 7.24(dd, J=8.3, 1.0Hz, 1H), 7.71(d, J=6.6Hz, 1H), 7.85(dd, J=8.3, 2.4Hz, 1H), 8.57(d, J=2.4Hz, 1H) |
| 69 | 1.53~1.89(m, 4H), 1.72(d, J=6.6Hz, 3H), 2.24~2.68(m, 4H), 2.63(d, J=2.0Hz, 1H), 3.33(s, 3H), 3.49~3.72(m, 2H), 4.23~4.42(m, 2H), 4.90(dq, J=6.6, 2.0Hz, 1H), 7.06 (d, J=9.2Hz, 1H), 7.25(dd, J=8.4, 1.0Hz, 1H), 7.86(dd, J=8.4, 2.6Hz, 1H), 8.57(d, J=2.6Hz, 1H) |
| 74 | 1.48~1.79(m, 4H), 1.72(d, J=6.6Hz, 3H), 2.18~2.88(m, 4H), 2.65(d, J=2.0Hz, 1H), 3.33(s, 3H), 3.46~3.71(m, 2H), 4.20~4.43(m, 2H), 4.92(dq, J=6.6, 2.0Hz, 1H), 7.03 (d, J=9.2Hz, 1H), 7.22(dd, J=7.9, 4.4Hz, 1H), 7.69(d, J= |

TABLE 12-continued

| Compound No. | ¹H-NMR Absorption Spectrum Values (δ) (CDCl₃) |
|---|---|
| | 6.8Hz, 1H), 7.88(dt, J=7.9, 2.0Hz, 1H), 8.59(brd, J=4.4Hz, 1H), 8.77(brs, 1H) |
| 75 | 0.93(t, J=7.0Hz, 3H), 1.38~1.94(m, 6H), 2.14~2.70(m, 4H), 3.70(s, 2H), 3.77(s, 3H), 4.12(t, J=6.4Hz, 2H), 7.08 (d, J=9.2Hz, 1H), 7.27(dd, J=7.5, 4.6Hz, 1H), 7.82(brd, J=7.5Hz, 1H), 7.97(d, J=7.5Hz, 1H), 8.60(brd, J=4.6Hz, 1H), 8.76(brs, 1H) |
| 76 | 0.92(t, J=7.0Hz, 3H), 1.34~1.95(m, 4H), 1.51(d, J=7.3Hz, 3H), 2.14~2.74(m, 4H), 3.73(s, 3H), 3.85(q, J=7.3Hz, 1H), 4.14(t, J=7.0Hz, 2H), 7.09(d, J=9.2Hz, 1H), 7.12~ 7.50(m, 1H), 7.87(brd, J=9.0Hz, 1H), 8.04(d, J=7.9Hz, 1H), 8.30~9.06(m, 1H) |
| 70 | 1.75(d, J=6.4Hz, 3H), 1.60~1.92(m, 4H), 2.18~2.85(m, 5H), 3.75(s, 3H), 4.38~5.14(m, 1H), 7.27(s, 1H), 7.06~ 7.40(m, 1H), 7.83(s, 1H), 7.76~8.06(m, 1H), 8.46~8.66 (m, 1H), 8.70~8.82(m, 1H) |
| 71 | 1.74(s, J=6.6Hz, 3H), 1.55~1.97(m, 4H), 2.07~2.82(m, 5H), 3.33(s, 3H), 3.54~3.64(m, 2H), 4.21~4.32(m, 2H), 4.80~5.09(m, 1H), 7.03~7.33(m, 1H), 7.27(s, 1H), 7.75~ 8.01(m, 1H), 7.83(s, 1H), 8.47~8.69(m, 1H), 8.75~ 8.89(m, 1H) |

REFERENTIAL EXAMPLE 3

Synthesis of N-[4-chloro-2-fluoro-5-(1-methylpropargyloxy)phenyl]-2-thiophenecarboxyamide (A compound that is represented by No. 77 in the aftermentioned Table 13 and by the general formula [X])

47.0 g (0.22 mol) of 4-chloro-2-fluoro-5-(1-methylpropargyloxy)aniline was dissolved in 200 ml of methylene chloride, and then 36.5 ml (0.26 mol) of trimethylamine was added thereto under room temperature. Under stirring, 38.7 g (0.26 mol) of tenoyl chloride was dissolved in 100 ml of methylene chloride, and then it was added dropwise thereto at a temperature from 5 to 10° C. After the dropwise addition, it was dried with anhydrous magnesium sulfate. The solvent was removed under reduced pressure, thereby to obtain crystals. Recrystallization from ethyl acetate/n-hexane was conducted, thereby to obtain 68.09 g of N-[4-chloro-2-fluoro-5-(1-methylpropargyloxy) phenyl]-2-thiophenecarboxyamide. The melting point was 143–144° C.

Table 13 shows anilide derivatives [X] which were obtained in manners analogous to that of Referential Example 3, and Table 14 shows ¹H-NMR absorption spectrum values thereof.

TABLE 13

[X-B]

[chemical structure: 2-fluoro-4-chloro-5-$R^4$-phenyl N-H linked to C(=O)-thiophene-$R^8$]

[X-C]

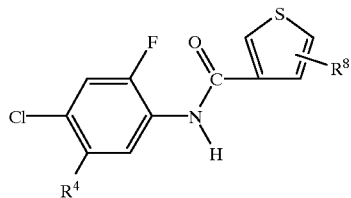

| Compound No. | R⁴ | R⁸ | m.p. (° C.) |
|---|---|---|---|
| [X-B] | | | |
| 77 | OCHC≡CH<br>\|<br>CH₃ | H | 143~144 |
| 78 | OCHC≡CH<br>\|<br>CH₃ | 3-CH₃ | 113~114 |
| 79 | OCHC≡CH<br>\|<br>CH₃ | 5-CH₃ | 102~103 |
| 80 | OCHC≡CH<br>\|<br>CH₃ | 5-Cl | 108~110 |
| 81 | —O-cyclopentyl | H | 126~127 |
| 82 | OCH₂COOCH₃ | H | 154~157 |
| [X-C] | | | |
| 83 | OCHC≡CH<br>\|<br>CH₃ | H | 148~149 |

TABLE 14

| Compound No. | $^1$H-NMR Absorption Spectrum Values (δ) (CDCl₃) |
|---|---|
| [X-B] | |
| 77 | 1.71(d, J=6.6Hz, 3H), 2.54(d, J=2.2Hz, 1H), 4.71~5.04 (m, 1H), 7.0~7.21(m, 2H), 7.17(d, J=10.3Hz, 1H), 7.41~7.65(m, 1H), 7.89(brs, 1H), 8.39(d, J=7.3Hz, 1H) |
| 78 | 1.68(d, J=6.4Hz, 3H), 2.58(s, 3H), 3.07(s, J=2Hz, 1H), 5.06 (dq, J=6.4, 2.0Hz, 1H), 7.03(d, J=4.6Hz, 1H), 7.36(d, J=10.3Hz, 1H), 7.61(d, J=5.05Hz, 1H), 8.16(d, J=7Hz, 1H), 8.72(brs, 1H) |
| 79 | 1.67(d, J=6.6Hz, 3H), 2.53(s, 3H), 3.1(d, J=2Hz, 1H), 5.04 (dq, J=6.6, 2.0Hz, 1H), 6.88(dd, J=3.7, 1.1Hz, 1H), 7.33 (d, J=10.1Hz, 1H), 7.77(d, J=3.95Hz, 1H), 8.06(d, J=7Hz, 1H) |
| 80 | 1.71(d, J=6.6Hz, 3H), 2.55(d, J=2Hz, 1H), 4.76~5.08(m, 1H), 6.95(d, J=3.95Hz, 1H), 7.17(d, J=9.9Hz, 1H), 7.43 (d, J=3.95Hz, 1H), 7.9(brs, 1H), 8.3(d, J=7.3Hz, 1H) |
| 81 | 1.48~2.13(m, 8H), 4.72~5.0(m, 1H), 7.2(dd, J=5.05, 2.7Hz, 1H), 7.28(d, J=10.3Hz, 1H), 7.81(dd, J=4.6, 1.1Hz, 1.48~2.13(m, 8H), 4.72~5.0(m, 1H), 7.2(dd, J=5.05, 3.7Hz, 1H), 7.28(d, J=10.3Hz, 1H), 7.81(dd, J=4.6, 1.1Hz, 1H), 7.87(d, 6.15Hz, 1H), 7.99(dd, J=3.7, 1.1Hz, 1H) |
| 82 | 3.76(s, 3H), 4.85(s, 2H), 7.2(dd, J=4.95, 3.95Hz, 1H), 7.35 (d, J=10.1Hz, 1H), 7.48~7.9(m, 1H), 7.81(d, J=6.4Hz, 1H), 7.97(dd, J=3.95, 1.3Hz, 1H) |
| [X-C] | |

TABLE 14-continued

| Compound No. | $^1$H-NMR Absorption Spectrum Values (δ) (CDCl₃) |
|---|---|
| 83 | 1.72(d, J=6.6Hz, 3H), 2.55(d, J=2Hz, 1H), 4.94(m, 1H), 7.17 (d, J=10.3Hz, 1H), 7.35~7.6(m, 2H), 7.9(brs, 1H), 7.69~8.08(m, 1H), 8.42(d, J=7.3Hz, 1H) |

Measurement Solvents: CDCl3 No. 77, 80, and 83
acetone-d6 No. 78, 79, 81 and 82

EXAMPLE 6

Production of N-[4-chloro-2-fluoro-5-(1-methylpropargyloxy)phenyl]-2-thiophenecarboxyimidoylchloride (A compound that is represented by No. 84 in the aftermentioned Table 15 and by the general formula [IV])

50.51 g (0.156 mol) of N-[4-chloro-2-fluoro-5-(1-methylpropargyloxy)phenyl]-2-thiophenecarboxyamide and 32.49 g (0.156 mol) of phosphorus pentachloride were suspended in 500 ml of benzene, followed by heating to 60° C. and then by stirring for 1.5 hr. After the reaction, the reaction liquid was concentrated under reduced pressure, thereby to obtain crystals. Recrystallization from benzenein-hexane was conducted, thereby to obtain 48.5 g of N-[4-chloro-2-fluoro-5-(1-methylpropargyloxy)phenyl]-2-thiophenecarboxyimidoylchloride. The melting point was 108–110° C.

EXAMPLE 7

Production of N-[4-chloro-2-fluoro-5-(1-methylproparzyloxy)phenyl]-N-(2-thiophenecarboxy)-3,4,5,6-tetrahydrophthalamic acid methyl ester (A compound that is represented by No. 91 in the aftermentioned Table 17 and by the general formula [II])

In a stream of nitrogen, a potassium salt of 3,4,5,6-tetrehydrophthalamic acid monomethyl ester was suspended in 500 ml of N,N-dimethylformamide, and then under stirring 47.91 g (0.14 mol) of N-[4-chloro-2-fluoro-5-(1-methylpropargyloxy)phenyl]-2-thiophenecarboxyimidoylchloride was added thereto. It was heated to 70° C. and then stirred for 3 hr. After the reaction, the solvent was removed under reduced pressure, and then water was added to the residue. It was extracted with ethyl acetate and then washed with water and then dried with anhydrous magnesium sulfate. After removal of the drying agent, n-hexane was added thereto. Then, the precipitated crystals were removed by filtration. The filtrate was concentrated under reduced pressure, thereby to obtain crystals. Recrystallization from methanol was conducted, thereby to obtain 37.41 g of N-[4-chloro-2-fluoro-5-(1-methylpropargyloxy)phenyl]-N-(2-thiophenecarboxy)-3,4,5,6-tetrahydrophthalamic acid methyl ester. The melting point was 93–96° C.

Tables 17 and 18 show N-phenyltetrahydrophthalamic acid derivatives [II] which are compounds of the present invention and were obtained in manners analogous to those of the foregoing Examples 6–7, and Table 19 shows $^1$H-NMR absorption spectrum values thereof. Table 15 shows imidoylchloride derivatives [IV] which are compounds of the present invention, and Table 16 shows $^1$H-NMR absorption spectrum values thereof. However, the compounds of the present invention are not limited to these.

The compound Nos. will be employed in the following examples and experiments, too.

TABLE 15

[IV-B]

[structure: 4-Cl, 2-F, 5-R⁴ substituted phenyl-N=C(Cl)-thiophene-R⁸ (2-thienyl)]

[IV-C]

[structure: 4-Cl, 2-F, 5-R⁴ substituted phenyl-N=C(Cl)-thiophene-R⁸ (3-thienyl)]

| Compound No. | R⁴ | R⁸ |
|---|---|---|
| [IV-B] | | |
| 84 | OCHC≡CH, CH₃ | H |
| 85 | OCHC≡CH, CH₃ | 3-CH₃ |
| 86 | OCHC≡CH, CH₃ | 5-CH₃ |
| 87 | OCHC≡CH, CH₃ | 5-Cl |
| 88 | —O-cyclopentyl | H |
| 89 | OCH₂COOCH₃ | H |
| [IV-C] | | |
| 90 | OCHC≡CH, CH₃ | H |

TABLE 16

| Compound No. | $^1$H-NMR Absorption Spectrum Values (δ) (CDCl₃) |
|---|---|
| [IV-B] | |
| 84 | 1.71(d, J=6.6Hz, 3H), 2.52(d, J=Hz, 1H), 4.82(dq, J=6.6, 2.0Hz, 1H), 6.88(d, J=7.3Hz, 1H), 7.2(d, J=9.5Hz, 1H), 7.4~7.62(m, 2H), 7.68~7.82(m, 1H) |
| 85 | 1.72(d, J=6.6Hz, 3H), 2.52(d, J=2Hz, 1H), 2.6(s, 3H), 4.83 (dq, J=6.6, 2.0Hz, 1H), 6.88(d, J=7Hz, 1H), 6.99(d, J=5.3Hz, 1H), 7.2(d, J=9.9Hz, 1H), 7.46(d, J=5.1Hz, 1H) |

TABLE 16-continued

| Compound No. | $^1$H-NMR Absorption Spectrum Values (δ) (CDCl₃) |
|---|---|
| 86 | 1.71(d, J=6.6Hz, 3H), 2.48(d, J=2Hz, 1H), 2.54(s, 3H), 4.81 (dq, J=6.6, 2.0Hz, 1H), 6.8(m, 1H), 6.86(d, J=7Hz, 1H), 7.19(d, J=9.5Hz, 1H), 7.64(d, J=3.7Hz, 1H) |
| 87 | 1.72(d, J=6.6Hz, 3H), 2.52(d, J=2Hz, 1H), 4.8(m, 1H), 6.87 (d, J=4.2Hz, 1H), 6.88(d, J=7Hz, 1H), 7.21(d, J=9.9Hz, 1H), 7.62(d, J=4.2Hz, 1H) |
| 88 | 1.33~2.05(m, 8H), 4.53~4.79(m, 1H), 6.60(d, J=7Hz, 1H), 7.06(m, 1H), 7.15(d, J=10.1Hz, 1H), 7.53(m, 1H), 7.77 (m, 1H) |
| 89 | 3.80(s, 3H), 4.68(s, 2H), 6.59(d, J=6.8Hz, 1H), 7.12~7.32 (m, 1H), 7.12(d, J=8.6Hz, 1H), 7.62(m, 1H), 7.84(m, 1H) |
| [IV-C] | |
| 90 | 1.71(d, J'6.6Hz, 3H), 2.52(d, J'2Hz, 1H), 4.82(dq, J=6.6, 2.0Hz, 1H), 6.86(d, J=7Hz, 1H), 7.2(d, J=9.5Hz, 1H), 7.37 (dd, J=5.1, 3.1Hz, 1H), 7.69(dd, J=5.1, 1.3Hz, 1H), 8.14 (dd, J=3.1, 1.3Hz, 1H) |

TABLE 17

[II-B]

[structure: 4-Cl, 2-F, 5-R⁴ substituted phenyl-N with C(=O)-thiophene-R⁸ and C(=O)-cyclohexenyl-C(=O)-R⁶]

| Compound No. | R⁴ | R⁸ | R⁶ | m.p. (° C.) |
|---|---|---|---|---|
| 91 | OCHC≡CH, CH₃ | H | OCH₃ | 93~96 |
| 92 | OCHC≡CH, CH₃ | H | O(CH₂)₂CH₃ | 119~120 |
| 93 | OCHC≡CH, CH₃ | H | O(CH₂)₃CH₃ | oil-like substance |
| 94 | OCHC≡CH, CH₃ | H | O(CH₂)₂OCH₃ | oil-like substance |
| 95 | OCHC≡CH, CH₃ | 3-CH₃ | OCH₃ | oil-like substance |
| 96 | OCHC≡CH, CH₃ | 5-CH₃ | OCH₃ | 129~130 |
| 97 | OCHC≡CH, CH₃ | 5-Cl | OCH₃ | oil-like substance |

TABLE 17-continued

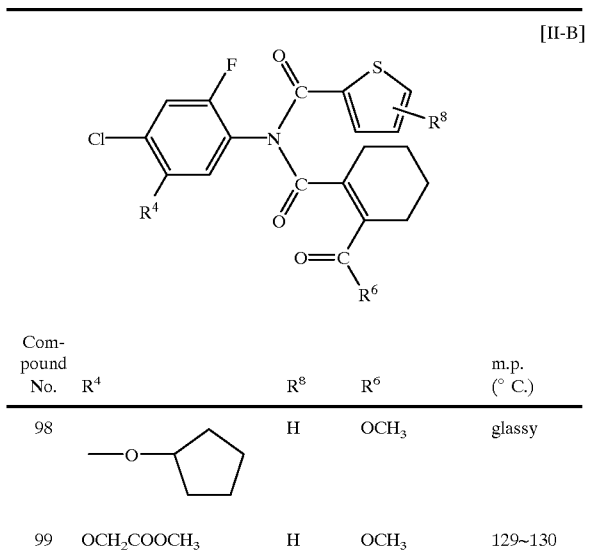

[II-B]

| Compound No. | R⁴ | R⁸ | R⁶ | m.p. (° C.) |
|---|---|---|---|---|
| 98 | —O—cyclopentyl | H | OCH₃ | glassy |
| 99 | OCH₂COOCH₃ | H | OCH₃ | 129~130 |

TABLE 18

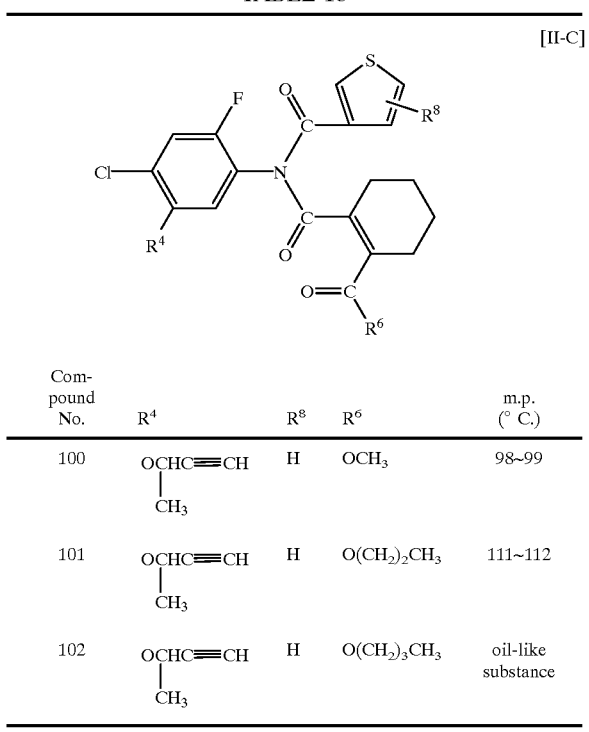

[II-C]

| Compound No. | R⁴ | R⁸ | R⁶ | m.p. (° C.) |
|---|---|---|---|---|
| 100 | OCHC≡CH\|CH₃ | H | OCH₃ | 98~99 |
| 101 | OCHC≡CH\|CH₃ | H | O(CH₂)₂CH₃ | 111~112 |
| 102 | OCHC≡CH\|CH₃ | H | O(CH₂)₃CH₃ | oil-like substance |

TABLE 19

| Compound No. | ¹H-NMR Absorption Spectrum Values (δ) (CDCl₃) |
|---|---|
| | [II-B] |
| 91 | 1.72(d, J'6.6Hz, 3H), 1.56~1.88(m, 4H), 2.2~2.84(m, 4H), 2.49(d, J=2Hz, 1H), 3.68(s, 3H), 4.94(dq, J=6.6, 2.0Hz, 1H), 6.89(dd, J=4.95, 3.95Hz, 1H), 7.15(d, J=9.0Hz, 1H), 7.27(dd, J=3.95, 1.1Hz, 1H), 7.49(dd, J=4.95, 1.1Hz, 1H), 7.65(d, J=6.8Hz, 1H) |

TABLE 19-continued

| Compound No. | ¹H-NMR Absorption Spectrum Values (δ) (CDCl₃) |
|---|---|
| 92 | 0.87(t, J=7Hz, 3H), 1.4~1.88(m, 6H), 1.73(d, J=6.6Hz, 3H), 2.2~2.68(m, 4H), 2.47(d, J=2Hz, 1H), 4.03(t, J=7Hz, 2H), 4.94(m, 1H), 6.88(m, 1H), 7.1(d, J=9Hz, 1H), 7.25 (m, 1H), 7.48(m, 1H), 7.7(d, J=6.6Hz, 1H) |
| 93 | 0.85(t, J=6.4Hz, 3H), 1.2~1.9(m, 8H), 1.72(d, J=6.6Hz, 3H), 2.1~2.68(m, 4H), 2.48(d, J=2Hz, 1H), 4.08(t, J=6.4Hz, 2H), 4.94(dq, J=6.6, 2Hz, 1H), 6.88(dd, J=5.1, 3.95Hz, 1H), 7.14(d, J=8.8Hz, 1H), 7.25(dd, J=3.95, 1.1Hz, 1H), 7.49(dd, J=5.1, 1.3Hz, 1H), 7.72(d, J=6.8Hz, 1H) |
| 94 | 1.51~1.87(m, 4H), 1.72(d, J=6.4Hz, 3H), 2.17~2.65(m, 4H), 2.50(d, J=2.2Hz, 1H), 3.28(s, 3H), 3.39~3.61(m, 2H), 4.11~4.31(m, 2H), 4.94(m, 1H), 6.89(dd, J=4.95, 3.85Hz, 1H), 7.15(d, J=9.0Hz, 1H), 7.27(dd, J=3.85, 1.2Hz, 1H), 7.50(dd, J=4.95, 1.2Hz, 1H), 7.72(d, J=6.8Hz, 1H) |
| 95 | 1.56~1.9(m, 4H), 1.71(d, J=6.6Hz, 3H), 2.2~2.74(m, 4H), 2.44(s, 3H), 2.52(d, J=2Hz, 1H), 3.74(s, 3H), 4.92(dq, J=6.6, 2.0Hz, 1H), 6.77(d, J=5.1Hz, 1H), 7.07(d, J=9.5Hz, 1H), 7.25(d, J=4.8Hz, 1H), 7.63(d, J=6.8Hz, 1H) |
| 96 | 1.54~1.9(m, 4H), 1.74(d, J=6.6Hz, 3H), 2.2~2.68(m, 4H), 2.42(s, 3H), 2.49(d, J=2Hz, 1H), 3.68(s, 3H), 4.94(m, 1H), 6.5~6.64(m, 1H), 7.1(d, J=3.3Hz, 1H), 7.17(d, J=9Hz, 1H), 7.64(d, J=6.8Hz, 1H) |
| 97 | 1.56~1.9(m, 4H), 1.74(d, J=6.6Hz, 3H), 2.2~2.68(m, 4H), 2.5(d, J'2Hz, 1H), 3.69(s, 3H), 4.95(dq, J=6.6, 2.0Hz, 1H), 6.74(d, J=4.2Hz, 1H), 7.1(d, J=4.2Hz, 1H), 7.2(d, J=9Hz, 1H), 7.64(d, J=6.8Hz, 1H) |
| 98 | 1.48~2.04(m, 12H), 2.2~2.68(m, 4H), 3.67(s, 3H), 4.68~4.94(m, 1H), 6.91(dd, J=5.0, 3.85Hz, 1H), 7.12(d, J=9.0Hz, 1H), 7.29(dd, J=3.85, 1.3Hz, 1H), 7.48(d, J=7.25Hz 1H), 7.5(dd, J=5.0, 1.3Hz, 1H) |
| 99 | 1.56~1.9(m, 4H), 2.2~2.68(m, 4H), 3.67(s, 3H), 3.79(s, 3H), 4.77(s, 2H), 6.92(dd, J=5.1, 2.85Hz, 1H), 7.17(d, J=8.8Hz, 1H), 7.22(dd, J=3.85, 1.3Hz, 1H), 7.43(d, J=6.6Hz, 1H), 7.51(dd, J=5.1, 1.3Hz, 1H) |
| | [II-C] |
| 100 | 1.73(d, J=6.6Hz, 3H), 1.12~1.86(m, 4H), 2.2~2.68(m, 4H), 2.53(d, J=2Hz, 1H), 3.7(s, 3H), 4.9(m, 1H), 7.08(d, J=9Hz, 1H), 7.06~7.2(m, 2H), 7.6~7.66(m, 1H), 7.67(d, J=6.6Hz, 1H) |
| 101 | 0.89(t, J=6.6Hz, 3H), 1.4~1.84(m, 6H), 1.73(d, J=6.6Hz, 3H), 2.2~2.68(m, 4H), 2.52(d, J=2Hz, 1H), 4.05(t, J=6.6Hz, 2H), 4.93(dq, J=6.6, 2.0Hz, 1H), 7.04~7.24(m, 2H), 7.07(d, J=9.7Hz, 1H), 7.6~7.7(m, 1H), 7.67(d, J=6.8Hz, 1H) |
| 102 | 0.89(t, J'6.6Hz, 3H), 1.2~1.85(m, 8H), 1.74(d, J=6.6Hz, 3H), 2.2~2.7(m, 4H), 2.53(d, J=2Hz, 1H), 4.1(t, J=6.6Hz, 2H), 4.95(dq, J=6.6, 2.0Hz, 1H), 7.06~7.26(m, 2H), 7.08(d, J=9.7Hz, 1H), 7.6~7.72(m, 1H), 7.72(d, J=6.8Hz, 1H) |

A herbicide of the present invention containing as the effective component an N-phenyltetrahydrophthalamic acid derivative [I] or [II] that is a compound of the present invention has a superior herbicidal activity against various weeds causing problems upon the submerged soil treatment in paddy fields, such as gramineous weeds such as nobie (barnyardgrass, *Echinochloa* spp.), broad-leaved weeds such as azena (flase pimpernel, *Lindernia pyxidaria*), kikashigusa (toothcup, *Rotala indica*), mizohakobe (waterwort, *Elatine triandra*), cyperaceous weeds such as tamagayatsuri (small-flowered umbrellaplant, *Cyperus difformis*) and hotarui (bulrush, *Scirpus juncoides*), and weeds such as konagi (*Monochoria vaginalis*). Furthermore, the herbicide has a superior herbicidal activity against various weeds causing problems upon the foliage treatment and the soil treatment in uplands, such as broad-leaved weeds such as karashina (indian mustard, *Brassica juncea*), aobiyu (slender amaranth, *Amaranthus viridis*), hakobe (chickweed, *Stel-* laria media), shiroza (common lambsquarters, *Chenopodium album*), onamomi (heartleaf cocklebur, *Xanthium strumarium*), maruba-asagao (tall morningglory, *Ipomoea purpurea*), yaemugura (catchweed bedstraw, *Galium aparine*), suberihiyu (common purslane, *Portulaca oleracea*), ichibi (velvetleaf, *Abutilon theophrasti*), amerika-tsunokusanemu (hemp sesbania, *Sesbania exaltata*), ebisugusa (sicklepod, *Cassia obtusifolia*), inuhouzuki (black nightshade, *Solanum nigrum*), spedwells, smart weeds, violets, tade (*Persicaria longiseta*) and its relatives, and sumire (*Viola mandshurica*) and its relatives, gramineous weeds such as inubie (bamyardgrass, *Echinochloa crusgalli*), enokorogusa (green foxtail, *Setaria viridis*), karasumugi (wild oat, *Avena fatua*), mehishiba (henry crabgrass, *Digitaria ciliaris*), seibanmorokoshi (johnsongrass, *Sorghum halepense*) and enbaku (oat, Avena sativa), cyperaceous weeds such as kogomegayatsuri (rice flatsedge, *Cyperus iria*) and hamasuge (nut grass, *Cyperus rotundus*), and commelinaceous weeds such as tsuyukusa (dayflower, *Commelina communis*). The herbicide of the present invention hardly injures major crops such as rice, wheat, corn and soybean.

Therefore, the herbicide of the present invention can be applied to upland, paddy field, orchard, pasture, turf, forest and non-crop land.

It is possible to process the herbicide of the present invention containing as the effective component an N-phenyltetrahydrophthalamic acid derivative [I] or [II] that is a compound of the present invention into an arbitrary form such as wettable powder, emulsion, granules, powder or flowable by using a pesticide adjuvant which is generally used in this field, such as an inactive solid carrier or liquid carrier and an emulsifying and dispersing agent. As these inactive carriers, there can be cited, for example, talc, clay, bentonite, kaolin, diatomaceous earth, calcium carbonate, wood flour, starch, gum arabic, water, alcohol, kerosene, benzene, xylene, n-hexane, acetone, N,N-dimethylformamide, glycol ether, and N-methylpyrrolidone.

Besides, it is possible to adequately incorporate auxiliary agents for formulation, such as spreader, diluent, surfactant and solvent.

Upon using as a herbicide N-phenyltetrahydrophthalamic acid derivativ [I] or [II] which is a compound of the present invention, a suitable application dosage is variable according to related factors such as manner of application, object of application, time of application and occurrence condition of weeds, but in general the application dosage, as expressed as the amount of the effective component, is preferably from 0.5 g to 300 g per 1 hectare. An application dosage less than 0.5 g is not preferable, because a sufficient herbicidal effect can not be obtained. Even if an application dosage greater than 300 g is used, the herbicidal effect does not change so much. It causes only an economical disadvantage and may generate injuries. Therefore, it is not preferable. 1–300 g per 1 hectare is particularly preferable.

Furthermore, to use the herbicide containing an N-phenyltetrahydrophthalamic acid derivative [I] or [II] which is a compound of the present invention, it may be mixed with other herbicides, plant growth regulators, fungicides, insecticides, other pesticides, fertilizers and soil conditioners.

The following are Examples of herbicides according to the present invention, though compounds, carriers, adjuvants and the proportions of the ingredients are not limited to those in these examples. In these examples the amount of each component is indicated by parts by weight.

EXAMPLE 8 (Wettable Powder)

| | |
|---|---|
| Compound No. 123 | 10 parts |
| Sodium lignin sulfonate | 1.5 parts |
| Polyoxyethylene alkylaryl ether | 1.5 parts |
| Clay | 87 parts |

These materials were mixed together until a uniform mixture was obtained, and the mixture was pulverized to obtain a wettable powder.

EXAMPLE 9 (Granules)

| | |
|---|---|
| Compound No. 12 | 7 parts |
| Bentonite | 30 parts |
| Sodium alkylsulfonate | 2 parts |
| Clay | 61 parts |

These materials were mixed together and kneaded until a uniform mixture was obtained, and the mixture was granulated by an ordinary granulation method, thereby to obtain granules.

EXAMPLE 10 (Emulsion)

| | |
|---|---|
| Compound No. 12 | 5 parts |
| N-methylpyrrolidone | 44 parts |
| Solpol 7065 | 43 parts |
| (product of Toho Kagaku Kogyo Co., Ltd.) | |
| Solpol 355 | 8 parts |
| (product of Toho Kagaku Kogyo Co., Ltd.) | |

These materials were mixed together until a uniform mixture was obtained, thereby to obtain an emulsion.

The following experiments are illustrative of the herbicidal effects of N-phenyltetrahydrophthalamic derivatives [I] which are compounds of the present invention.

EXPERIMENT 1 (Flooded Soil Treatment)

Paddy soil (clay loam) was put into a pot so as to have a surface area of 1/15500 ares. Uniformly mixed seeds of several kinds of weeds, viz., nobie (barnyardgrass, Echinochloa spp.), broad-leaved weeds, hotarui (bulrush, *Scirpus juncoides*) and tamagayatsuri (small-flowered umbrellaplant, *Cyperus difformis*), were sown in the surface layer of the soil in each pot, and then paddy rice seedlings at the two- or three-leaved stage were transplanted into each pot to a depth of 2 cm, and water was fed into each pot so as to provide a 3 cm deep water layer on the soil surface. After 3 days, in other words at the initial stage of germination of nobie (barnyardgrass, Echinochloa spp.), a predetermined amount of a selected compound obtained in a manner analogous to Example 8 in the form of diluted aqueous solution was dropped into the water layer in each pot. After that, the pots were kept in a glass chamber to allow the paddy rice and the weeds to grow, and after the lapse of 4 weeks from the treatment with the selected compounds, the herbicidal effects and the degree of injury to the paddy rice were evaluated. The results are shown in Table 20. In the table, the herbicidal effects and the degree of injury to the paddy rice are indicated by numerical values, which have the following meaning.

5: completely killed
4: seriously injured
3: considerably injured
2: somewhat injured
1: slightly injured
0: not injured (normally grown)

EXPERIMENT 2 (Foliage Treatment)

Upon seedling stage (two- or three-leaved stage) of rice, cockspur (*Panicum crus-galli*), garden radish, aobiyu (slender amaranth, *Amaranthus viridis*) and mehishiba (henry crabgrass, *Digitaria cliaris*) which were grown on a cultivated soil put in pots of 1/15500 ares, a selected compound obtained in a manner analogous to Example 8, in suspended wettable powder, was sprayed to each plant. After that, the pots were kept in a glass chamber to allow each plant to grow, and after the lapse of 4 weeks from the treatment with the selected compounds the herbicidal effects were evaluated. The results are shown in Table 21. The evaluation of the herbicidal effects was similarly conducted as to that of Experiment 1.

EXPERIMENT 3 (Foliage Treatment)

Upon seedling stage (two- or three-leaved stage) of ichibi (velvetleaf, *Abutilon theophrasti*), onamomi (heartleaf cocklebur, *Xanthium strumarium*) (4L stage), noasagao (blue morningglory, *Ipomoea indica*) and ooinutade (pale smartweed, *Persicaria lapathifolia*) which were grown on a cultivated soil put in pots of 1/8850 ares, a selected compound obtained in a manner analogous to Example 8, in suspended wettable powder, was sprayed to each plant. After that, the pots were kept in a glass chamber to allow each plant to grow, and after the lapse of 4 weeks from the treatment with the selected compounds the herbicidal effects were evaluated. The results are shown in Table 22. The evaluation of the herbicidal effects was similarly conducted as to that of Experiment 1.

TABLE 20

| Compound No. | Quantity of Compound g/10a | Injury of Paddy | Herbicidal Effect | | | |
|---|---|---|---|---|---|---|
| | | | nobie | broad-leaved weed | hotarui | tamagaya tsuri |
| 11 | 25 | 0.5 | 5 | 5 | 5 | 5 |
| | 12.5 | 0 | 5 | 5 | 5 | 5 |
| 12 | 25 | 0.5 | 5 | 5 | 5 | 5 |
| | 12.5 | 0.5 | 5 | 5 | 4 | 5 |
| 13 | 25 | 0.5 | 5 | 5 | 4 | 5 |
| | 12.5 | 0 | 5 | 5 | 4 | 5 |
| 14 | 25 | 0 | 5 | 5 | 4 | 5 |
| | 12.5 | 0 | 4.5 | 5 | 4 | 5 |
| 15 | 25 | 0.5 | 5 | 5 | 4 | 5 |
| | 12.5 | 0 | 5 | 5 | 4 | 4 |
| 16 | 25 | 0.5 | 5 | 5 | 5 | 5 |
| | 12.5 | 0.5 | 5 | 5 | 5 | 5 |
| 17 | 25 | 0.5 | 5 | 5 | 5 | 5 |
| | 12.5 | 0 | 5 | 5 | 4 | 5 |
| 18 | 25 | 0 | 5 | 5 | 5 | 5 |
| | 12.5 | 0 | 5 | 5 | 4 | 5 |
| 19 | 25 | 0.5 | 5 | 5 | 5 | 5 |
| | 12.5 | 0 | 5 | 5 | 5 | 5 |
| 20 | 25 | 0.5 | 5 | 5 | 5 | 5 |
| | 12.5 | 0.5 | 5 | 5 | 5 | 5 |
| Comparative agentA | 25 | 0 | 5 | 5 | 4 | 5 |
| | 12.5 | 0 | 4.5 | 5 | 3 | 5 |

TABLE 20-continued

| Compound No. | Quantity of Compound g/10a | Injury of Paddy | Herbicidal Effect | | | |
|---|---|---|---|---|---|---|
| | | | nobie | broad-leaved weed | hotarui | tamagaya tsuri |

Comparative agent-A: MO

TABLE 21

| Compound No. | Quantity of Compound g/10a | Herbicidal Effect | | | | |
|---|---|---|---|---|---|---|
| | | rice | cockspur | garden radish | aobiyu | mehishiba |
| 11 | 80 | 1 | 1 | 5 | 5 | 1 |
| | 40 | 1 | 1 | 4 | 5 | 1 |
| 12 | 80 | 1 | 1 | 5 | 5 | 1 |
| | 40 | 1 | 1 | 5 | 5 | 1 |
| 13 | 80 | 1 | 2 | 5 | 5 | 1 |
| | 40 | 1 | 2 | 5 | 5 | 1 |
| 14 | 80 | 1 | 1 | 5 | 5 | 1 |
| | 40 | 1 | 1 | 5 | 5 | 1 |
| 15 | 80 | 1 | 1 | 5 | 5 | 1 |
| | 40 | 1 | 1 | 5 | 4.5 | 1 |
| 16 | 80 | 1 | 1 | 5 | 5 | 1 |
| | 40 | 1 | 1 | 5 | 5 | 1 |
| 17 | 80 | 1 | 2 | 5 | 5 | 1 |
| | 40 | 1 | 2 | 5 | 5 | 1 |
| 18 | 80 | 1 | 1 | 5 | 5 | 1 |
| | 40 | 1 | 1 | 5 | 4 | 1 |
| 19 | 80 | 1 | 1 | 5 | 5 | 1 |
| | 40 | 1 | 1 | 4 | 5 | 1 |
| 20 | 80 | 1 | 2 | 5 | 5 | 1 |
| | 40 | 1 | 2 | 5 | 5 | 1 |
| 33 | 80 | 1 | 1 | 5 | 5 | 1 |
| | 40 | 1 | 1 | 5 | 5 | 1 |
| 35 | 80 | 1 | 2 | 5 | 5 | 1 |
| | 40 | 1 | 1 | 5 | 5 | 1 |
| 39 | 80 | 1 | 1 | 5 | 5 | 1 |
| | 40 | 1 | 1 | 5 | 5 | 1 |
| 40 | 80 | 1 | 1 | 5 | 5 | 1 |
| | 40 | 1 | 1 | 5 | 5 | 1 |
| Comparative agentB | 80 | 0 | 0 | 4 | 5 | 1 |
| | 40 | 0 | 0 | 3 | 5 | 1 |

Comparative agent-B: Propanil

TABLE 22

| Compound No. | Quantity of Compound g/10a | Herbicidal Effect | | | |
|---|---|---|---|---|---|
| | | ichibi | onamomi | noasagao | ooinutade |
| 11 | 8 | 5 | 4 | 4 | 4 |
| | 4 | 4 | 4 | 4 | 4 |
| 13 | 8 | 5 | 5 | 5 | 5 |
| | 4 | 5 | 5 | 5 | 5 |
| 14 | 8 | 5 | 5 | 5 | 5 |
| | 4 | 5 | 4 | 5 | 4 |
| 20 | 8 | 5 | 4 | 5 | 5 |
| | 4 | 5 | 4 | 4 | 5 |
| 33 | 8 | 5 | 5 | 5 | 5 |
| | 4 | 5 | 5 | 4 | 5 |
| 35 | 8 | 5 | 4 | 5 | 5 |
| | 4 | 5 | 4 | 4 | 5 |
| 42 | 8 | 5 | 5 | 5 | 5 |
| | 4 | 5 | 5 | 5 | 5 |
| 44 | 8 | 5 | 5 | 5 | 5 |
| | 4 | 5 | 5 | 5 | 5 |
| Compara- | 8 | 3 | 5 | 4 | 5 |

TABLE 22-continued

| Com-pound No. | Quantity of Compound g/10a | Herbicidal Effect | | | |
|---|---|---|---|---|---|
| | | ichibi | onamomi | noasagao | ooinutade |
| tive agentC | 4 | 3 | 4 | 3 | 5 |

Comparative Agent-C: Pursuit

EXAMPLE 11 (Wettable Powder)

| | |
|---|---|
| Compound No. 58 | 10 parts |
| Sodium lignin sulfonate | 1.5 parts |
| Polyoxyethylene alkylaryl ether | 1.5 parts |
| Clay | 87 parts |

These materials were mixed together until a uniform mixture was obtained, and the mixture was pulverized to obtain a wettable powder.

EXAMPLE 12 (Granules)

| | |
|---|---|
| Compound No. 58 | 7 parts |
| Sodium alkylsulfonate | 2 parts |
| Clay | 61 parts |

These materials were mixed together and kneaded until a uniform mixture was obtained, and the mixture was granulated by an ordinary granulation method, thereby to obtain granules.

EXAMPLE 13 (Emulsion)

| | |
|---|---|
| Compound No. 58 | 5 parts |
| N-methylpyrrolidone | 44 parts |
| Solpol 7065 | 43 parts |
| (product of Toho Kagaku Kogyo Co., Ltd.) | |
| Solpol 355 | 8 parts |
| (product of Toho Kagaku Kogyo Co., Ltd.) | |

These materials were mixed together until a uniform mixture was obtained, thereby to obtain an emulsion.

The following experiments are illustrative of the herbicidal effects of N-phenyltetrahydrophthalamic derivatives [II] which are compounds of the present invention.

EXPERIMENT 4 (Flooded Soil Treatment)

Paddy soil (clay loam) was put into a pot so as to have a surface area of 1/15500 ares. Uniformly mixed seeds of several kinds of weeds, viz., nobie (barnyardgrass, Echinochloa spp.), broad-leaved weeds, hotarui (bulrush, *Scirpus juncoides*) and tamagayatsuri (small-flowered umbrellaplant, *Cyperus difformis*), were sown in the surface layer of the soil in each pot, and then paddy rice seedlings at the two- or three-leaved stage were transplanted into each pot to a depth of 2 cm, and water was fed into each pot so as to provide a 3 cm deep water layer on the soil surface. After 3 days, in other words at the initial stage of germination of nobie (barnyardgrass, Echinochloa spp.), a predetermined amount of a selected compound obtained in a manner analogous to Example 11 in the form of diluted aqueous solution was dropped into the water layer in each pot. After that, the pots were kept in a glass chamber to allow the paddy rice and the weeds to grow, and after the lapse of 4 weeks from the treatment with the selected compounds, the herbicidal effects and the degree of injury to the paddy rice were evaluated. The results are shown in Table 23. The evaluation of the herbicidal effects was similarly conducted as to that of Experiment 1.

EXPERIMENT 5 (Foliage Treatment)

Upon seedling stage (two- or three-leaved stage) of rice, cockspur (*Panicum crus-galli*), garden radish, aobiyu (slender amaranth, *Amaranthus viridis*) and mehishiba (henry crabgrass, *Digitaria cliaris*) which were grown on a cultivated soil put in pots of 1/15500 ares, a selected compound obtained in a manner analogous to Example 11, in suspended wettable powder, was sprayed to each plant. After that, the pots were kept in a glass chamber to allow each plant to grow, and after the lapse of 4 weeks from the treatment with the selected compounds the herbicidal effects were evaluated. The results are shown in Table 24. The evaluation of the herbicidal effects was similarly conducted as that of Experiment 1.

EXPERIMENT 6 (Foliage Treatment)

Upon seedling stage (two- or three-leaved stage) of ichibi (velvetleaf, *Abutilon theophrasti*), onamomi (heartleaf cocklebur, *Xanthium strumarium*) (4 L stage), noasagao (blue morningglory, *Ipomoea indica*) and ooinutade (pale smartweed, *Persicaria lapathifolia*) which were grown on a cultivated soil put in pots of 1/8850 ares, a selected compound obtained in a manner analogous to Example 11, in suspended wettable powder, was sprayed to each plant. After that, the pots were kept in a glass chamber to allow each plant to grow, and after the lapse of 4 weeks from the treatment with the selected compounds the herbicidal effects were evaluated. The results are shown in Table 25. The evaluation of the herbicidal effects was similarly conducted as that of Experiment 1.

TABLE 23

| Compound No. | Quantity of Compound g/10a | Injury of Paddy | Herbicidal Effect | | |
|---|---|---|---|---|---|
| | | | nobie | broad-leaved weed | hotarui | tamagaya tsuri |
| 56 | 6.25 | 0.5 | 5 | 5 | 5 | 5 |
| | 3.13 | 0.5 | 5 | 4.5 | 5 | 5 |
| 57 | 6.25 | 0.5 | 5 | 5 | 4.5 | 5 |
| | 3.13 | 0 | 5 | 5 | 4.5 | 5 |
| 58 | 6.25 | 0.5 | 5 | 5 | 4.5 | 5 |
| | 3.13 | 0 | 5 | 5 | 4 | 5 |
| 59 | 6.25 | 0.5 | 5 | 5 | 4 | 5 |
| | 3.13 | 0.5 | 5 | 5 | 4 | 5 |
| 60 | 6.25 | 0.5 | 5 | 5 | 4.5 | 5 |
| | 3.13 | 0.5 | 5 | 5 | 4.5 | 5 |
| 61 | 6.25 | 0.5 | 5 | 5 | 4 | 5 |
| | 3.13 | 0 | 5 | 5 | 4 | 5 |
| 62 | 6.25 | 0.5 | 5 | 5 | 4 | 5 |
| | 3.13 | 0 | 5 | 5 | 4 | 5 |
| 63 | 6.25 | 0 | 5 | 5 | 4 | 5 |
| | 3.13 | 0 | 5 | 5 | 4 | 4 |
| 64 | 6.25 | 0.5 | 5 | 5 | 4 | 4 |
| | 3.13 | 0 | 5 | 5 | 4 | 4 |
| 65 | 6.25 | 0 | 5 | 5 | 4 | 4 |

TABLE 23-continued

| Compound No. | Quantity of Compound g/10a | Injury of Paddy | Herbicidal Effect | | | |
|---|---|---|---|---|---|---|
| | | | nobie | broad-leaved weed | hotarui | tamagaya tsuri |
| | 3.13 | 0 | 5 | 5 | 4 | 4 |
| 66 | 6.25 | 0 | 5 | 5 | 4 | 4 |
| | 3.13 | 0 | 5 | 5 | 4 | 4 |
| 67 | 6.25 | 0.5 | 5 | 5 | 5 | 5 |
| | 3.13 | 0.5 | 5 | 5 | 4 | 5 |
| 68 | 6.25 | 0.5 | 5 | 5 | 4.5 | 5 |
| | 3.13 | 0 | 5 | 5 | 4 | 5 |
| 69 | 6.25 | 0.5 | 5 | 5 | 4.5 | 5 |
| | 3.13 | 0.5 | 5 | 5 | 4 | 5 |
| 70 | 6.25 | 0 | 5 | 5 | 4 | 5 |
| | 3.13 | 0 | 5 | 5 | 4 | 5 |
| 71 | 6.25 | 0 | 5 | 5 | 4 | 5 |
| | 3.13 | 0 | 5 | 5 | 4 | 5 |
| Comparative agentA | 6.25 | 0 | 5 | 5 | 4 | 5 |
| | 3.13 | 0 | 4.5 | 5 | 3 | 5 |

Comparative Agent-A: MO

TABLE 24

| Compound No. | Quantity of Compound g/10a | Herbicidal Effect | | | |
|---|---|---|---|---|---|
| | | rice | cockspur | garden radish | aobiyu | mehishiba |
| 56 | 80 | 1 | 1 | 5 | 5 | 1 |
| | 40 | 1 | 1 | 5 | 5 | 1 |
| 57 | 80 | 1 | 3 | 5 | 5 | 4 |
| | 40 | 1 | 1 | 5 | 5 | 4 |
| 58 | 80 | 1 | 1 | 5 | 5 | 3 |
| | 40 | 1 | 1 | 5 | 5 | 1 |
| 59 | 80 | 1 | 1 | 5 | 5 | 1 |
| | 40 | 1 | 0 | 5 | 5 | 1 |
| 60 | 80 | 4 | 1 | 5 | 5 | 5 |
| | 40 | 2 | 1 | 5 | 5 | 4 |
| 61 | 80 | 4 | 2 | 5 | 5 | 5 |
| | 40 | 3 | 2 | 5 | 5 | 4.5 |
| 62 | 80 | 1 | 1 | 5 | 5 | 1 |
| | 40 | 1 | 1 | 4.5 | 5 | 1 |
| 63 | 80 | 1 | 1 | 4.5 | 5 | 1 |
| | 40 | 1 | 1 | 4.5 | 5 | 1 |
| 64 | 80 | 1 | 1 | 5 | 5 | 2 |
| | 40 | 1 | 1 | 5 | 5 | 1 |
| 65 | 80 | 1 | 1 | 5 | 5 | 1 |
| | 40 | 1 | 1 | 5 | 5 | 1 |
| 66 | 80 | 1 | 1 | 5 | 5 | 2 |
| | 40 | 1 | 1 | 4.5 | 5 | 1 |
| 67 | 80 | 1 | 1 | 5 | 5 | 1 |
| | 40 | 1 | 1 | 5 | 5 | 1 |
| 68 | 80 | 1 | 1 | 5 | 5 | 1 |
| | 40 | 1 | 1 | 5 | 5 | 1 |
| 69 | 80 | 1 | 1 | 5 | 5 | 2 |
| | 40 | 1 | 1 | 4.5 | 5 | 2 |
| 70 | 80 | 1 | 1 | 5 | 5 | 2 |
| | 40 | 1 | 1 | 4 | 5 | 2 |
| 71 | 80 | 1 | 1 | 5 | 5 | 2 |
| | 40 | 1 | 1 | 4 | 5 | 2 |
| Comparative agentB | 80 | 0 | 0 | 4 | 5 | 1 |
| | 40 | 0 | 0 | 3 | 5 | 1 |

Comparative agent-B: Propanil

TABLE 25

| Compound | Quantity of Compound | Herbicidal Effect | | | |
|---|---|---|---|---|---|
| No. | g/10a | ichibi | onamomi | noasagao | ooinutade |
| 57 | 8 | 5 | 4 | 4 | 5 |
| | 4 | 5 | 4 | 4 | 5 |
| 60 | 8 | 5 | 5 | 5 | 5 |
| | 4 | 5 | 5 | 5 | 5 |
| 64 | 8 | 5 | 5 | 5 | 5 |
| | 4 | 5 | 4 | 4 | 5 |
| 67 | 8 | 5 | 5 | 5 | 5 |
| | 4 | 5 | 4 | 5 | 5 |
| Comparative agentC | 8 | 3 | 5 | 4 | 5 |
| | 4 | 3 | 4 | 3 | 5 |

Comparative Agent-C: Pursuit

EXAMPLE 14 (Wettable Powder)

| | |
|---|---|
| Compound No. 100 | 10 parts |
| Sodium lignin sulfonate | 1.5 parts |
| Polyoxyethylene alkylaryl ether | 1.5 parts |
| Clay | 87 parts |

These materials were mixed together until a uniform mixture was obtained, and the mixture was pulverized to obtain a wettable powder.

EXAMPLE 15 (Granules)

| | |
|---|---|
| Compound No. 100 | 7 parts |
| Bentonite | 30 parts |
| Sodium alkylsulfonate | 2 parts |
| Clay | 61 parts |

These materials were mixed together and kneaded until a uniform mixture was obtained, and the mixture was granulated by an ordinary granulation method, thereby to obtain granules.

EXAMPLE 16 (Emulsion)

| | |
|---|---|
| Compound No. 100 | 5 parts |
| N-methylpyrrolidone | 44 parts |
| Solpol 7065 | 43 parts |
| (product of Toho Kagaku Kogyo Co., Ltd.) | |
| Solpol 355 | 8 parts |
| (product of Toho Kagaku Kogyo Co., Ltd.) | |

These materials were mixed together until a uniform mixture was obtained, thereby to obtain an emulsion.

The following experiments are illustrative of the herbicidal effects of N-phenyltetrahydrophthalamic derivatives [II] which are compounds of the present invention.

EXPERIMENT 7 (Flooded Soil Treatment)

Paddy soil (clay loam) was put into a pot so as to have a surface area of 1/15500 ares. Uniformly mixed seeds of several kinds of weeds, viz., nobie (barnyardgrass, Echinochloa spp.), broad-leaved weeds, hotarui (bulrush, *Scirpus juncoides*) and tamagayatsuri (small-flowered umbrellaplant, *Cyperus difformis*), were sown in the surface layer of the soil in each pot, and then paddy rice seedlings at the two- or three-leaved stage were transplanted into each pot to a depth of 2 cm, and water was fed into each pot so as to provide a 3 cm deep water layer on the soil surface. After 3 days, in other words at the initial stage of germination of nobie (barnyardgrass, Echinochloa spp.), a predetermined amount of a selected compound obtained in a manner analogous to Example 14 in the form of diluted aqueous solution was dropped into the water layer in each pot. After that, the pots were kept in a glass chamber to allow the paddy rice and the weeds to grow, and after the lapse of 4 weeks from the treatment with the selected compounds, the herbicidal effects and the degree of injury to the paddy rice were evaluated. The results are shown in Table 26. The evaluation of the herbicidal effects was similarly conducted as that of Experiment 1.

EXPERIMENT 8 (Foliage Treatment)

Upon seedling stage (two- or three-leaved stage) of rice, cockspur (*Panicum crus-galli*), garden radish, aobiyu (slender amaranth, *Amaranthus viridis*) and mehishiba (henry crabgrass, *Digitaria cliaris*) which were grown on a cultivated soil put in pots of 1/15500 ares, a selected compound obtained in a manner analogous to Example 14, in suspended wettable powder, was sprayed to each plant. After that, the pots were kept in a glass chamber to allow each plant to grow, and after the lapse of 4 weeks from the treatment with the selected compounds the herbicidal effects were evaluated. The results are shown in Table 27. The evaluation of the herbicidal effects was similarly conducted as to that of Experiment 1.

EXPERIMENT 9 (Foliage Treatment)

Upon seedling stage (two- or three-leaved stage) of ichibi (velvetleaf, *Abutilon theophrasti*), onamomi (heartleaf cocklebur, *Xanthium strumarium*) (4L stage), noasagao (blue morningglory, *Ipomoea indica*) and ooinutade (pale smartweed, *Persicaria lapathifolia*) which were grown on a cultivated soil put in pots of 1/8850 ares, a selected compound obtained in a manner analogous to Example 14, in suspended wettable powder, was sprayed to each plant. After that, the pots were kept in a glass chamber to allow each plant to grow, and after the lapse of 4 weeks from the treatment with the selected compounds the herbicidal effects were evaluated. The results are shown in Table 28. The evaluation of the herbicidal effects was similarly conducted as that of Experiment 1.

TABLE 26

| Compound No. | Quantity of Compound g/10a | Injury of Paddy | Herbicidal Effect |  |  |  |
|---|---|---|---|---|---|---|
|  |  |  | nobie | broad-leaved weed | hotarui | tamagaya-tsuri |
| [II-B] |  |  |  |  |  |  |
| 91 | 12.5 | 0.5 | 5 | 5 | 5 | 5 |
|  | 6.25 | 0 | 5 | 5 | 4 | 5 |
| 92 | 12.5 | 0 | 5 | 5 | 4 | 5 |
|  | 6.25 | 0 | 5 | 5 | 4 | 4 |
| 93 | 12.5 | 0.5 | 5 | 5 | 4 | 4 |
|  | 6.25 | 0.5 | 5 | 5 | 4 | 4 |
| 94 | 12.5 | 0.5 | 5 | 5 | 5 | 5 |
|  | 6.25 | 0.5 | 5 | 5 | 5 | 5 |
| 95 | 12.5 | 0 | 5 | 5 | 4 | 5 |
|  | 6.25 | 0 | 5 | 5 | 4 | 5 |
| 96 | 12.5 | 0.5 | 5 | 5 | 4 | 5 |
|  | 6.25 | 0 | 5 | 5 | 4 | 5 |
| 97 | 12.5 | 0 | 5 | 5 | 4 | 4 |

TABLE 26-continued

| Compound No. | Quantity of Compound g/10a | Injury of Paddy | Herbicidal Effect |  |  |  |
|---|---|---|---|---|---|---|
|  |  |  | nobie | broad-leaved weed | hotarui | tamagaya-tsuri |
|  | 6.25 | 0 | 5 | 5 | 4 | 4 |
| 98 | 12.5 | 0.5 | 5 | 5 | 5 | 5 |
|  | 6.25 | 0.5 | 5 | 5 | 4 | 5 |
| 99 | 12.5 | 0 | 5 | 5 | 4 | 5 |
|  | 6.25 | 0 | 5 | 5 | 4 | 4 |
| [II-C] |  |  |  |  |  |  |
| 100 | 12.5 | 0.5 | 5 | 5 | 5 | 5 |
|  | 6.25 | 0.5 | 5 | 5 | 5 | 5 |
| 101 | 12.5 | 1 | 5 | 5 | 4 | 5 |
|  | 6.25 | 0.5 | 5 | 5 | 4 | 5 |
| 102 | 12.5 | 0.5 | 5 | 5 | 4 | 5 |
|  | 6.25 | 0.5 | 5 | 5 | 4 | 5 |
| Comparative agent A | 12.5 | 0.5 | 4.5 | 5 | 4.5 | 5 |
|  | 6.25 | 0.5 | 4 | 5 | 3 | 5 |

Comparative agent-A: MO

TABLE 27

| Compound No. | Quantity of Compound g/10a | Herbicidal Effect |  |  |  |
|---|---|---|---|---|---|
|  |  | rice | cockspur | garden radish | aobiyu | mehishiba |
| [II-B] |  |  |  |  |  |  |
| 91 | 80 | 1 | 1 | 5 | 5 | 1 |
|  | 40 | 1 | 1 | 5 | 5 | 1 |
| 92 | 80 | 1 | 1 | 4 | 5 | 1 |
|  | 40 | 1 | 1 | 4 | 5 | 1 |
| 93 | 80 | 1 | 1 | 5 | 5 | 1 |
|  | 40 | 1 | 1 | 4 | 5 | 1 |
| 94 | 80 | 1 | 1 | 5 | 5 | 1 |
|  | 40 | 1 | 1 | 5 | 5 | 1 |
| 95 | 80 | 1 | 1 | 4 | 5 | 1 |
|  | 40 | 1 | 1 | 4 | 5 | 1 |
| 96 | 80 | 1 | 1 | 5 | 5 | 1 |
|  | 40 | 1 | 1 | 5 | 5 | 1 |
| 97 | 80 | 1 | 1 | 5 | 5 | 1 |
|  | 40 | 1 | 1 | 5 | 4 | 1 |
| 98 | 80 | 1 | 1 | 4 | 5 | 1 |
|  | 40 | 1 | 1 | 4 | 4 | 1 |
| 99 | 80 | 1 | 1 | 4 | 5 | 1 |
|  | 40 | 1 | 1 | 4 | 4 | 1 |
| [II-C] |  |  |  |  |  |  |
| 100 | 80 | 1 | 1 | 5 | 5 | 1 |
|  | 40 | 1 | 1 | 5 | 5 | 1 |
| 101 | 80 | 1 | 1 | 5 | 5 | 1 |
|  | 40 | 1 | 1 | 5 | 5 | 1 |
| 102 | 80 | 1 | 1 | 5 | 5 | 1 |
|  | 40 | 1 | 1 | 5 | 5 | 1 |
| Comparative agent B | 80 | 0 | 1 | 3 | 5 | 1 |
|  | 40 | 0 | 1 | 1 | 5 | 0 |

Comparative agent-B: Propanil

TABLE 28

| Compound No. | Quantity of Compound g/10a | Herbicidal Effect |  |  |  |
|---|---|---|---|---|---|
|  |  | ichibi | onamomi | noasagao | ooinutade |
| [II-B] |  |  |  |  |  |

TABLE 28-continued

| Compound No. | Quantity of Compound g/10a | Herbicidal Effet ichibi | onamomi | noasagao | ooinutade |
|---|---|---|---|---|---|
| 91 | 8 | 5 | 5 | 5 | 5 |
|  | 4 | 5 | 4 | 4 | 5 |
| 97 | 8 | 5 | 4 | 4 | 5 |
|  | 4 | 5 | 4 | 4 | 4 |
| [I-B] | | | | | |
| 100 | 8 | 5 | 5 | 5 | 5 |
|  | 4 | 5 | 5 | 5 | 5 |
| 102 | 8 | 5 | 5 | 5 | 5 |
|  | 4 | 5 | 5 | 4 | 4 |
| Comparative agentC | 8 | 3 | 5 | 4 | 5 |
|  | 4 | 3 | 4 | 3 | 5 |

Comparative Agent-C: Pursuit

INDUSTRIAL APPLICABILITY

N-phenyltetrahydrophthalamic acid derivatives that are novel compounds of the present invention, exhibit excellent herbicidal activity, and are useful as a herbicide which can be widely applied to upland, paddy field, orchard, turf, forest, non-crop land, etc., and which is not harmful to crops.

We claim:

1. An imidoylchloride derivative represented by the general formula [III],

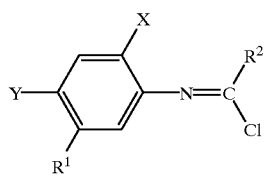

[III]

wherein X and Y each individually represent hydrogen atoms or halogen atoms, $R^1$ represents a lower alkoxycarbonylalkylthio group, and $R^2$ represents a lower alkyl group, a halogenated lower alkyl group or a substituted or unsubstituted phenyl group.

2. An imidoylchloride derivative represented by the general formula [IV],

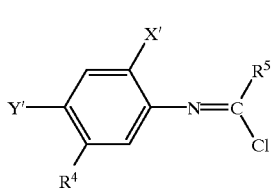

[IV]

wherein X' and Y' each individually represent hydrogen atoms or halogen atoms, $R^4$ represents a hydrogen atom, a lower alkoxy group, a lower alkenyloxy group, a lower alkynyloxy group, cycloalkyloxy group, a lower alkoxycarbonyl group, a lower alkoxycarbonylalkoxy group or a lower alkoxycarbonylalkylthio group, $R^5$ represents:

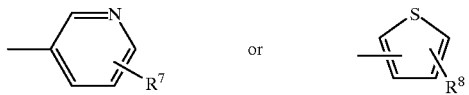

wherein $R^7$ represents a hydrogen atom, a halogen atom, a lower alkyl group or a lower alkoxycarbonyl group, and $R^8$ represents a hydrogen atom, a halogen atom or a lower alkyl group.

3. A method of producing an imidoylchloride derivative represented by the general formula [III], said method being characterized in that an anilide derivative represented by the general formula [IX] is reacted in the presence of a dehydrochlorinating agent,

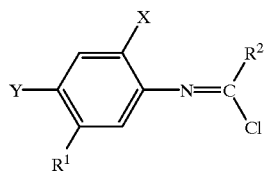

[III]

wherein X and Y each individually represent hydrogen atoms or halogen atoms, $R^1$ represents a lower alkoxycarbonylalkylthio group, and $R^2$ represents a lower alkyl group, a halogenated lower alkyl group or a substituted or unsubstituted phenyl group,

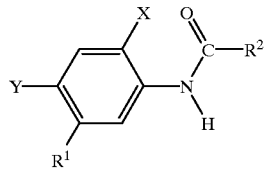

[IX]

wherein X and Y each individually represent hydrogen atoms or halogen atoms, $R^1$ represents a lower alkoxycarbonylalkylthio group, and $R^2$ represents a lower alkyl group, a halogenated lower alkyl group or a substituted or unsubstituted phenyl group.

4. A method of producing an imidoylchloride derivative represented by the general formula [IV], said method being characterized in that an anilide derivative represented by the general formula [X] is reacted in the presence of a dehydrochlorinating agent,

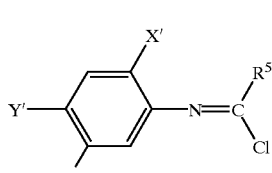

[IV]

wherein X' and Y' each individually represent hydrogen atoms or halogen atoms, $R^4$ represents a hydrogen atom, a lower alkoxy group, a lower alkenyloxy group, a lower alkynyloxy group, cycloalkyloxy group, a lower alkoxycarbonyl group, a lower alkoxycarbonylalkoxy group or a lower alkoxycarbonylalkylthio group, $R^5$ represents:

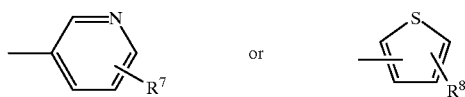 or wherein R⁷ represents a hydrogen atom, a halogen atom, a lower alkyl group or a lower alkoxycarbonyl group, and R⁸ represents a hydrogen atom, a halogen atom or a lower alkyl group,

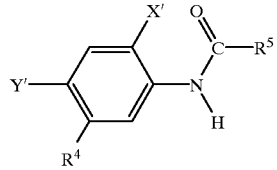

[X]

wherein X' and Y' each individually represent hydrogen atoms or halogen atoms, R⁴ represents a hydrogen atom, a lower alkoxy group, a lower alkenyloxy group, a lower alkynyloxy group, cycloalkyloxy group, a lower alkoxycarbonyl group, a lower alkoxycarbonylalkoxy group or a lower alkoxycarbonylalkylthio group, and R⁵ represents:

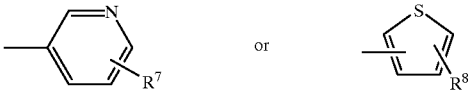

wherein R⁷ represents a hydrogen atom, a halogen atom, a lower alkyl group or a lower alkoxycarbonyl group, and R⁸ represents a hydrogen atom, a halogen atom or a lower alkyl group.

* * * * *